United States Patent [19]

Mastri et al.

[11] Patent Number: 5,423,471
[45] Date of Patent: * Jun. 13, 1995

[54] APPARATUS FOR APPLYING TWO-PART SURGICAL FASTENERS IN LAPAROSCOPIC OR ENDOSCOPIC PROCEDURES

[75] Inventors: Dominick L. Mastri, Bridgeport; Michael S. Kolesa, Norwalk; Leonard Stern, Meriden, all of Conn.

[73] Assignee: United States Surgical Corporation, Norwalk, Conn.

[*] Notice: The portion of the term of this patent subsequent to May 17, 2011 has been disclaimed.

[21] Appl. No.: 27,865

[22] Filed: Mar. 8, 1993

Related U.S. Application Data

[63] Continuation-in-part of Ser. No. 955,828, Oct. 2, 1992.

[51] Int. Cl.$^6$ .................................. A61B 17/068
[52] U.S. Cl. ...................... 227/181; 227/19; 227/175
[58] Field of Search .............. 227/19, 175, 176, 177, 227/178, 180, 181

[56] References Cited

U.S. PATENT DOCUMENTS

| | | |
|---|---|---|
| 2,028,635 | 1/1936 | Wappler . |
| 3,079,606 | 3/1963 | Bobrov et al. . |
| 3,490,675 | 1/1970 | Green et al. . |
| 3,499,591 | 3/1970 | Green . |
| 3,788,303 | 1/1974 | Hall . |
| 3,892,228 | 7/1975 | Mitsui . |
| 4,111,206 | 9/1978 | Vishnevsky et al. . |
| 4,273,129 | 6/1981 | Boebel . |
| 4,354,628 | 10/1982 | Green . |
| 4,402,445 | 9/1983 | Green . |
| 4,429,695 | 2/1984 | Green . |
| 4,493,322 | 1/1985 | Becht . |
| 4,506,670 | 3/1985 | Crossley . |
| 4,506,671 | 3/1985 | Green . |
| 4,513,746 | 4/1985 | Aranyi et al. . |
| 4,520,817 | 6/1985 | Green . |
| 4,527,724 | 7/1985 | Chow et al. . |
| 4,566,620 | 1/1986 | Green et al. . |
| 4,573,622 | 3/1986 | Green et al. ............... 227/19 |
| 4,589,416 | 5/1986 | Green . |
| 4,591,085 | 5/1986 | DiGiovanni . |
| 4,606,345 | 8/1986 | Dorband et al. . |
| 4,608,981 | 9/1986 | Rothfuss et al. . |
| 4,633,861 | 1/1987 | Chow et al. . |
| 4,633,874 | 1/1987 | Chow et al. . |
| 4,665,916 | 5/1987 | Green . |
| 4,688,555 | 8/1987 | Wardle . |
| 4,721,099 | 1/1988 | Chikama . |
| 4,728,020 | 3/1988 | Green et al. . |
| 4,741,336 | 5/1988 | Failla et al. . |
| 4,754,909 | 7/1988 | Barker et al. .......................... 227/19 |
| 4,807,628 | 2/1989 | Peters et al. . |
| 4,841,950 | 6/1989 | Fukuda . |
| 4,863,088 | 9/1989 | Redmond et al. . |
| 4,869,414 | 9/1989 | Green et al. . |
| 4,880,015 | 11/1989 | Nierman . |
| 4,881,544 | 11/1989 | Green et al. . |
| 4,932,960 | 6/1990 | Green et al. . |
| 4,941,455 | 7/1990 | Watanabe et al. . |
| 4,947,827 | 8/1990 | Opie et al. . |
| 5,040,715 | 8/1991 | Green et al. . |
| 5,042,707 | 8/1991 | Taheri ........................ 227/175 X |
| 5,065,929 | 11/1991 | Schulze et al. . |
| 5,071,430 | 12/1991 | de Salis et al. . |
| 5,083,695 | 1/1992 | Foslien et al. . |
| 5,100,418 | 3/1992 | Yoon et al. . |
| 5,156,315 | 10/1992 | Green et al. . |
| 5,156,614 | 10/1992 | Green et al. . |
| 5,253,793 | 10/1993 | Green et al. . |
| 5,289,963 | 3/1994 | McGarry et al. . |
| 5,312,023 | 5/1994 | Green et al. . |

FOREIGN PATENT DOCUMENTS 8302247  7/1983  WIPO ................... 227/19

Primary Examiner—Rinaldi I. Rada

[57] ABSTRACT

Apparatus is disclosed for applying two-part surgical fasteners during endoscopic or laparoscopic procedures. The apparatus includes a handle assembly, an endoscopic portion which extends from the handle assembly, and a tool assembly pivotally associated with a distal end of the endoscopic portion for applying a two-part surgical fastener. A mechanism is provided for effectuating articulated pivotal movement of the fastener applying tool assembly within an angular sector of rotation to increase the operational range of the instrument.

14 Claims, 42 Drawing Sheets

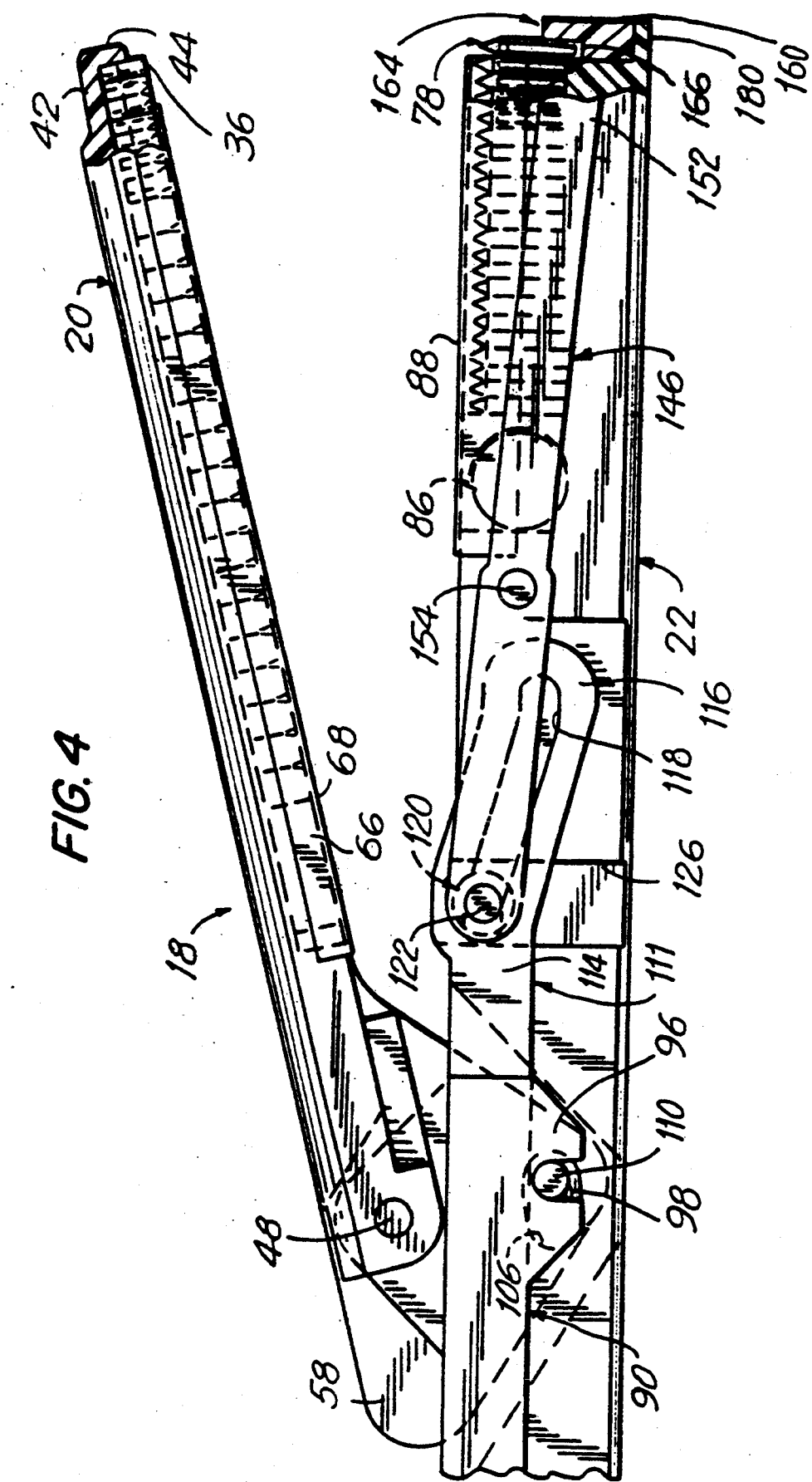

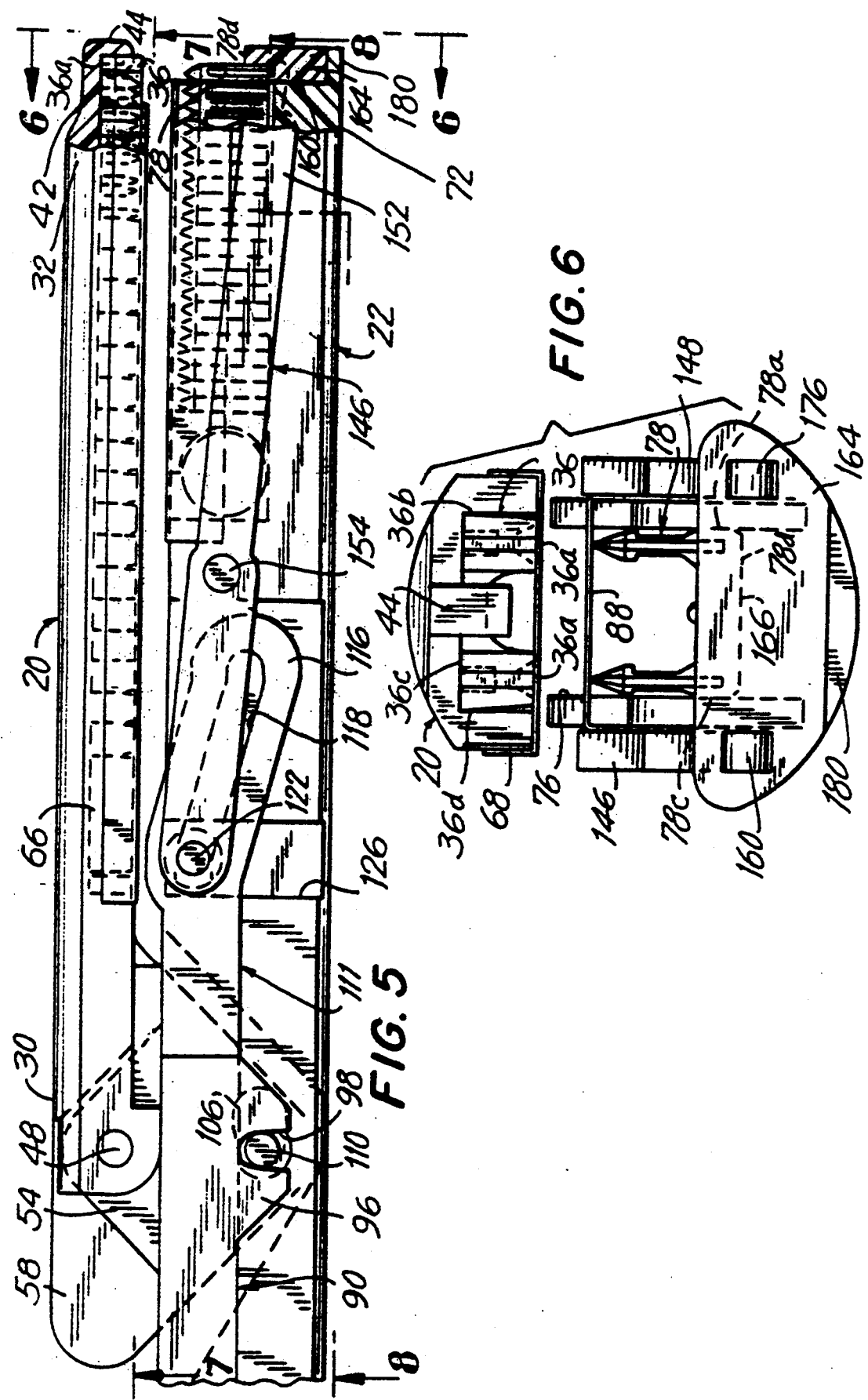

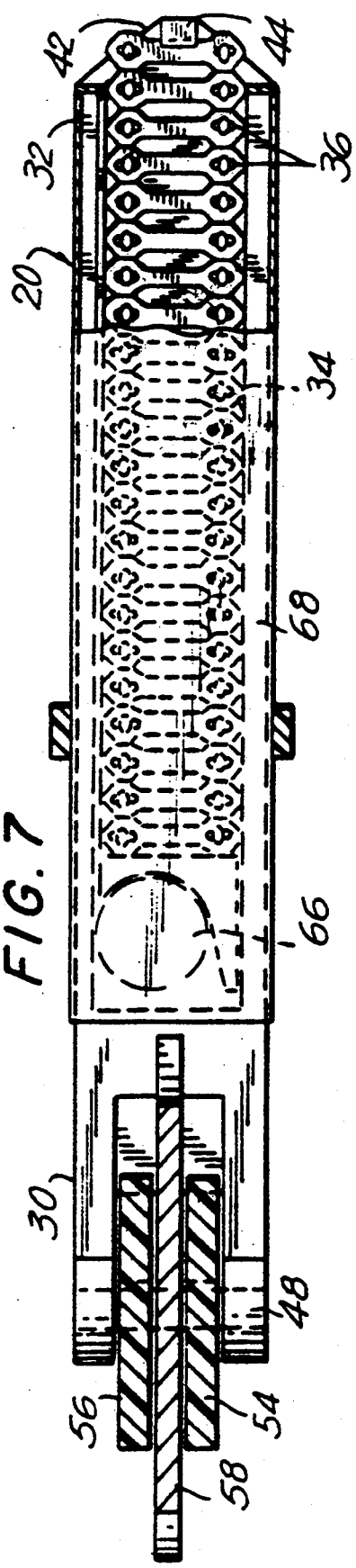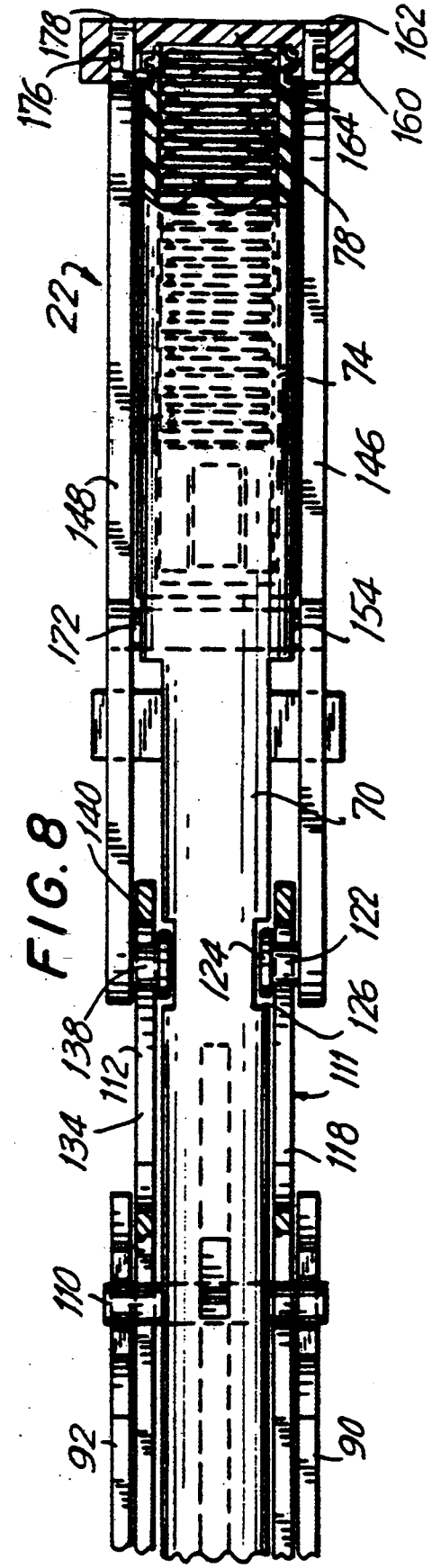

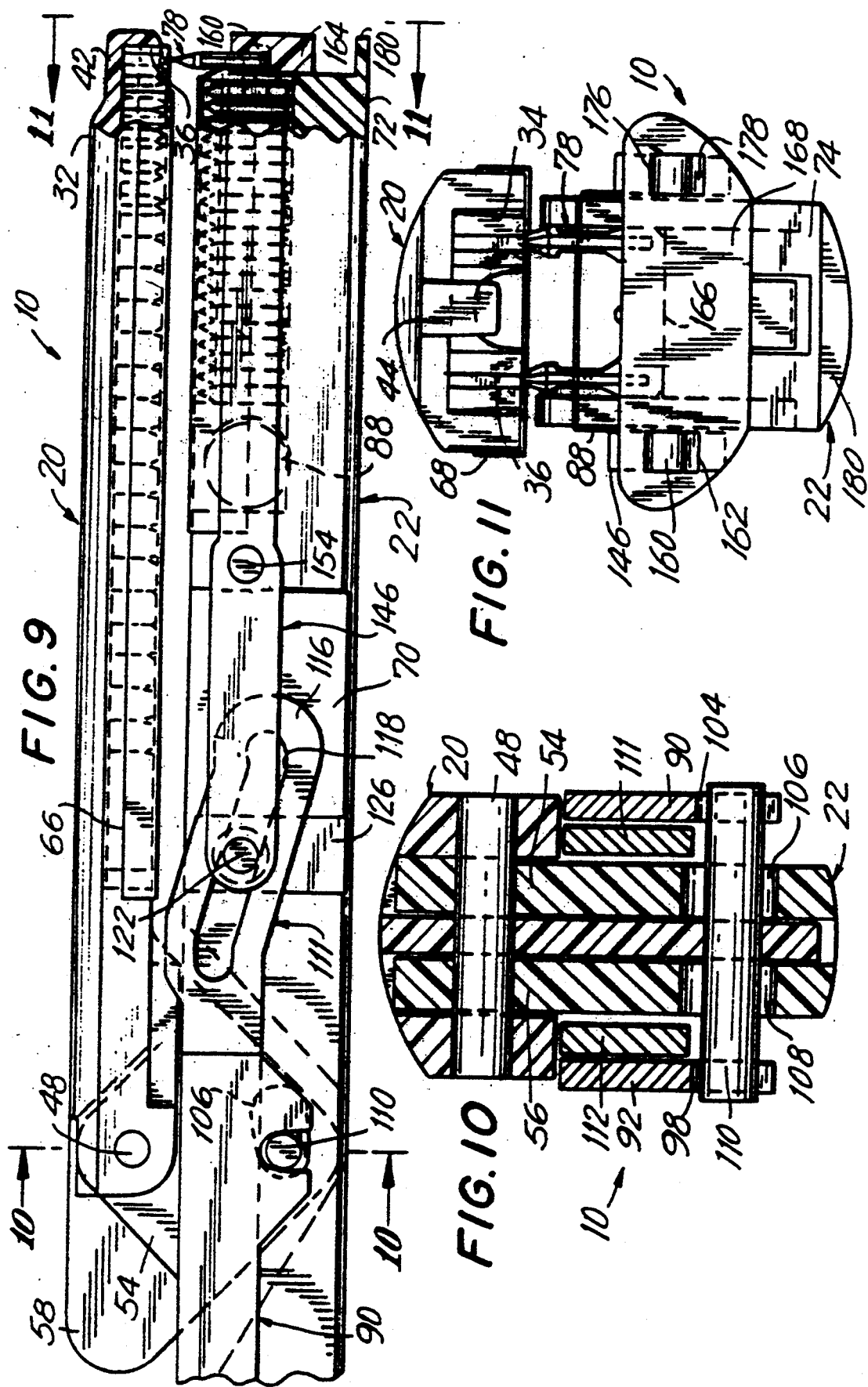

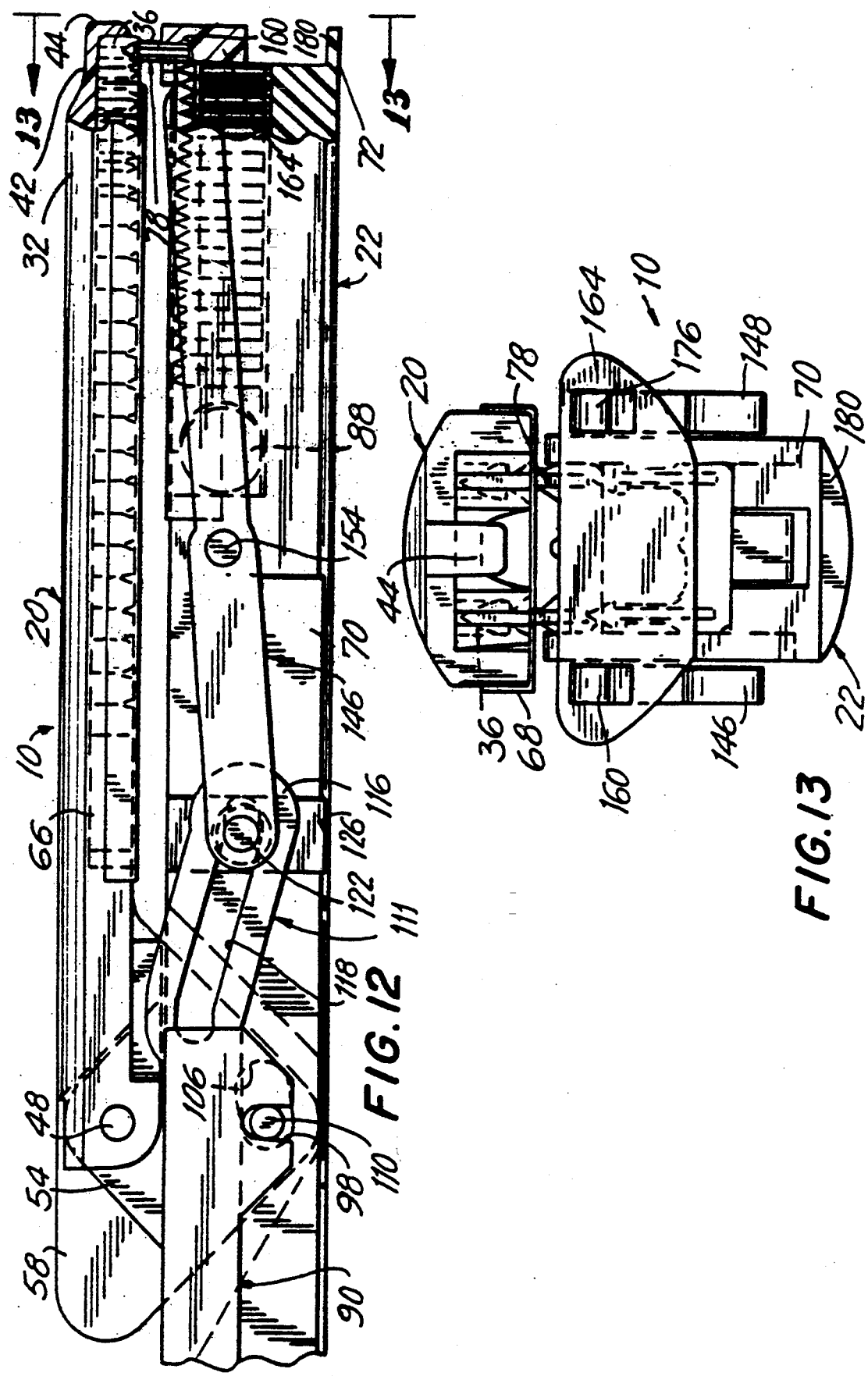

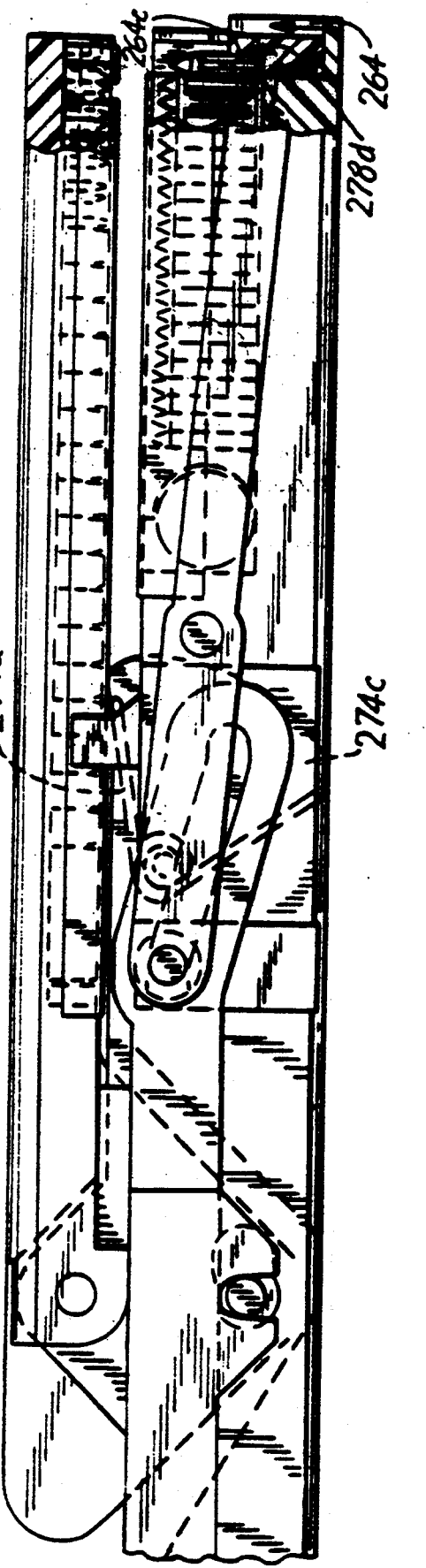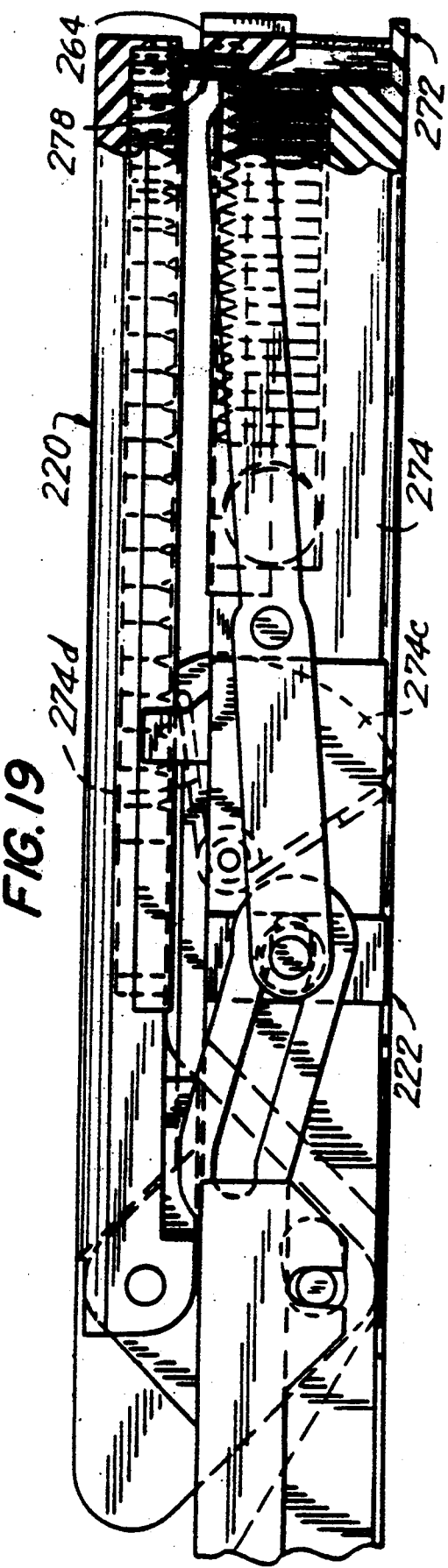

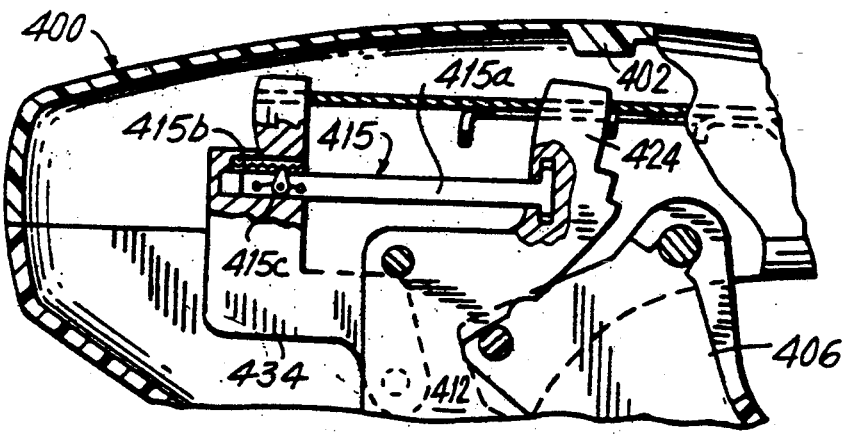
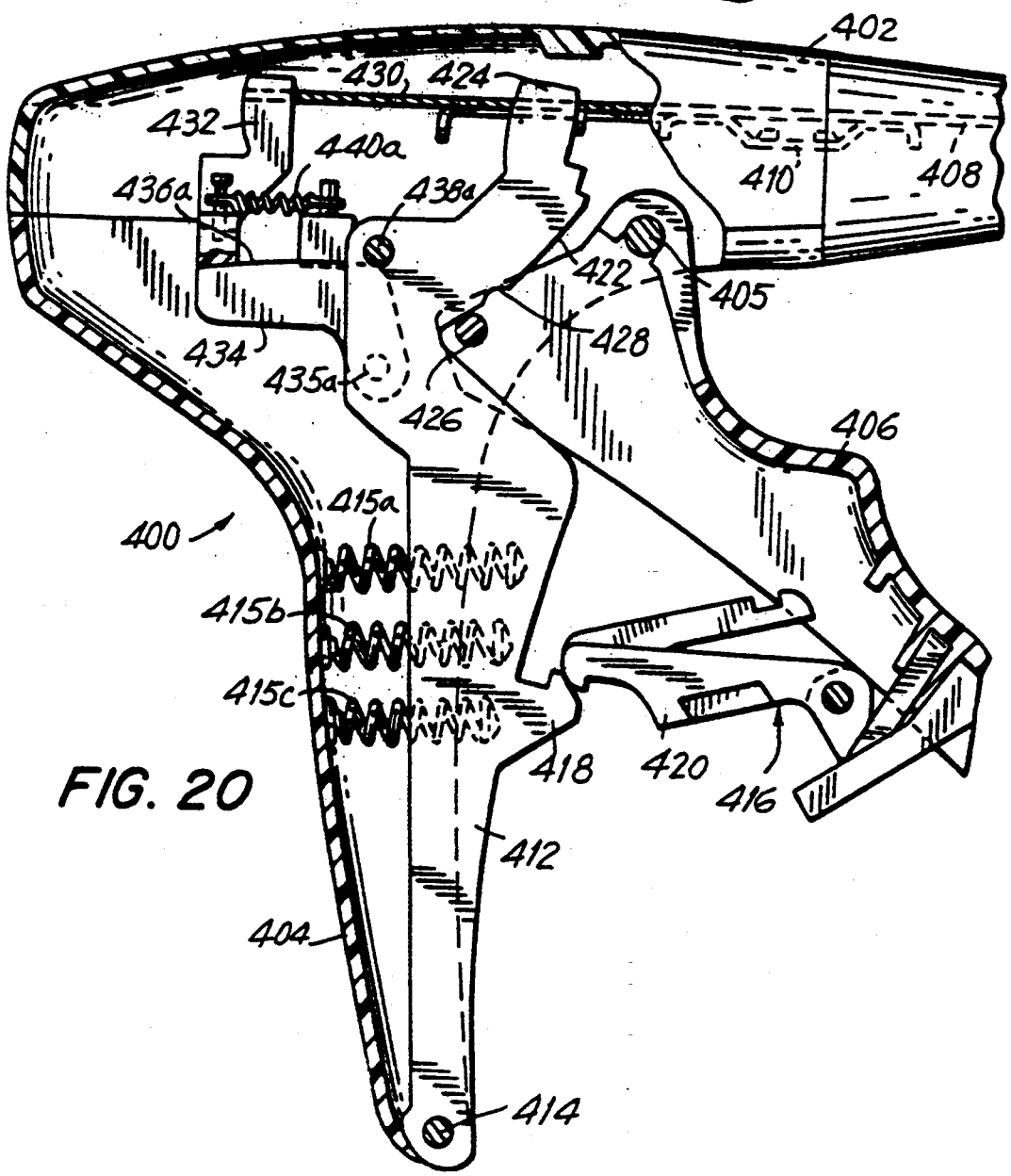
FIG. 20A
FIG. 20

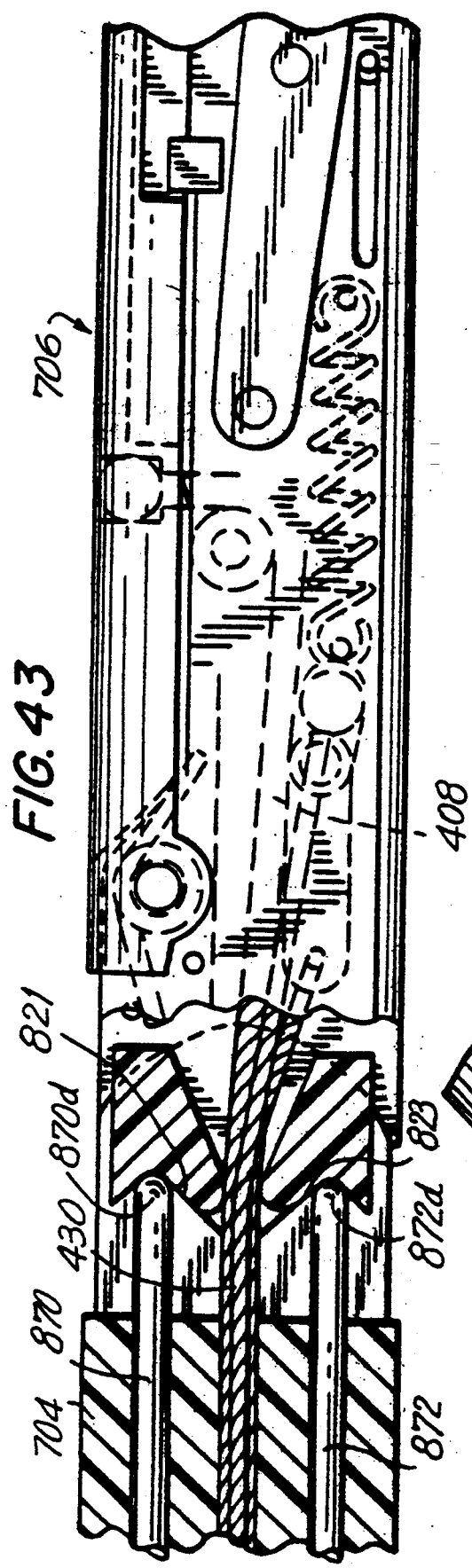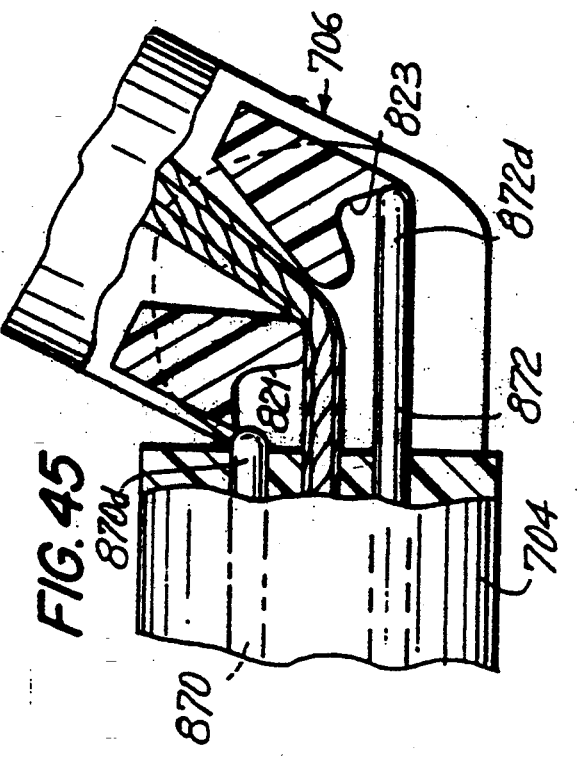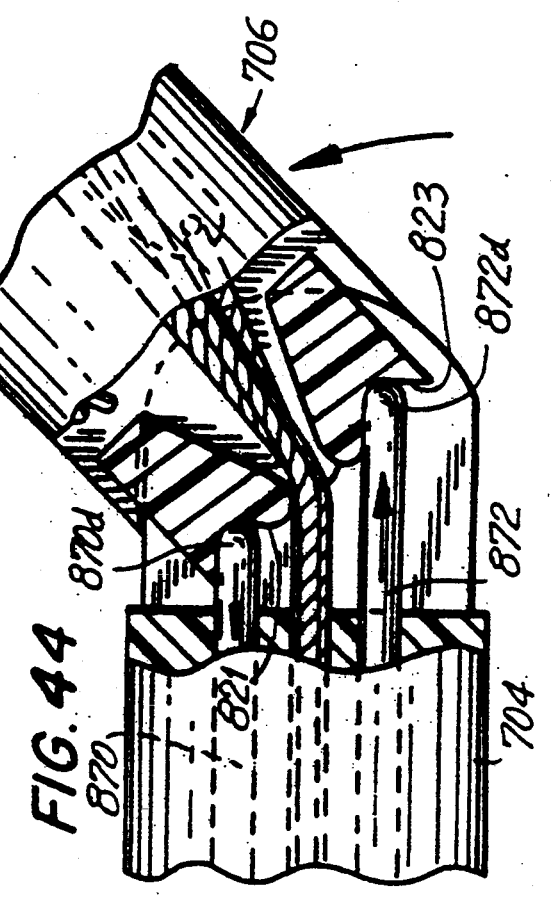

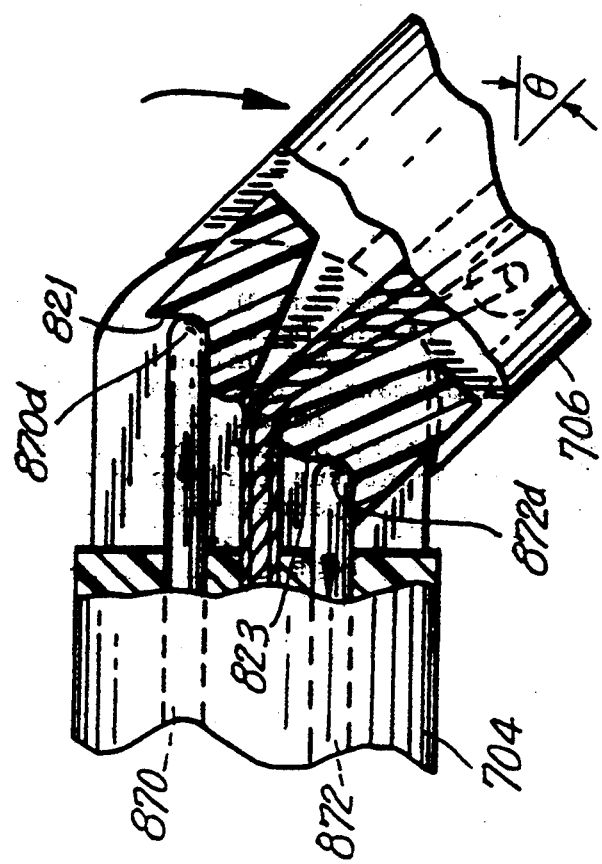
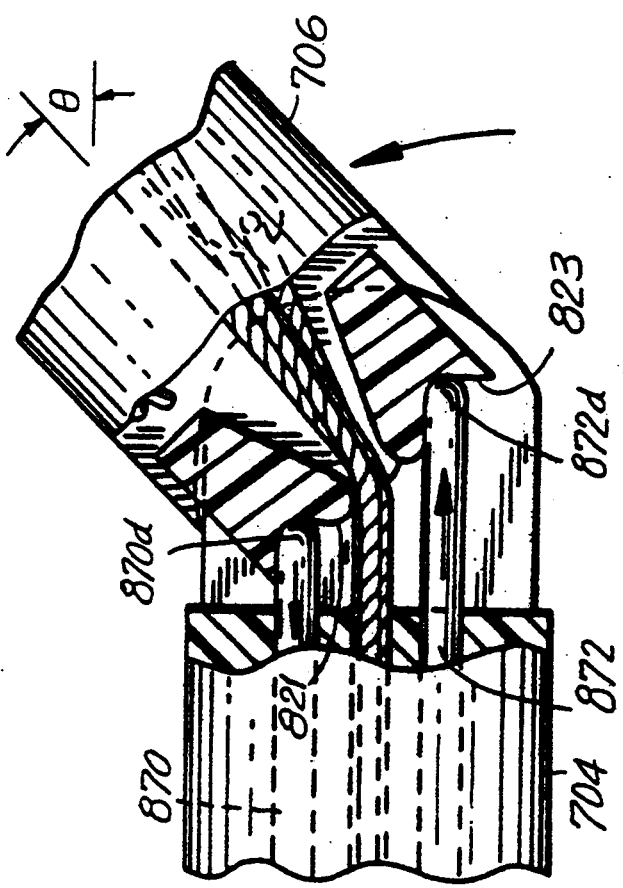

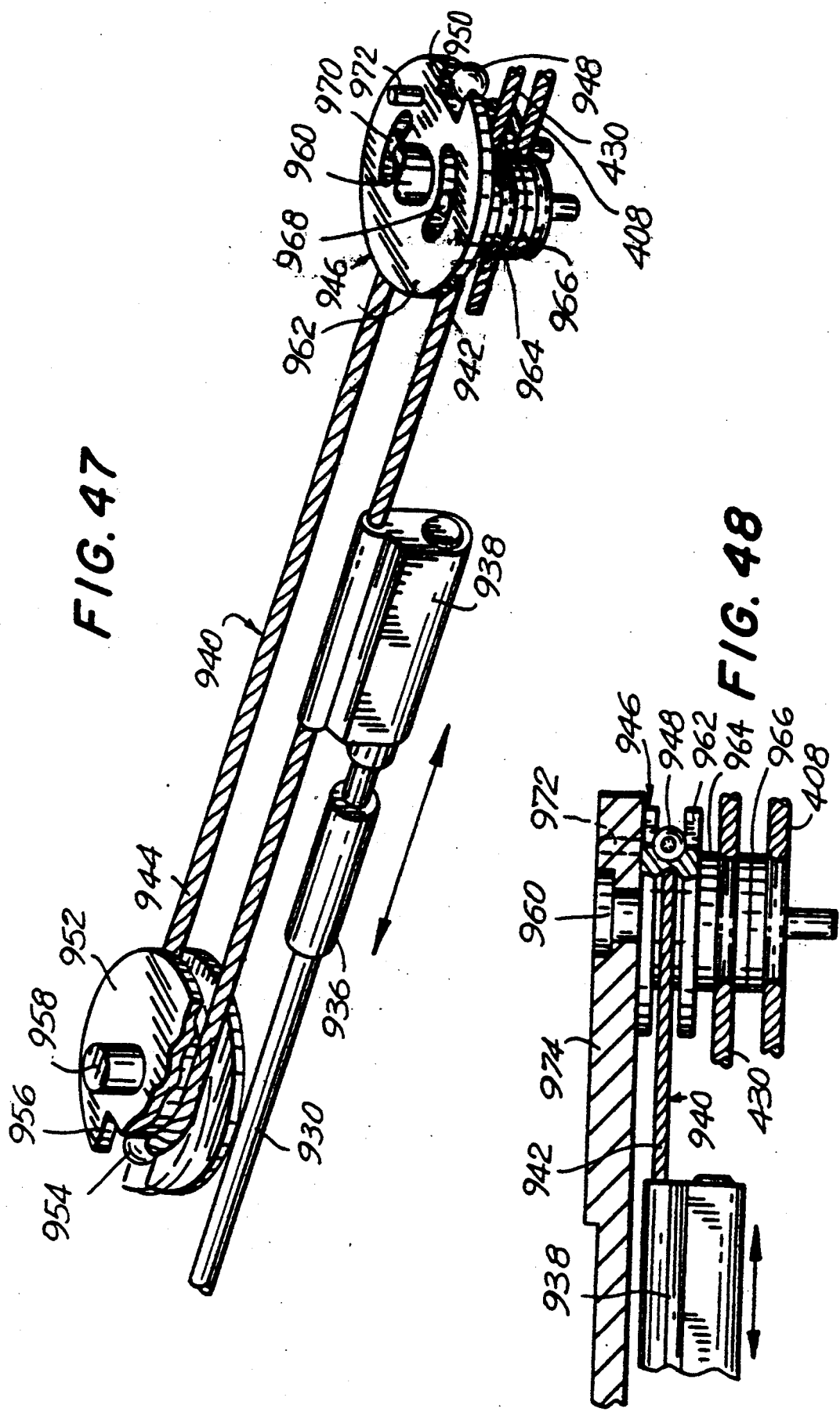

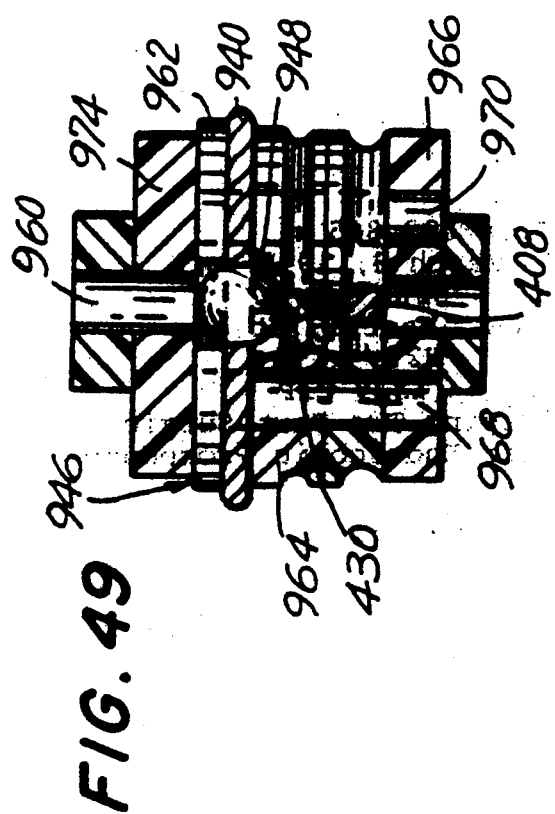
FIG. 49
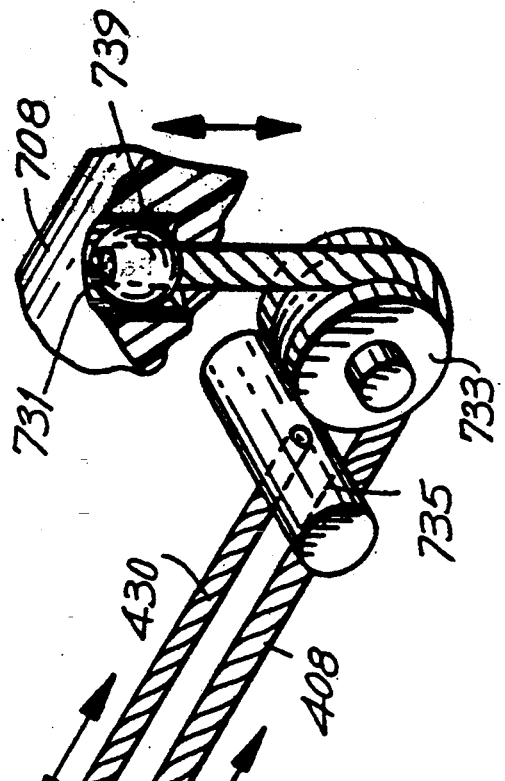
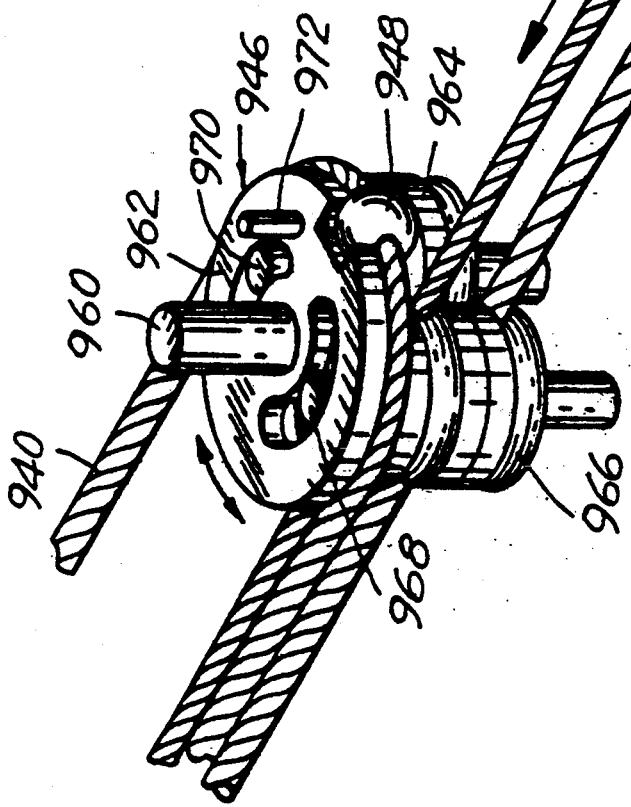
FIG. 50

APPARATUS FOR APPLYING TWO-PART SURGICAL FASTENERS IN LAPAROSCOPIC OR ENDOSCOPIC PROCEDURES

CROSS-REFERENCE TO RELATED APPLICATION

This application is a continuation-in-part of U.S. application Ser. No. 07/955,828 which was filed Oct. 2, 1992 and is herein incorporated by reference.

BACKGROUND OF THE INVENTION

1. Field of the Invention

This invention relates to apparatus for applying surgical fasteners, and more particularly to a surgical apparatus for applying a two-part surgical fastener during endoscopic or laparoscopic procedures.

2. Background of Related Art

In laparoscopic and endoscopic surgical procedures, surgery is performed through a small incision or puncture made in the patient's body to provide access for an endoscopic tube or a cannula device. Once extended into the patient's body, the cannula allows insertion of surgical instruments into the abdominal cavity. One such instrument is an apparatus for applying one or more surgical staples endoscopically as disclosed in U.S. Pat. No. 5,040,715 which issued to Green et al. This apparatus makes a longitudinal incision while simultaneously applying at least one row of staples on each side of the incision.

Up to the present, many devices for endoscopically applying fasteners have contemplated metal staples. It is advantageous however, to have the ability to apply a two-part non-metallic surgical fastener during such endoscopic procedures. Two-part absorbable fasteners are disclosed in U.S. Pat. Nos. 4,534,352, 4,589,416, 4,665,916 and 4,932,960. These fasteners include a fastener member which pierces the tissue from one side and a retainer member which interlocks with the fastener member on the other side of the tissue. Subsequent to their application, the fasteners are advantageously absorbed by the body.

The present invention provides an apparatus for individually applying two-part surgical fasteners in endoscopic or laparoscopic procedures.

SUMMARY OF THE INVENTION

Because endoscopic procedures are more common than laparoscopic procedures, the present invention shall be discussed in terms of endoscopic procedures and apparatus. However, use herein of terms such as "endoscopic", "endoscopically", and "endoscopic portion", among others, should not be construed to limit the present invention to an apparatus for use only in conjunction with an endoscopic tube. To the contrary, it is believed that the present invention may find use in procedures wherein access is limited to a small incision including but not limited to laparoscopic procedures.

In the drawings and in the description which follows, the term "proximal", as is traditional, will refer to the end of the apparatus which is closest to the operator, while the term "distal" will refer to the end which is furthest from the operator.

In accordance with the subject invention, a surgical apparatus is disclosed for placing at least one two-part surgical fastener endoscopically. The apparatus comprises actuation means, an endoscopic portion which extends from the actuation means, and means associated with a distal end of the endoscopic portion for effectuating the application of a two-part surgical fastener. The actuation means may be either a manually operated handle or a powered handle. Further, the apparatus includes sealing means within the endoscopic portion to maintain positive pressure at the surgical site.

Preferably, the apparatus includes means for supporting the fastener portion of the two-part surgical fastener, and means for supporting the retainer portion of the two-part surgical fastener in a position relative to the fastener portion thereof. The apparatus also comprises means for approximating the retainer portion supporting means toward the fastener portion supporting means. Furthermore, the fastener applying means comprises means for driving the fastener portion of the two-part surgical fastener into engagement with the retainer portion of the two-part surgical fastener.

In a preferred embodiment of the subject invention, the retainer portion supporting means comprises an upper driving arm having a channel formed therein for maintaining and locating at least one retainer portion, while the fastener portion supporting means comprises a lower driving arm having a channel formed therein for maintaining and locating at least one fastener portion. The driving means is connected to the handle means and includes camming means and associated pivoting means. The camming means comprises at least one cam member having an angled head portion with an elongated cam slot defined therein. The pivoting means comprises at least one elongated rocker member pivotably connected intermediate the length thereof to the lower driving arm. The rocker member includes means for lifting the fastener portion of the two-part surgical fastener, and further comprises a cam follower for translation within the camming slot of the cam member. Preferably, the lifting means has a shelf defined therein for accommodating and retaining the fastener portion. The lifting means may be independently movable transversely of the endoscopic portion or it may be movably supported on rails associated with the endoscopic portion.

In a preferred embodiment of the subject invention, the means for approximating the retainer portion supporting means and the fastener portion supporting means comprises first transmission in the form of a first cable extending operatively from the handle assembly, through the endoscopic portion, to the retainer portion supporting means. The means for driving the fastener portion into engagement with the retainer portion comprises second transmission means in the form of a second cable extending operatively from the handle assembly, through the endoscopic portion, to linkage means configured for lifting the fastener portion toward the retainer portion.

Preferably, the handle assembly includes a pivoting actuation handle associated with the first transmission cable and the second transmission cable. The actuation handle is movable through a first distance to effectuate movement of the first transmission cable and movable through a second further distance to effectuate movement of the second transmission cable. Alternatively, the handle assembly can include a first pivoting actuation handle for effectuating movement of the first transmission cable and a second actuation handle for effectuating movement of the second transmission cable.

In another embodiment of the subject invention, the surgical apparatus comprises handle means, an endoscopic portion extending from the handle means and defining a longitudinal axis, tool means pivotally associated with a distal end portion of the endoscopic portion for effectuating application of the two-part surgical fastener, and means for effectuating pivotal movement of the tool means relative to the longitudinal axis of the endoscopic portion within an angular sector of rotation.

Preferably, the means for effectuating pivotal movement of the tool means comprises a pair of reciprocatingly movable parallel rod members extending operatively from rod actuation means, through said endoscopic portion, to respective reception areas in said tool means. Alternatively, the means for effectuating pivotal movement of the tool means can comprise third transmission means including a looped articulation cable having a leading portion and a trailing portion. The leading portion of the articulation cable is associated with the tool means, while the trailing portion thereof is associated with means for reciprocatingly moving the looped articulation cable.

Further features of the subject invention will become more apparent from the following description of the subject invention.

BRIEF DESCRIPTIONS OF THE DRAWINGS

Preferred embodiments of the surgical apparatus of the subject invention will be described hereinbelow with reference to the drawings wherein:

FIG. 1A is a cross-sectional view taken along lines 1A—1A of FIG. 1 illustrating the sealing means which allows the surgical site to be maintained at positive pressure;

FIG. 4 is a side elevational view of the apparatus of FIG. 1 with the retainer supporting portion in the open position;

FIG. 5 is a side elevational view of the apparatus of FIG. 1 with the retainer supporting portion in the closed position;

FIG. 6 is a front elevational view taken along lines 6—6 of FIG. 5;

FIG. 7 is a plan view, partially in cross-section, taken along lines 7—7 of FIG. 5 illustrating the retainer supporting portion of the apparatus of FIG. 1;

FIG. 8 is a plan view, partially in cross-section, taken along lines 8—8 of FIG. 5 illustrating the fastener supporting portion of the apparatus of FIG. 1;

FIG. 9 is a side elevational view of the apparatus of FIG. 1 with the retainer supporting portion in the closed position and further illustrating initial advancement of the distalmost fastener toward the corresponding distalmost retainer;

FIG. 10 is a cross-sectional view taken along lines 10—10 of FIG. 9;

FIG. 11 is a front elevational view taken along lines 11—11 of FIG. 9;

FIG. 12 is a side elevational view of the apparatus of FIG. 1 with the retainer supporting portion in the closed position and showing the distalmost fastener during insertion into the corresponding distalmost retainer;

FIG. 13 is a front elevational view taken along lines 13—13 of FIG. 12;

FIG. 18 is a side elevational view of the apparatus of FIG. 14 with the retainer supporting portion in the closed position;

FIG. 19 is a side elevational view of the apparatus of FIG. 14 with the retainer supporting portion in the closed position and showing the distalmost fastener during insertion into the corresponding distalmost retainer;

FIG. 20 is a side elevational view, partially in cross-section, of a first embodiment of a handle assembly in accordance with the subject invention;

FIG. 20A is a side elevational view, partially in cross-section, of an alternative embodiment of the handle assembly of FIG. 20 which includes a mechanism for controlling handle actuation;

FIG. 43 is a partial cross-sectional view of the distal end portion of the apparatus of FIG. 38 illustrating the 0° position of the fastener applying assembly thereof;

FIG. 44 is a partial cross-sectional view of the distal end portion of the apparatus of FIG. 38 with the fastener applying assembly thereof articulated through an angular degree of rotation of about 32.5° in a counter-clockwise direction;

FIG. 44A is a partial cross-sectional view of the distal end portion of the apparatus of FIG. 38 with the fastener applying assembly thereof articulated through an angular degree of rotation of about 45° in a counter-clockwise direction;

FIG. 44B is a partial cross-sectional view of the distal end portion of the apparatus of FIG. 38 with the fastener applying assembly thereof articulated through an angular degree of rotation of about −45° in a clockwise direction.

FIG. 45 is a partial cross-sectional view of the distal end portion of the apparatus of FIG. 38 with the fastener applying assembly thereof articulated through an angular degree of rotation in a counter-clockwise direction;

FIG. 47 is a perspective view of the articulation cable assembly which is associated with the articulation mechanism of FIG. 46;

FIG. 48 is a side elevational view of the articulation cable assembly of FIG. 47;

FIG. 49 is a cross-sectional view of the articulation cable assembly of FIG. 47;

FIG. 50 is a perspective view of the leading portion of the articulation cable assembly of FIG. 47;

FIG. 51A is a perspective view of the fastener applying assembly of the apparatus of FIG. 38 swept through an angular sector of rotation;

Figure 38:
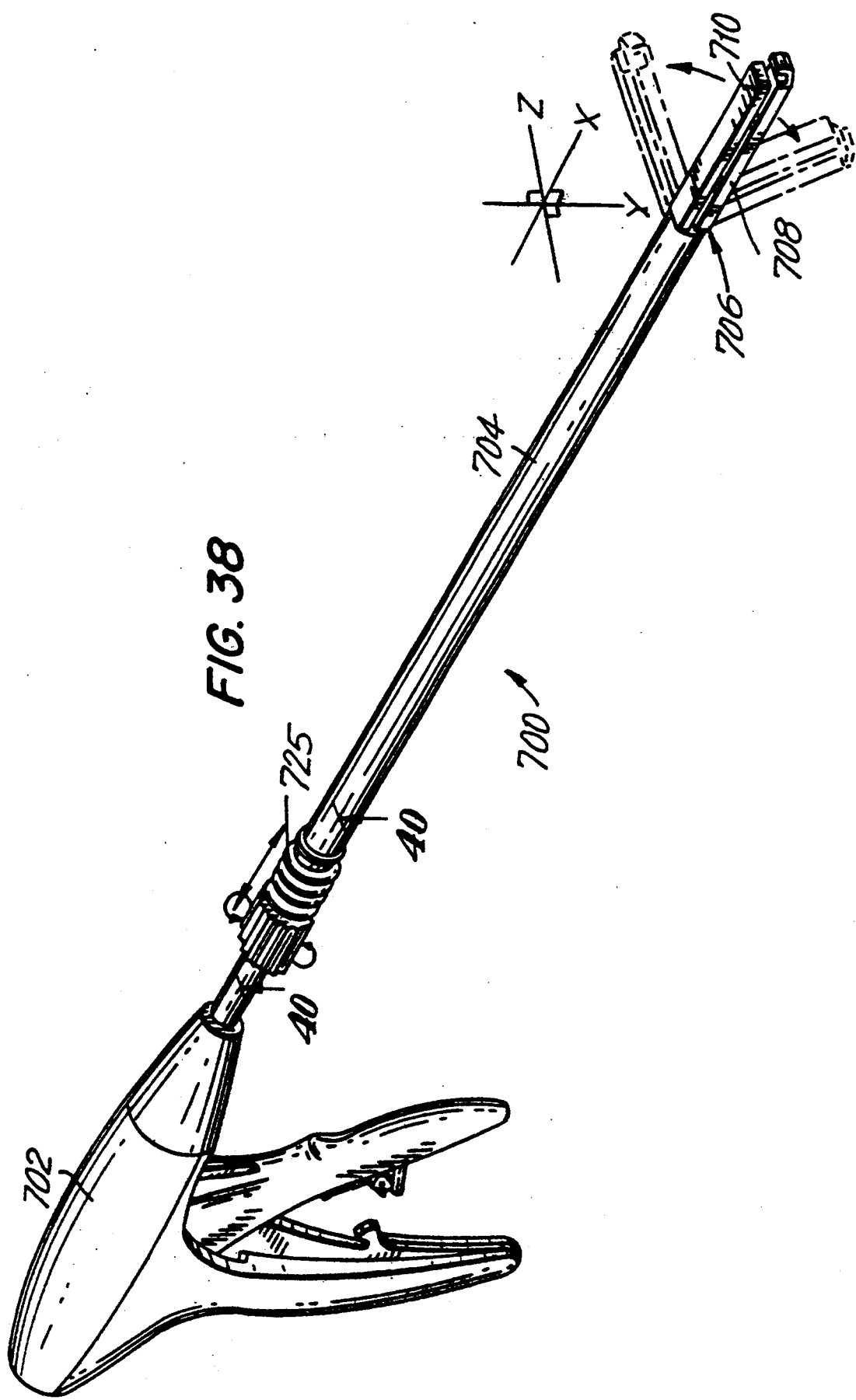
FIG. 38 is a perspective view of an alternative embodiment of the apparatus for endoscopic application of two-part surgical fasteners in accordance with the subject invention in which the fastener applying assembly is adapted to pivot relative to the endoscopic portion of the instrument.
Figure 53:
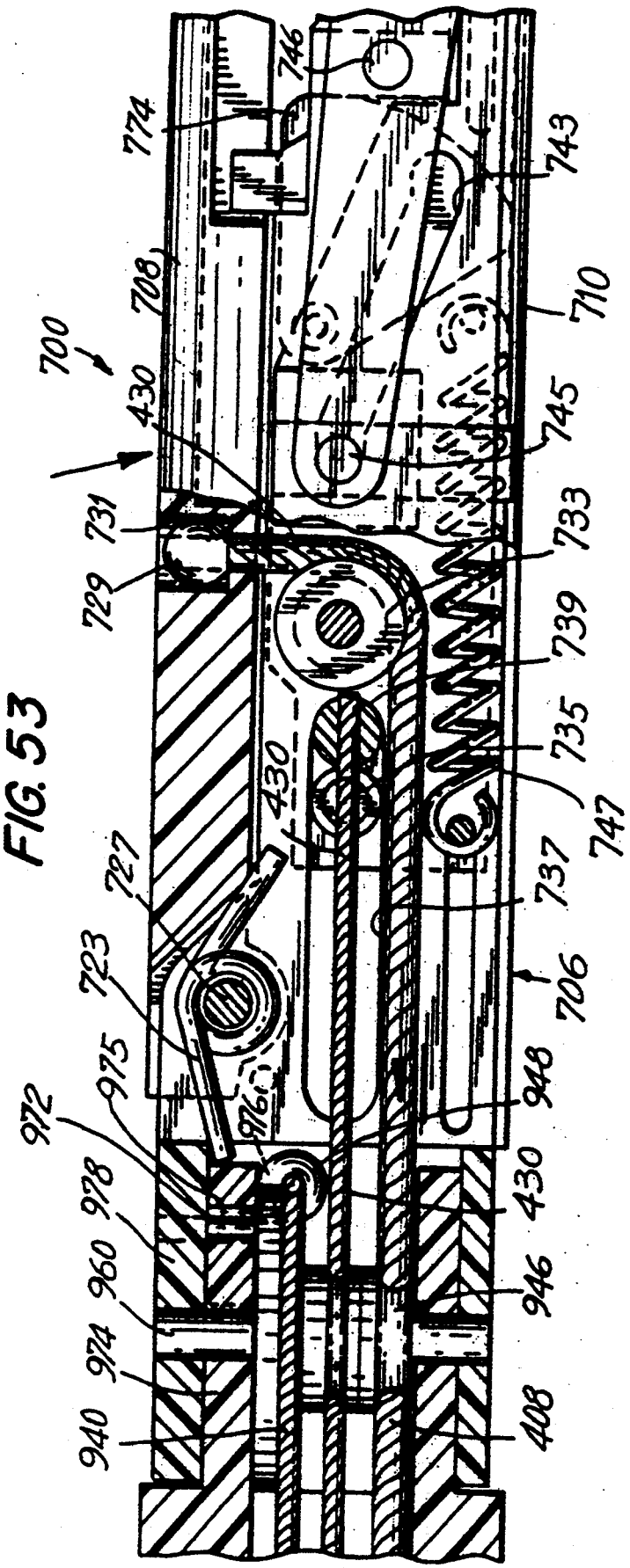
Figure 54:
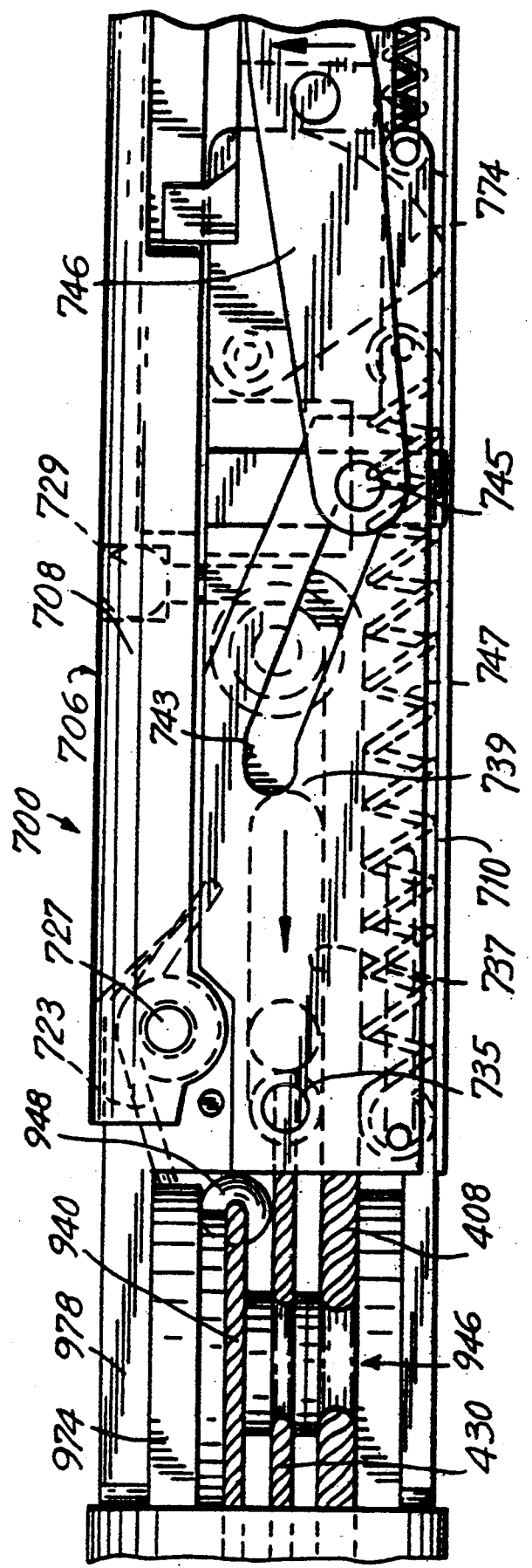

FIG. 53 is a side elevational view of the fastener applying assembly of the apparatus of FIG. 38 with the retainer supporting portion thereof in a closed position; and FIG. 54 is a side elevational view of the fastener applying assembly of the apparatus of FIG. 38 with the retainer supporting portion thereof in the closed position and further illustrating actuation of the fastener driving mechanism of the apparatus.

DETAILED DESCRIPTION OF THE PREFERRED EMBODIMENTS

Figure 1:
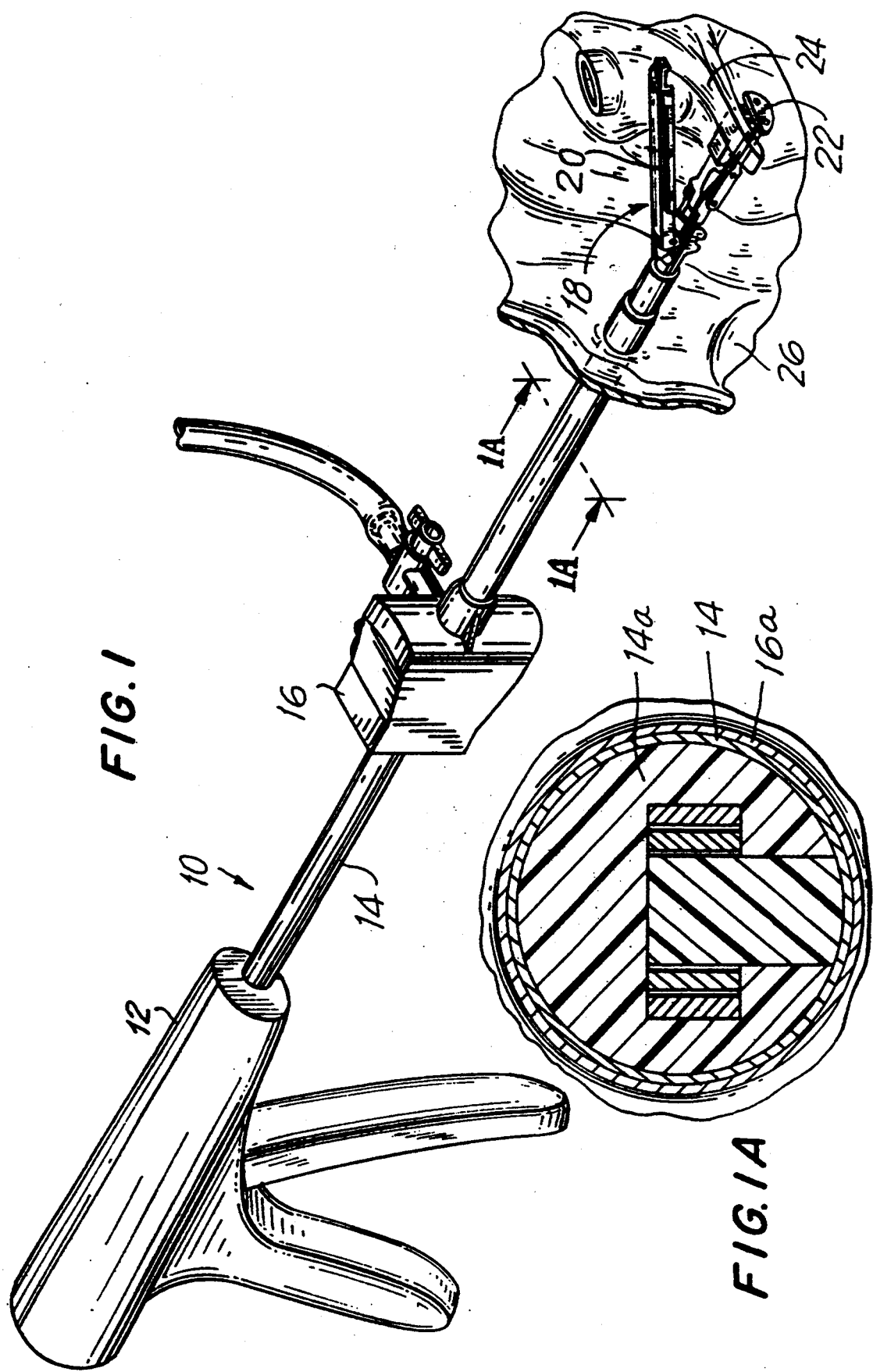
FIG. 1 is a perspective view of the apparatus for endoscopic application of two-part surgical fasteners in accordance with the subject invention.

The surgical apparatus of the subject invention is illustrated in FIG. 1 and is designated generally by reference numeral 10. Apparatus 10 basically comprises a handle portion 12, an elongated endoscopic portion 14 dimensioned for passage through a cannula assembly 16 and a fastener applying assembly 18 having a pair of cooperating arms 20 and 22 for effectuating application of a two-part surgical fastener to body tissue 24 within a body cavity 26 of a patient.

The preferred two-part surgical fastener is composed of a bioabsorbable polymeric material although both bioabsorbable and non-bioabsorbable materials can be utilized. Examples of bioabsorbable material include homopolymers or copolymers of lactide, glycolide, polydioxanone, trimethylene carbonate, polyethylene oxide or other bioabsorbable polymer materials or blends of these respective copolymers. One preferred material is made of a copolymer of lactide and glycolide made from approximately 25% m glycolide and 75% m lactide blended with a homopolymer of glycolide so the total composition is composed of approximately 42% glycolide. Other bioabsorbable resinous materials for constructing such fasteners are disclosed in U.S. Pat. Nos. 4,523,591 and 4,744,365 to Kaplan et al., both of which are herein incorporated by reference. Clearly, other bioabsorbable materials can be utilized. Non-bioabsorbable materials contemplated include any implantable material such as polyester, polypropylene, or polyethylene.

Figure 2:
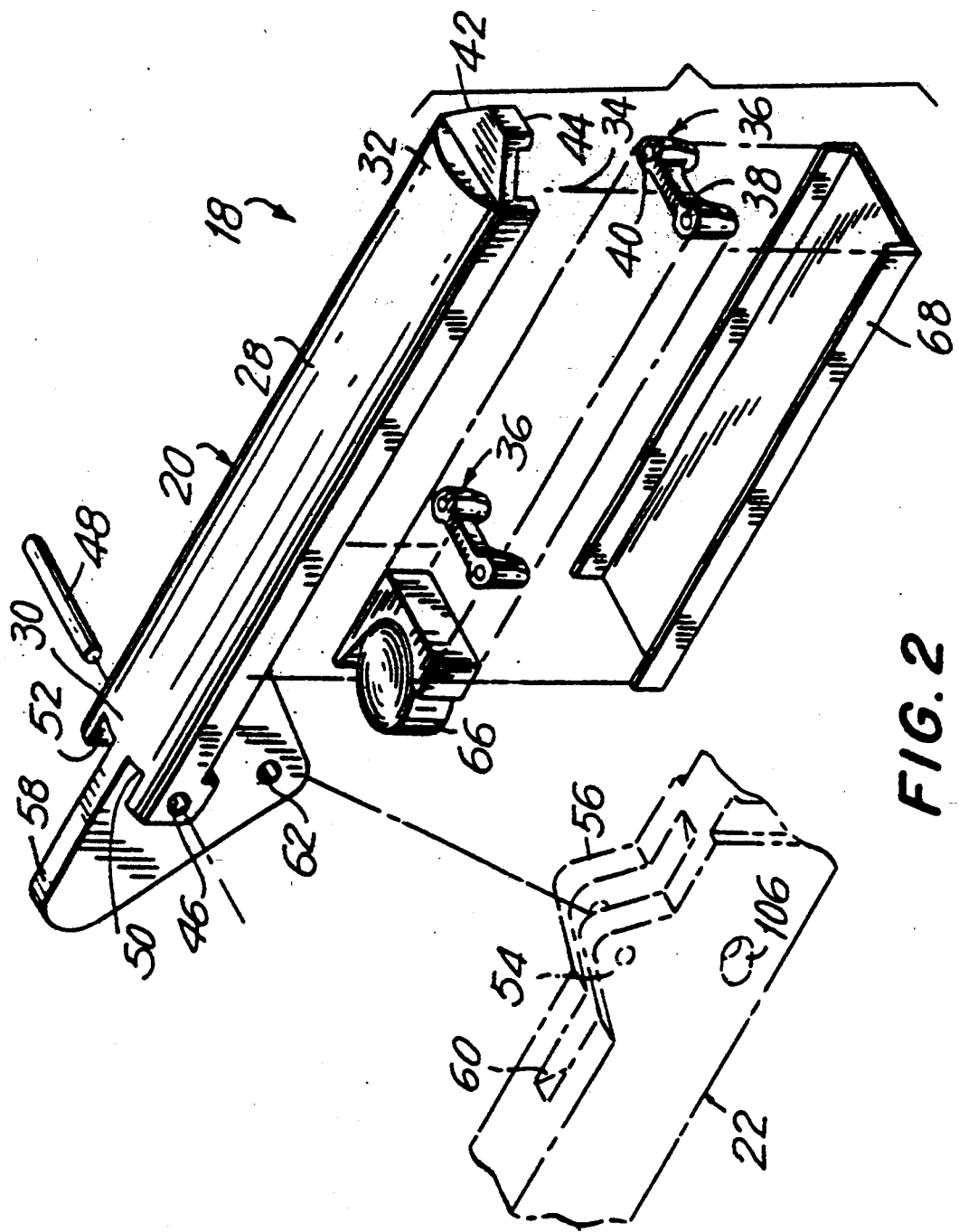
FIG. 2 is a perspective view with parts separated for convenience of illustration, of the retainer supporting portion of the apparatus of FIG. 1.

Referring now to FIGS. 2 and 7, the upper arm 20 of fastener applying assembly 18 has an elongated retainer supporting portion 28 having opposed proximal and distal ends 30 and 32. A substantially rectangular channel 34 is formed within the retainer supporting portion 28 for maintaining and feeding a plurality of retainers 36 which make-up half of the two-part surgical fastener which the apparatus 10 of the subject invention is designed to apply. The rectangular channel is configured and dimensioned to support, contain and feed retainers in the longitudinal direction along the channel. This is accomplished through the justification of the four outside surfaces 36a, 36b, 36c and 36d as shown in FIGS. 5 and 6. Each of the retainers 36 have spaced apart apertures 38 and 40 structured for engaged reception of the corresponding pronged legs of the fastener. A securement portion 42 with a down-turned lip 44 extends outwardly from the distal end 32 of the retainer supporting portion 28 of upper arm 20 for stabilizing the distalmost retainer 36 as well as locating the retainer relative to the distalmost fastener member. A mounting aperture 46 is provided in the proximal end 30 of retainer supporting portion 28 of arm 20 for receiving a pivot pin 48. Insert grooves 50 and 52 are defined in the proximal end 30 of retainer supporting portion 28 for cooperating with corresponding upstanding mounting struts 54 and 56 formed on the lower driving arm 22.

Figure 3:
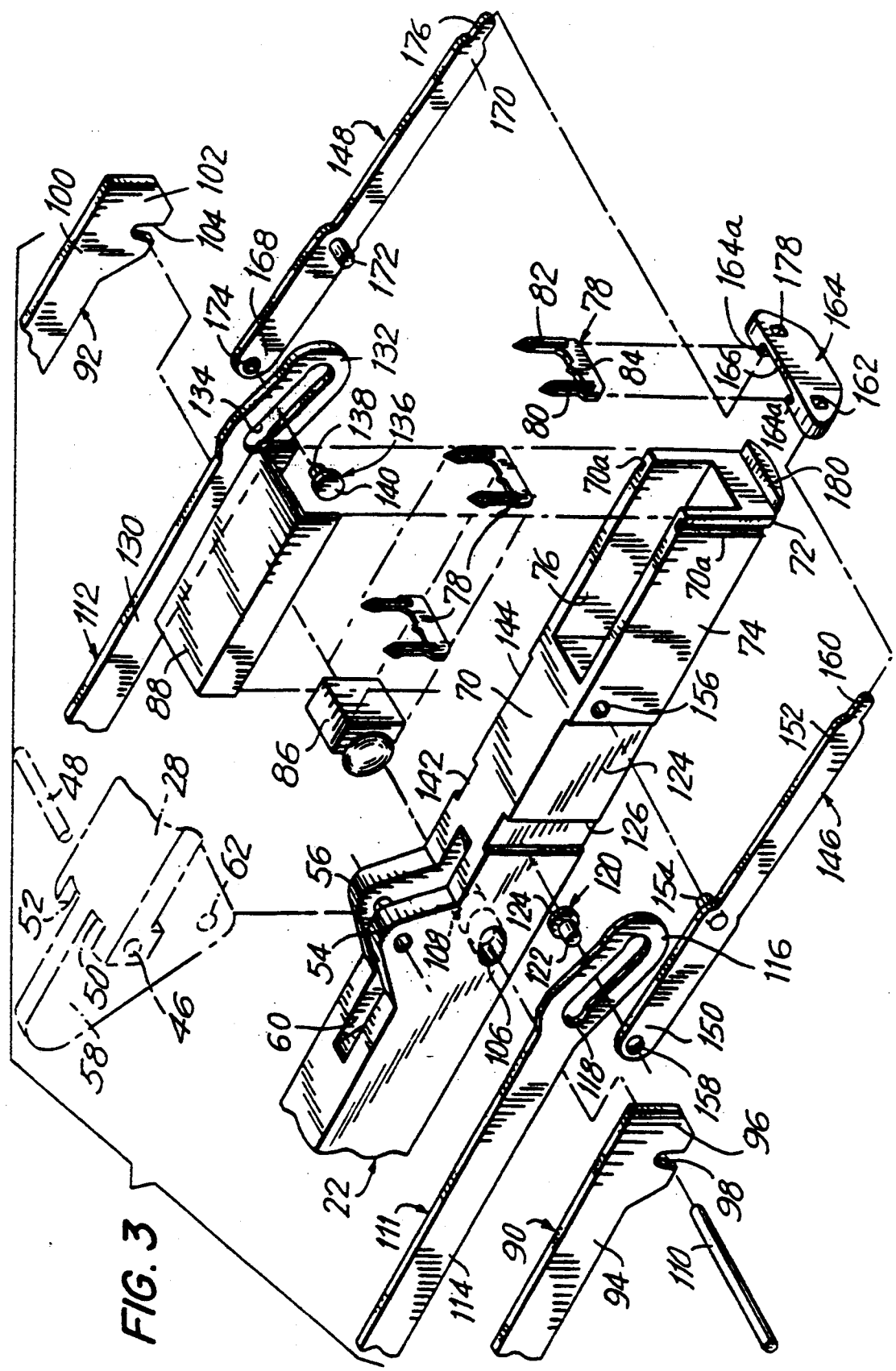
FIG. 3 is a perspective view with parts separated for convenience of illustration, of the fastener supporting portion of the apparatus of FIG. 1.

As shown in FIGS. 3 and 5, guide flange 58 extends from the proximal end 30 of retainer supporting portion 28 for cooperating with a longitudinal guide slot 60 formed in lower driving arm 22. An aperture 62 is provided in guide flange 58 for permitting cooperation of the upper arm 20 and the lower arm 22. This cooperation will be discussed further hereinbelow. A spring loaded biasing member 66 is disposed within the rectangular channel 34 of retainer supporting portion 28 for biasing a plurality of retainers members 36 toward the distal end 32 of retainer supporting portion 28. Biasing system 66 is adapted for uniform plunger-like translation along the longitudinal axis of the elongated driving arm 20 within channel 34 and operates through a coiled spring mechanism (shown schematically) to bias the retainers in the distal direction. An elongated cover plate 68 is provided for mounting to the retainer supporting portion 28 of arm 20 adjacent channel 34 for maintaining the retainer 36 and the biasing member 66 in channel 34.

Referring to FIGS. 3 and 8, the lower driving arm 20 of the surgical fastener applying assembly 18 includes a body portion 70 having a distal end 72. A fastener supporting portion 74 is defined adjacent the distal end 72 of body portion 70 and is provided with a substantially rectangular channel 76 for maintaining and feeding a plurality of fastener members 78 which make-up the second half of the two-part surgical fastener contemplated for application by the apparatus 10 of the subject invention. The rectangular channel is configured and dimensioned to support, contain, and feed subsequent fastener members along the longitudinal axis of the channel. This is accomplished through the justification of the four outside surfaces 78a (side), 78b (bottom), 78c (side), and 78d (distal) of the fastener members as best shown in FIGS. 5 and 6.

Each of the fastener members 78 include two prongs 80 and 82 extending from a backspan 84. Prongs 80 and 82 are adapted for engagement within the spaced apart aperture areas 38 and 40 of retainer 36. A biasing member 86 is disposed within the proximal end of channel 76 for uniformly urging the plurality of fastener portions 78 in plunger-like fashion toward the distal end 72 of body portion 70 and operates through a known coiled spring mechanism, the details of which are not shown. An elongated cover member 88 is provided for mounting adjacent channel 76 so as to maintain fasteners 78 and biasing member 86 within channel 76.

The surgical apparatus 10 further comprises a mechanism for approximating the upper arm 20 toward the lower arm 22 during surgical procedures. The approximating mechanism comprises a pair of elongated draw bars 90 and 92 which are disposed on either side of lower arm 22 and which are operatively connected to the handle portion 12 through endoscopic portion 14. Draw bar 90 has an elongated body portion 94 and a distal head portion 96 depending from body portion 94 which is provided with an inverted U-shaped notch 98. Similarly, draw bar 92 has an elongated body portion 100 having a distal head portion 102 which depends therefrom and which is provided with an inverted U-shaped notch 104. The approximating mechanism further includes a pair of opposed clearance grooves 106 and 108 which are defined in the body portion 70 of lower arm 22. Clearance grooves 106 and 108 each approximately describe an arc whose center of rotation is the pivot 48 of upper arm 20. An elongated pin 110 extends through clearance grooves 106 and 108 and aperture 62 in the guide flange of upper arm 20, and is engaged in the inverted U-shaped notches 98 and 104 in draw bars 90 and 92, respectively. Longitudinal movement of draw bars 90 and 92 will cause corresponding translation of the pin 110 within clearance grooves 106 and 108. This movement causes corresponding approximating movement of the upper arm 20 relative to the lower arm 22.

Another mechanism for effectuating the approximation of the upper arm 20 toward the lower arm 22 of fastener applying assembly 18 is also envisioned which comprises a flexible draw cable extending operatively from handle assembly 12, through endoscopic portion 14, to upper arm 20 (see generally FIG. 50). This mechanism will be discussed in greater detail hereinbelow.

With continued reference to FIG. 3, the surgical apparatus 10 of the subject invention further includes a mechanism for driving at least one of the plurality of fastener members 78 into engagement with at least one of the retainer members 36 of the two-part surgical fastener, for fastening tissue during a surgical procedure. It is envisioned however, that this mechanism may be configured in such a manner so as to simultaneously drive a predetermined number of fastener members 78 into engagement with a predetermined number of retainers 36. The driving mechanism comprises a linkage assembly including a pair of elongated camming arms 111 and 112 disposed on either side of the body portion 70 of lower arm 22. Camming arms 111 and 112 are operatively connected to the handle portion 12 of the apparatus 10 through endoscopic portion 14 in a manner which will be discussed in greater detail hereinbelow. Camming arm 111 includes an elongated body portion 114 and a head portion 116 which depends angularly from the elongated body portion 114. A camming slot 118 is defined in the head portion 116 for accommodating translation of the camming arm 111 relative to a cam follower 120. More particularly, the cam follower 120 has a head portion 122 which cooperates with the cam slot 118, and a tail portion 124 adapted for linear movement within a transverse clearance track 126 formed in side wall 128 of body portion 70.

Similarly, camming arm 112 has an elongated body portion 130 and a head portion 132 which depends angularly from the body portion 130. A camming slot 134 is defined in the head portion 132 for permitting translation of camming arm 112 relative to a cam follower 136 having a head portion 138 which cooperates with camming slot 134, and a tail portion 140 adapted for linear movement within a transverse clearance track 142 formed in side wall 144 of body portion 70. The driving mechanism further comprises a pair of elongated pivoting rocker arms 146 and 148. Rocker arm 146 has opposed proximal and distal ends 150 and 152 and is pivotably connected to the body portion 70 of lower driving arm 22 by an integral pivot pin 154 which is mountable within an aperture 156 provided in body portion 70. An aperture 158 is provided at the proximal end 150 of rocker arm 146 for engagement with the head portion 122 of cam follower 120. This connection, links the rocker arm 146 with the camming arm 111. An outwardly extending prong 160 is provided at the distal end 152 of rocker arm 146. Prong 160 is engagable within a receiving aperture 162 formed in a lift member 164.

As shown in FIG. 3, lift member 164 is provided with inwardly extending rails 164a which are slidable for up and down movement within grooves 70a in body portion 70. The rails 164a and grooves 70a facilitate steady upward and downward movement for lift member 164 to provide accurate alignment of fastener member 78 with corresponding retainer 36 as will be described.

As shown in FIG. 4, lift member 164 has a groove 166 formed therein (see also FIG. 11) for receiving and locating the distalmost fastener member 78 from channel 76 relative to the distalmost retainer. This groove also retains the distalmost fastener member and prevents longitudinal and lateral motion during its insertion into the retainer. Rocker arm 148 has opposed proximal and distal ends 168 and 170 and is pivotably mounted to body portion 70 of lower driving arm 22 by an integral pivot pin 172 disposed intermediate proximal and distal ends 168 and 170 thereof. An aperture 174 is provided in the proximal end 168 of rocker arm 148 for engaging the head portion 138 of cam follower 136 to interconnect rocker arm 148 with camming arm 112. A prong 176 extends outwardly from the distal end 170 of rocker arm 148 for engagement in a receiving aperture 178 provided in lift member 164. A positioning stop 180 extends outwardly from the distal end 72 of body portion 70 for locating the lift member 164 of the driving mechanism.

In operation, once the fastener applying assembly 18 of the surgical apparatus 10 of the subject invention has been extended into the body cavity 26 as illustrated in FIG. 1, the upper arm 20 of assembly 18 may be moved into an open position, best seen in FIG. 4. In this open position, the elongated push rod 90 of the approximating mechanism is in its distalmost position resulting in the camming pin 110 being maintained in a distal area of the clearance groove 106. By maintaining the camming pin 110 in this manner, the upper arm 20 is supported in an upright position which is desirable to receive tissue between the cooperating arms 20 and 22 of the fastener applying assembly 18. Furthermore, when in this non-operative tissue receiving position, the fastener driving mechanism of the apparatus 10 is in a neutral condition wherein the angled head portion 116 of cam arm 11 is in its distalmost position. Consequently, the cam follower 120 is positioned in the most proximal area of the cam slot 118 of head portion 116, while at the same time being disposed in its highest position within the transverse clearance track 126 formed in body portion 70 of lower arm 22. Thereupon, the distal end 152 of the pivoting rocker arm 146 is in its lowest position at the distal end 72 of the lower arm 22. While in this lowest position, the lift member 164, which is secured to the prong 160 at the distal end 152 of rocker arm 146 is supported upon the positioning stop 180 which extends outwardly from the distal end 72 of body portion 70.

Turning to FIG. 5, once tissue has been disposed between the cooperating arms 20 and 22, the upper arm 20 may be approximated toward the lower arm 22, closing the gap therebetween, until such time as the axes of each arm are substantially parallel to one another thereby retaining the tissue therebetween. The approximation of arm 20 is achieved through manipulating the handle portion 12 of the apparatus 10 in such a manner so as to pull the elongated draw bar 90 in a proximal direction causing camming pin 110 to move into a proximal area of the angularly oriented clearance groove 106. Once arm 20 has been approximated, the distalmost retainer 36 of the two-part surgical fastener is in a position for receiving the distalmost fastener member 78 of the two-part surgical fastener, as best seen in FIGS. 6-8. More particularly, the backspan 84 of the distalmost fastener member 78 is supported and aligned within groove 166 formed in the lift member 164. At the same time, the distalmost retainer 36 is secured in a receiving position by the down-turned lip 44 of the securement portion 42 which is disposed at the distal end 32 of upper arm 20 (see FIG. 7).

As best seen in FIG. 1A, the distal portion of endoscopic portion 14 includes internal sealing means 14a which maintains the operative site at positive pressure during the endoscopic or laparoscopic surgical procedure. The sealing means is formed of a compliant impermeable material such as closed-cell foam rubber, natural or synthetic rubber, or a viscous liquid such as silicone grease, for example. The material surrounds the actuating members as shown in FIG. 1A within endoscopic tubular portion 14. Such compliant material forms a gasket seal around the actuating members while still permitting the longitudinal movement of the actuating members through the sealing means with no loss of insufflation pressure past the sealing means.

Referring now to FIGS. 9–11, the handle assembly 12 of the apparatus 10 may be manipulated in a manner which will be described hereinbelow so as to drive the distalmost fastener member 78 toward the distalmost retainer 36 of the two-part surgical fastener. In driving a fastener member, the angled head portion 116 of cam arm 111 is moved in a proximal direction, relative to the cam follower 120. Concomitantly, cam follower 120 translates in a downward direction within the transverse clearance track 126 formed in body portion 70. As a consequence of the camming movement of cam follower 120, the distal end 152 of the rocker arm 146 is moved upwardly, carrying the lift member 164 off of positioning stop 180, and thereupon urging the fastener member 78 toward the retainer 36 of the two-part surgical fastener.

Turning now to FIGS. 12 and 13, to drive the distalmost fastener member 78 into engagement with the distalmost retainer 36, whereby the two prongs 80 and 82 at the end of backspan 84 will be interlocked within the spaced apart aperture areas 38 and 40 of the distalmost retainer 36, the camming arm 111 is moved in such a manner so that the cam follower 120 is positioned in the distalmost area of cam slot 118, and is moved into its lowest position in the transverse track 126 formed in body portion 70. Consequently, the distal end 152 of rocker arm 146 is pivoted into its highest position relative to lower driving arm 22, causing lift member 164 to urge the distalmost fastener member 78 into engagement with the distalmost retainer 36 of the two-part surgical fastener. As the distalmost fastener member 78 engages the distalmost retainer 36 it becomes applied to the target tissue. At this point, the distalmost fastener member 78 will have essentially exited the rectangular channel 76 and is essentially free of the grip of channel 76 of body portion 70. During this process, while the lift member 164 is in the driving position, the body of the lift member withholds the line of fasteners from moving distally under the force of biasing member 86 which normally urges the line of fasteners in the distal direction. As lift member 164 returns to its home position toward positioning stop 180 the proximal wall 164a of lift member 164 engages the distally biased distal-most fastener and urges the entire row of fasteners to move proximally through a short distance. When the lift member 164 returns to its home position on the positioning stop 180 by the reverse sequence of the mechanical operation described, the biasing member 86 in channel 76 of body portion 70 urges the next-in-line fastener member 78 into a driving position. The cooperating arms 20 and 22 of the fastener applying assembly 18 can then open. Since the distalmost fastener member 78 and the distalmost retainer 36 are now locked onto the target tissue, this opening motion will cause the distalmost retainer 36 to be withdrawn from the upper arm 20, passing over the down-turned lip 44. At this point the biasing member 66 in channel 34 of support portion 28 urges the next-in-line retainer 36 into position against the securement portion 42 with down-turned lip 44. This effectively completes the process and the instrument is now ready for the next application of surgical fasteners.

Figure 14:
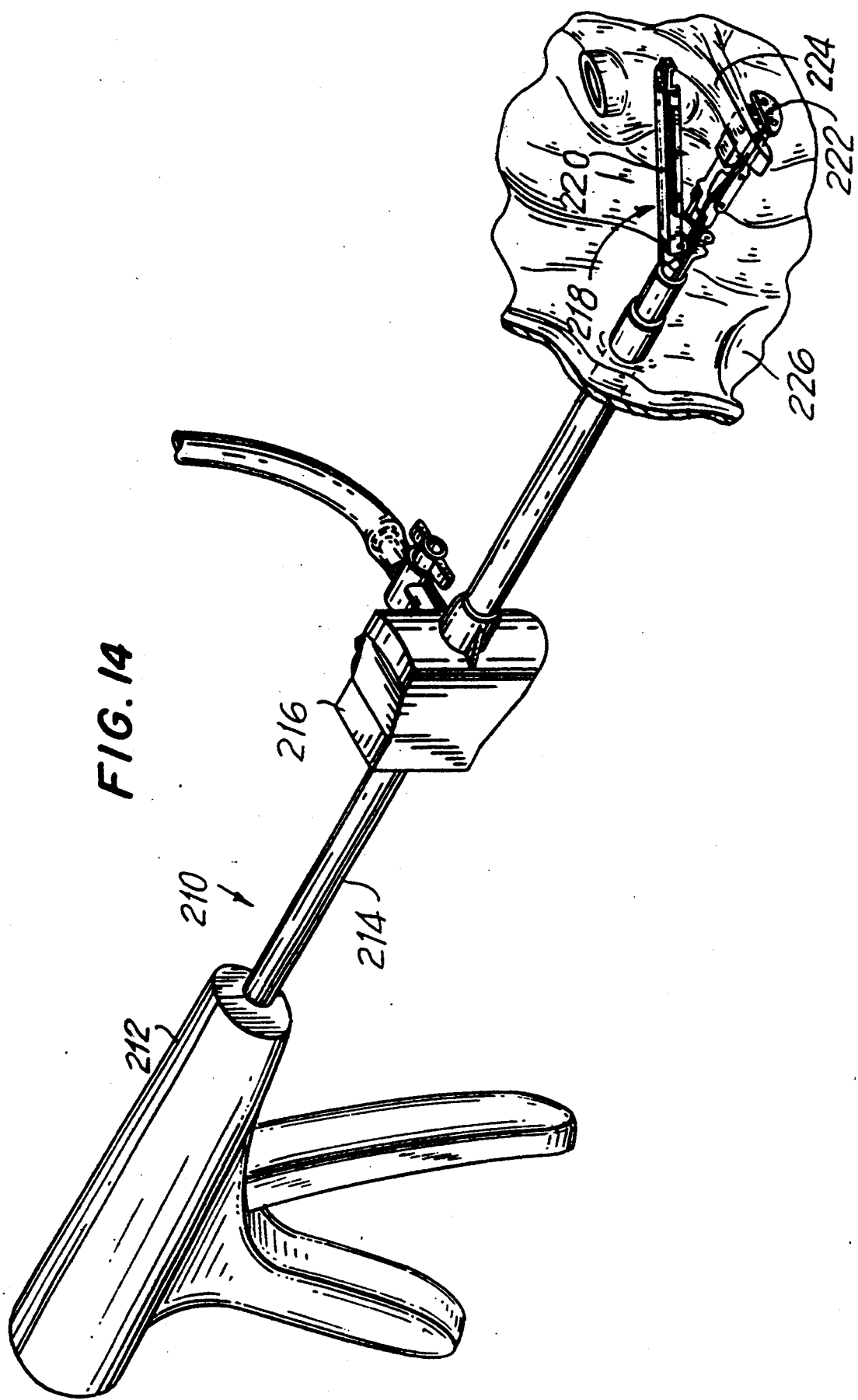
FIG. 14 is a perspective view of an alternative embodiment of the apparatus for endoscopic application of two-part surgical fasteners in accordance with the subject invention.

Referring now to FIG. 14 an alternative embodiment of the inventive apparatus is shown and is designated generally by reference number 210. In the description of this embodiment, similar components and elements are identified by similar numerals as like components which are identified in the previous embodiment. In addition, certain components common to the previous embodiment are illustrated in the drawings but not identified by numerals since they are identical to the corresponding components previously described.

Referring again to FIG. 14, apparatus 210 includes handle portion 212, and elongated endoscopic portion 214 dimensioned for passage through a cannula assembly. A fastener applying assembly 218 is provided at the distal end of endoscopic portion 214 and includes a pair of cooperating arms 220 and 222 for effectuating application of a two-part surgical fastener on tissue 224 within the body cavity 226 of a patient. The structure and operative principles of the embodiment shown in FIG. 14 are substantially identical to those of the previous embodiment discussed hereinabove with the exceptions specifically described in the description which follows.

Figure 15:
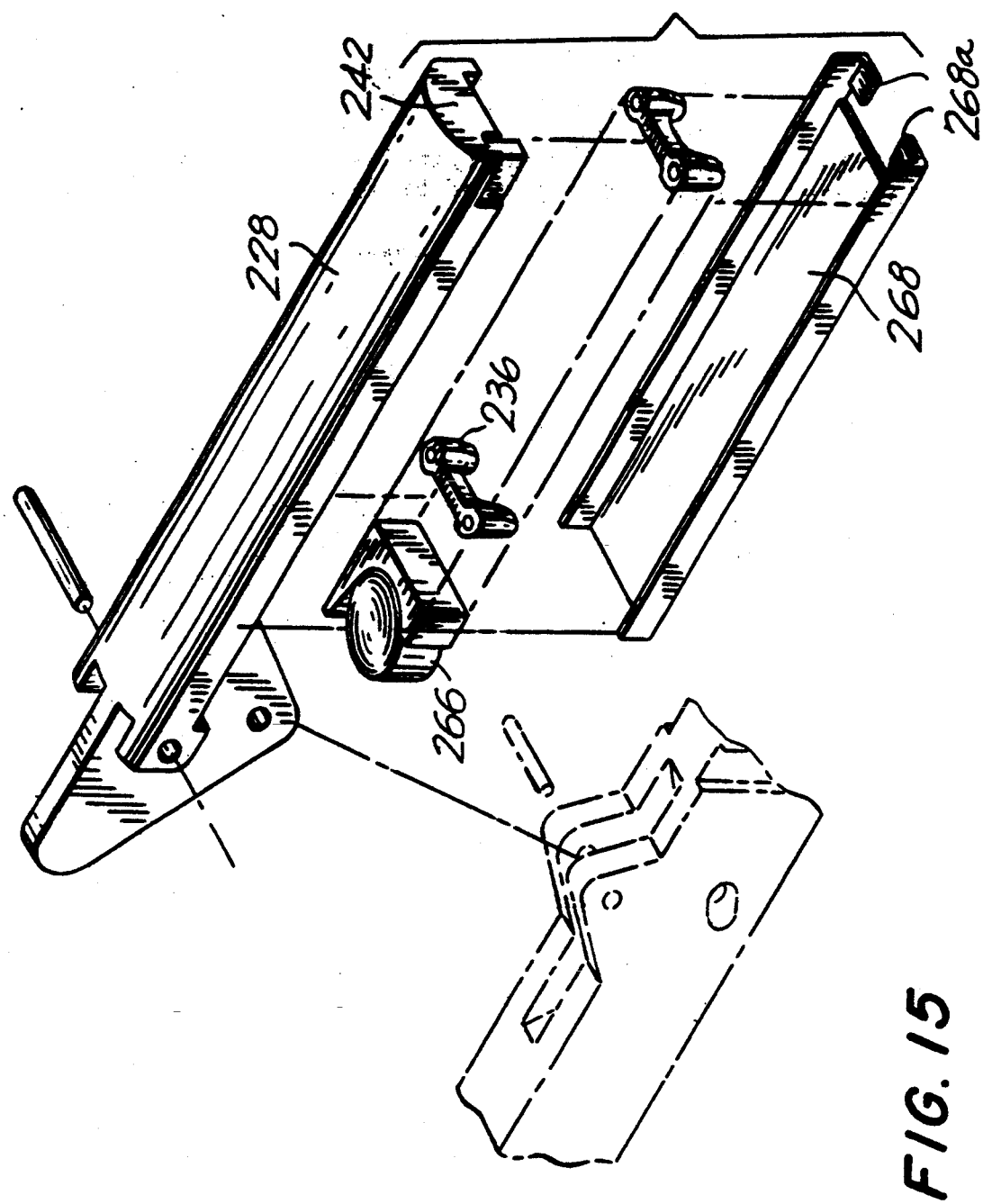
FIG. 15 is a perspective view with parts separated for convenience of illustration, of the retainer supporting portion of the apparatus of FIG. 14.
Figure 17:
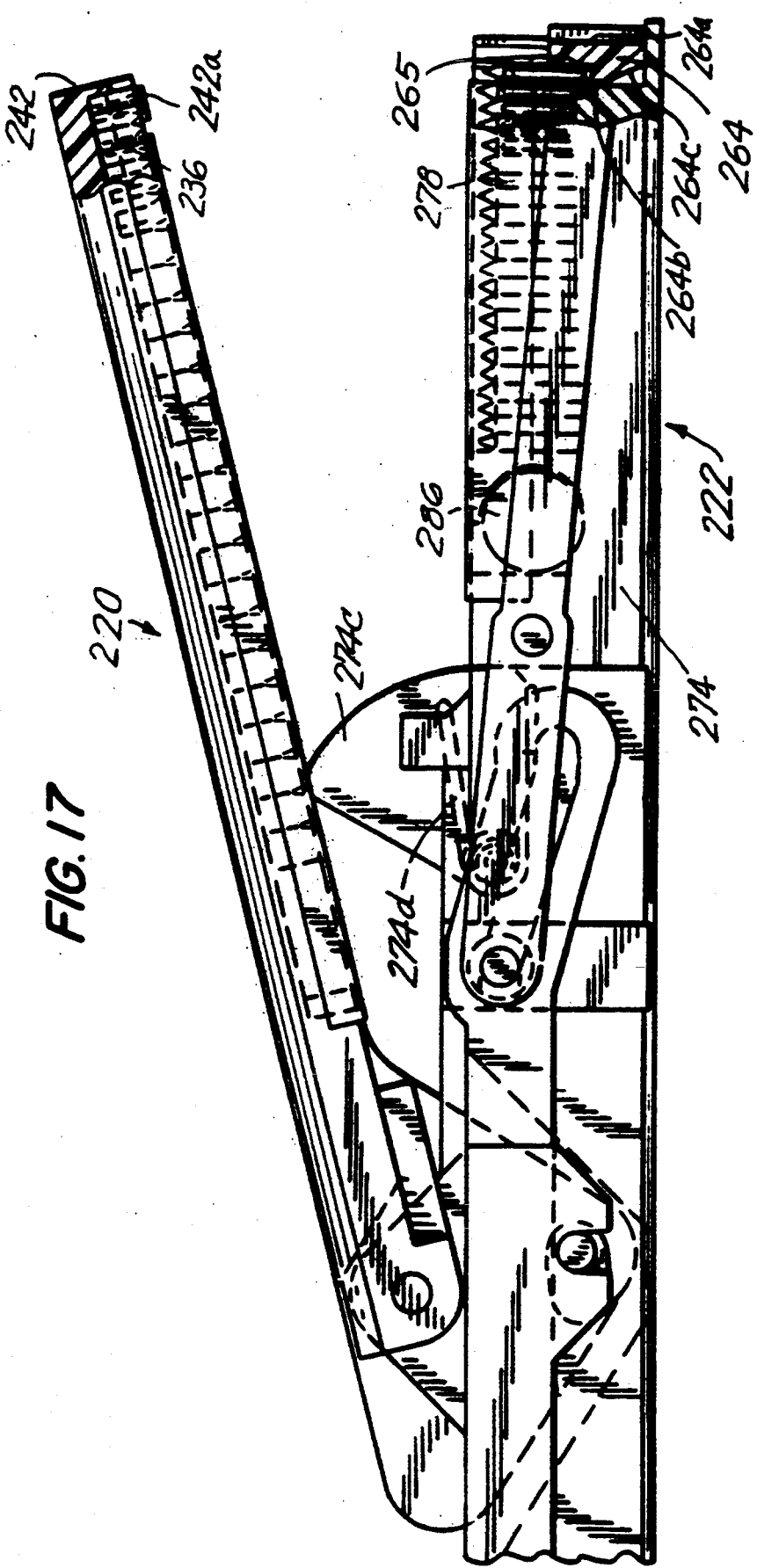
FIG. 17 is a side elevational view of the apparatus of FIG. 14 with the retainer supporting portion in the open position.

Referring to FIG. 15, retainer supporting portion 228 is modified at the distal end by replacing securement portion 42 of the previous embodiment with distal wall 242 to receive and guide retainers 236 as best shown in FIG. 17. The flat inner surface 242a of distal wall 242 as best shown in FIG. 18 provides precise positioning of the distalmost retainer during advancement of the retainer 236 under the bias of resilient member 266. Additionally, the cover plate 268 incorporates two compliant fingers 268a which partially contain the distal-most retainer 236. After insertion of the fastener and opening of the retainer supporting portion 228, these compliant fingers 268a deflect allowing the withdrawal of the distalmost retainer. After insertion of fastener 218 into retainer 236, the retainer moves with the fastener and is thus released by compliant fingers 268a.

Figure 16:
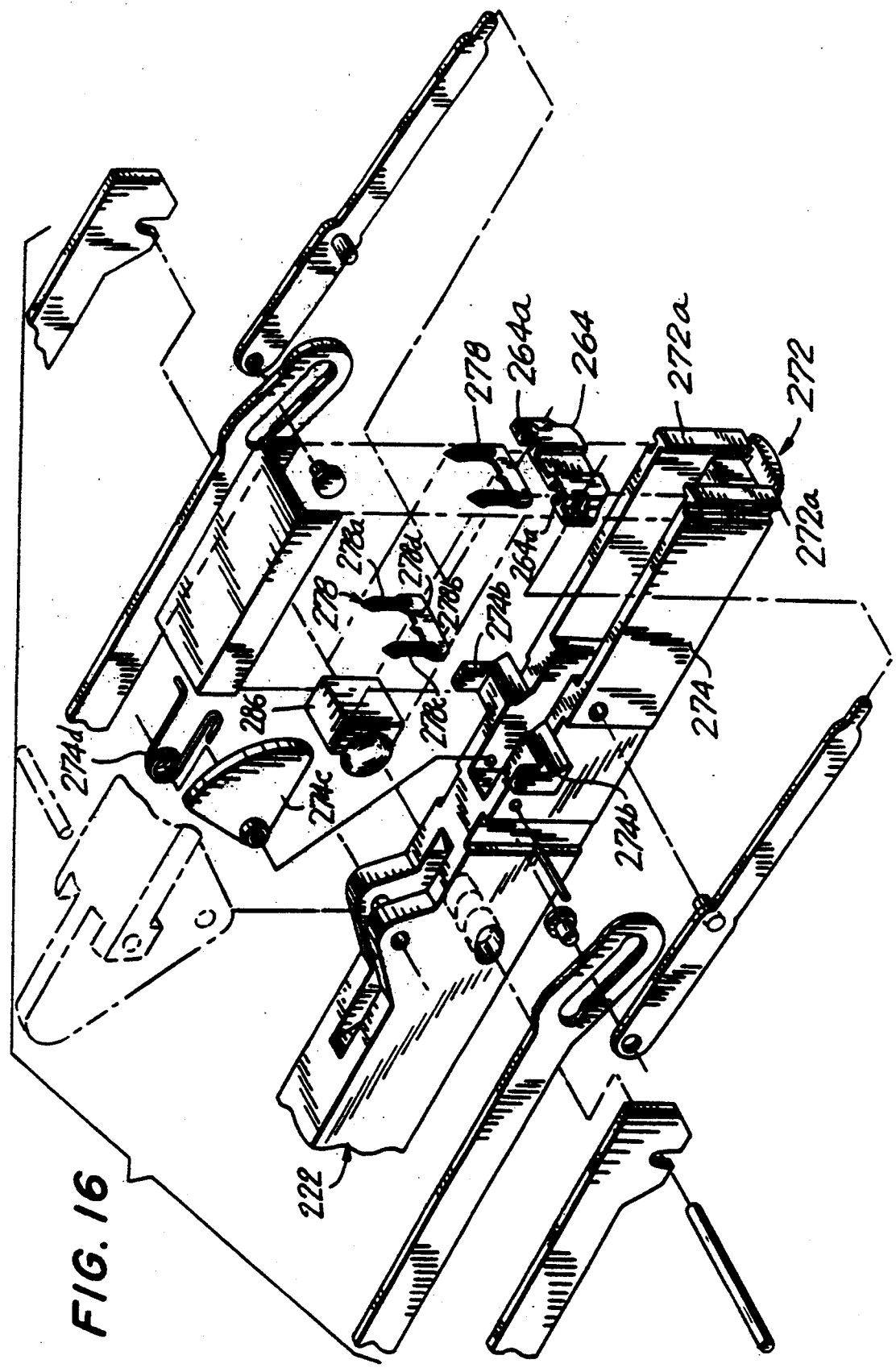
FIG. 16 is a perspective view with parts separated for convenience of illustration, of the fastener supporting portion of the apparatus of FIG. 14.

Referring now to FIG. 16, the fastener supporting portion of the embodiment of FIG. 14 is illustrated. As noted, this embodiment includes components identical to the previous embodiment, except that lift member 164 of the previous embodiment has been replaced by lift member 264 which includes vertical channels 264a configured and dimensioned to slidably receive correspondingly configured and dimensioned rails 272a at the distal end 272 of fastener supporting portion 274. Thus the distalmost fastener 278 is protected and positively positioned in every significant coordinate surface for movement in directions toward and away from the retainer support means 228 of FIG. 15. As can be seen in FIG. 16 the bottom surface 278b is in surface contact with the lift member 264, side surfaces 278a and 278c are in contact with the side walls of lift member 264 and the distal surface 278d is in contact with the proximal wall 264a of lift member 264. When lift member 264 is in position at the distal end of support 274 a positive support surface for fastener 278 is provided by the proximal surface 264a of the lift member 264. This precise positioning of fastener member 278 thus facilitates precise interactive mating of the fastener members 278 and retainers 236 when the lift member 264 is advanced upwardly toward the retainer support means 228 as described in the previous embodiment.

Turning to FIG. 17, lift member 264 includes a groove 265 defined between proximal wall 264a and proximal lip 264b and dimensioned to maintain the precise orientation of fastener 278. Additionally, lift member 264 is configured to include tapered proximal surface 264c which will initially permit the fasteners to move forward a slightly greater distance under bias of resilient member 286 during a fastener lifting process. Thereafter, as lift member 264 is lowered the gradual taper of proximal surface 264c will initially permit the fasteners to move forward a slightly greater distance under bias of resilient member 286. As lift member 264 is lowered further, the gradual taper of proximal surface 264c will contact the fastener next-in-line and provide a slight proximal movement to the row of fasteners as the lift member 264 returns to its home position below the next-in-line fastener. Essentially, the tapered surface permits greater movement to the fasteners during the upward and downward translation of lift member 264.

Referring now to FIG. 16 additional features of the invention are illustrated and include a pair of upstanding locator extensions 274b which engage and surround the retainer support portion 228 when the retainer support portion 228 is closed for firing a fastener. These locator extensions provide stable positioning and positive location of the retainer support portion 228 relative to the fastener support portion 274. In addition, a tissue stop 274c is pivotally positioned with a torsion spring 274d to bias the tissue stop 274c toward the upward position as shown in FIG. 17. One end of spring 274d engages a dip on tissue stop 274c and the other free end is fixedly positioned relative to fastener support 274. When tissue is positioned within the open jaws of fastener applying assembly 218, tissue stop 274c prevents the tissue of the patient from extending inwardly to the hinge area of the apparatus, thus preventing trauma to tissue and unwanted jamming of the instrument, while providing a limit for location of the tissue. When the upper jaw 220 of assembly 218 has been closed for firing the apparatus, tissue stop 274c is pivoted downwardly with upper jaw 220 continuing to prevent tissue damage.

Referring now to FIGS. 20–37, wherein like reference numerals indicate similar structural elements or components, three distinct embodiments of the handle assembly 12 of surgical apparatus 10 are illustrated.

Turning initially to FIGS. 20–24, a first embodiment of the handle assembly of the subject invention is illustrated and is designated generally by reference numeral 400. Handle assembly 400 comprises barrel portion 402, stationary gripping handle 404, and pivoting actuation handle 406 which is pivotably mounted to the barrel portion 402 by pivot pin 405. Handle assembly 400 includes two primary mechanisms for operating the fastener applying apparatus 10 of the subject invention. These include a first mechanism for effectuating the approximation of the upper jaw 20 relative to the lower jaw 22 of the fastener applying assembly 18, and a second mechanism for effectuating the driving of the fastener portion into engagement with the retainer portion of the two-part surgical fastener. Both of these mechanisms are operated through manipulation of the pivoting actuation handle 406. More particularly, manipulation of pivoting handle 406 through a first distance will effectuate jaw approximation, while manipulation of the pivoting handle 406 through a second further distance will effectuate the driving of the fastener portion of the two-part surgical fastener into engagement with the retainer portion thereof.

The first mechanism for effectuating approximation of the jaws includes an approximation cable 408 which extends from handle assembly 400, through the endoscopic portion 14 of the instrument, to the fastener applying assembly 18 at the distal end thereof. The proximal end of cable 408 is fastened to a draw plate 410 which is operatively engaged to an actuation cam 412. Actuation cam 412 is substantially housed within stationary handle 404 of handle assembly 400 and is pivotably connected thereto at a pivot point 414 disposed at the lower end thereof. A plurality of spaced apart coiled springs 415a, 415b, and 415c are associated with actuation cam 412 for biasing actuation cam 412 relative to stationary handle 404.

Locking mechanism 416 is provided for interlocking pivoting handle 406 and actuation cam 412 with respect to each other. By doing so, the jaws of the fastener applying assembly will be maintained in a closed position. It is in this closed position that the instrument is intended to be introduced to the surgical site through the trocar or cannula device as shown, for example, in FIG. 1. Exemplary trocar or cannula devices are disclosed in commonly assigned U.S. Pat. No. 4,943,280 to Lander and U.S. Pat. No. 4,654,030 to Moll, the contents of which are herein incorporated by reference. Locking mechanism 416 includes a catch shelf 418 extending outwardly in a distal direction from actuation cam 412 and a spring-biased over-centered latch 420 pivotably associated with actuation handle 406 and disposed upon a ledge extending rearwardly therefrom.

Figure 21:
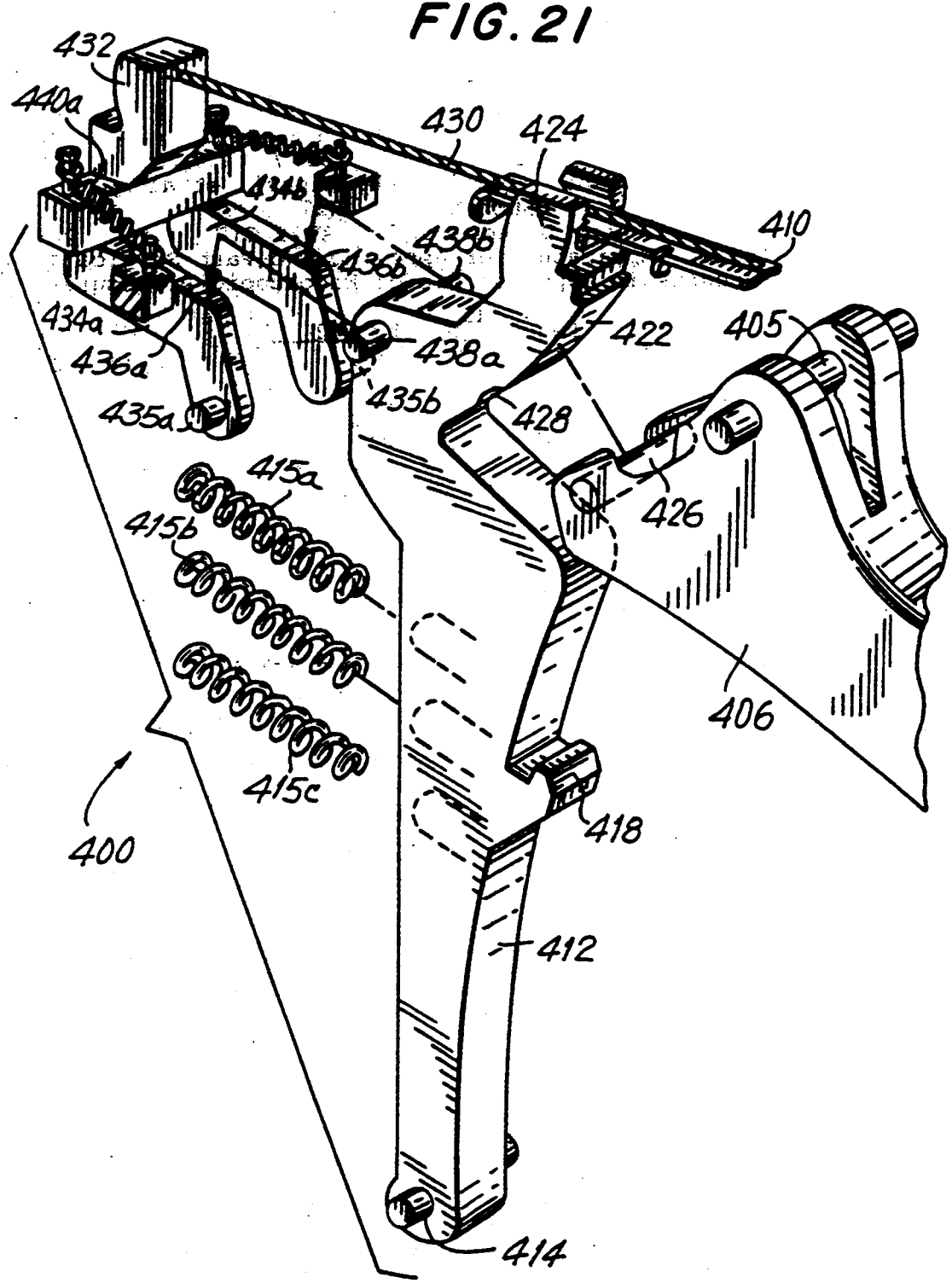
FIG. 21 is a perspective view with parts separated for convenience of illustration, of the handle assembly of FIG. 20.
Figure 22:
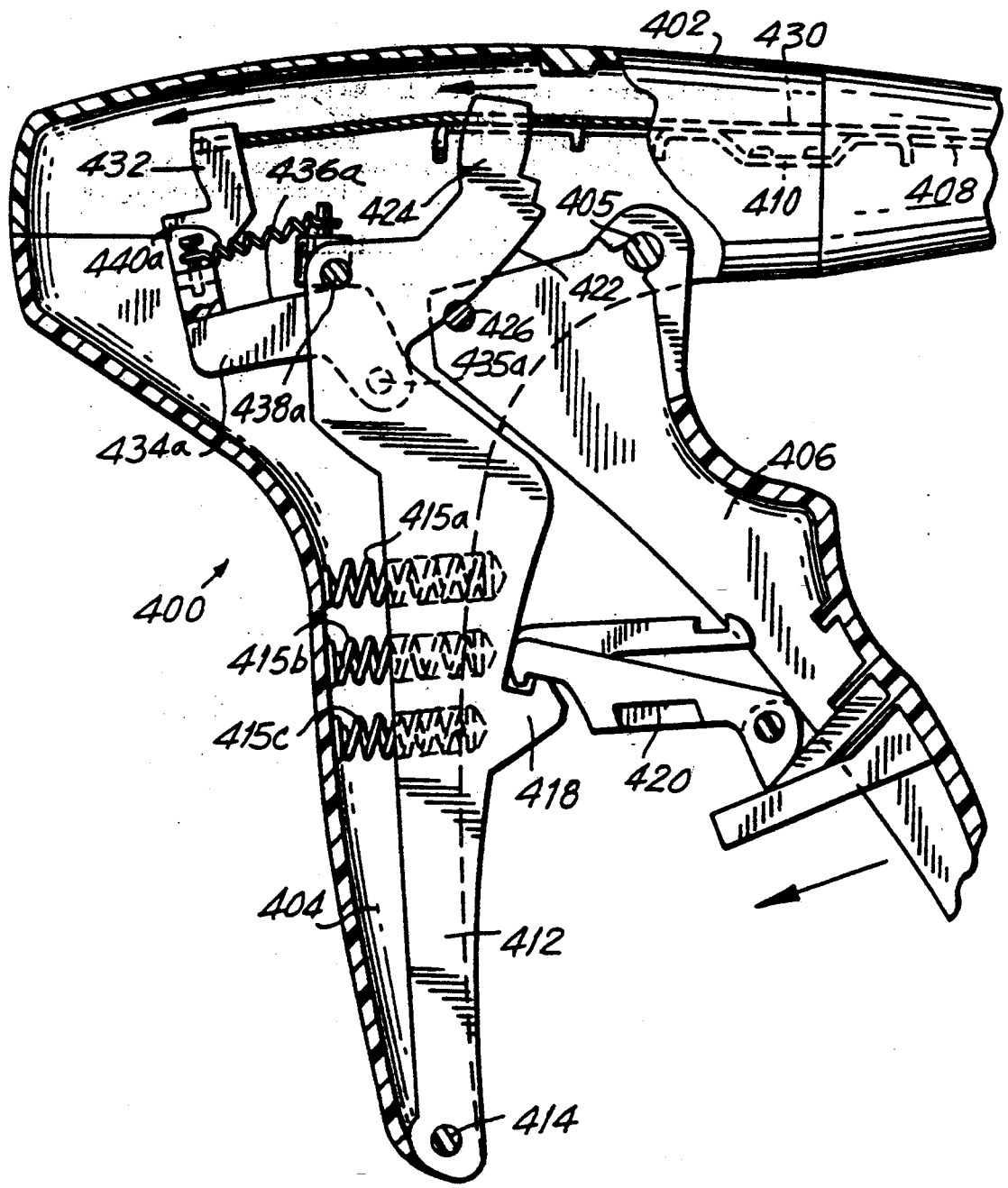
FIG. 22 is a side elevational view in cross-section of the handle assembly of FIG. 20 with the pivoting handle thereof in a partially actuated position.

Turning to FIG. 21, actuation cam 412 defines an arcuate cam surface 422 adjacent the cable mounting area 424 thereof along which a primary cam follower 426 travels to effectuate reciprocating movement of approximation cable 408. Cam follower 426 is formed on the pivoting actuation handle 406 adjacent pivot point 405. A depression area 428 is defined at a point intermediate the path of cam surface 422 for reception of cam follower 426 at a particular point in its translation. Specifically, the position of the depression area 428 corresponds to the position in which the pivoting handle 406 is in when lock mechanism 416 is in its horizontal position. As best seen in FIG. 22, pivotable movement of actuation cam 412 in a counter-clockwise direction about pivot point 414 will thus be effected by translation of cam follower 426 along cam surface 422 by manipulating actuation handle 406 through a first distance.

The second mechanism for effectuating the driving of the fastener portion of the two-part fastener into engagement with the retainer portion thereof is shown in FIG. 20. This mechanism includes a driving cable 430 which extends from handle assembly 400, through endoscopic portion 14, to the linkage mechanism associated with the fastener applying camming arms 111 and 112 of the assembly of the subject invention. A proximal end of driving cable 430 is mounted in a flange portion 432 of dual cam links 434a and 434b. Dual cam links 434a and 434b are pivotably mounted in the barrel portion 402 of handle assembly 400 by pivot pins 435a and 435b and define substantially linear cam surfaces 436a and 436b along which secondary cam followers 438a and 438b travel. Secondary cam followers 438a and 438b are preferably formed integral with actuation cam 412 adjacent the cable mounting area 424 thereof. Coiled springs 440a and 440b are provided for biasing cam links 434a and 434b relative to barrel portion 402.

Figure 23:
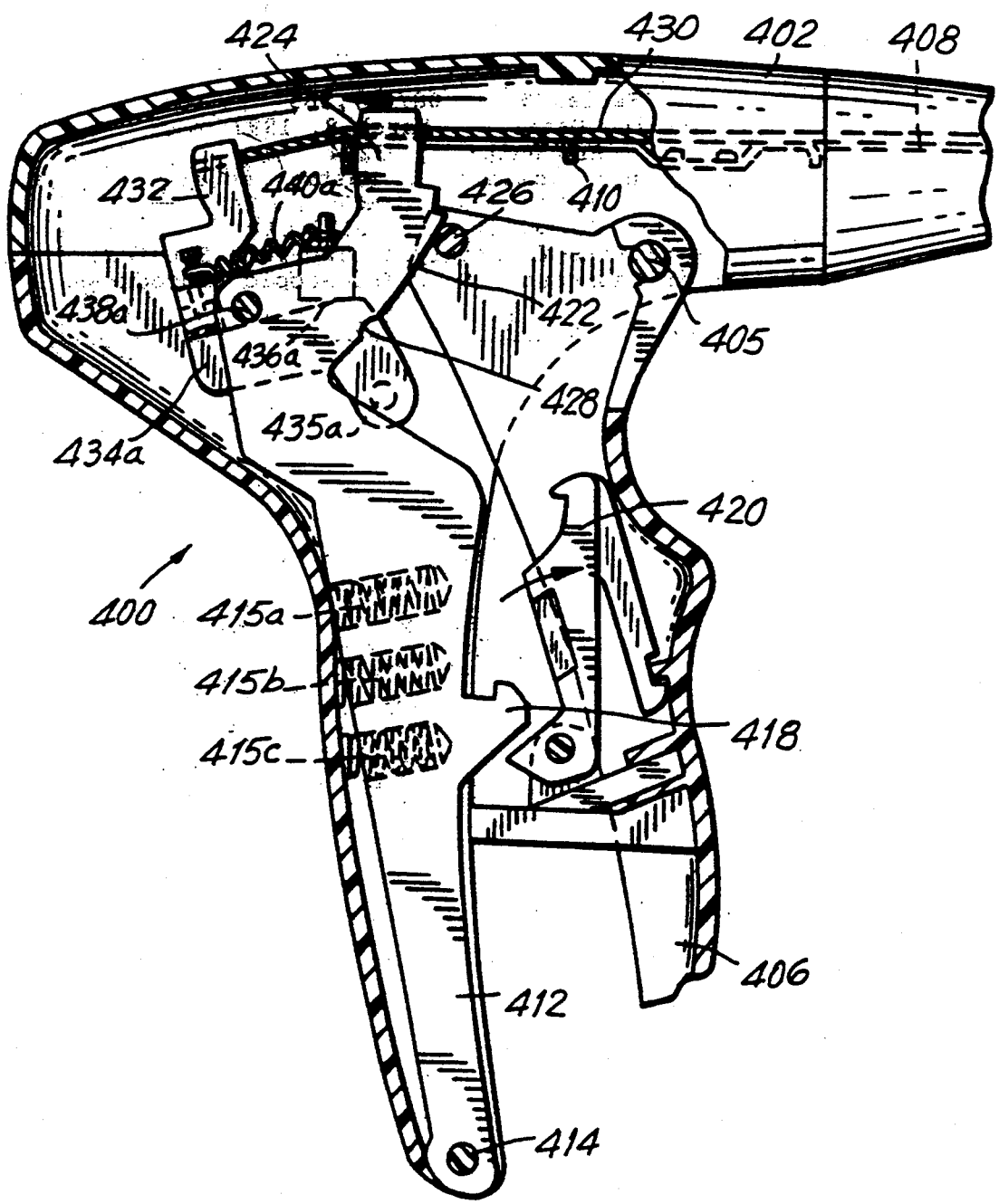
FIG. 23 is a side elevational view in cross-section of the handle assembly of FIG. 20 with the pivoting handle thereof in a fully actuated position.

As best seen in FIG. 23, movement of cam link 434 will be effected by movement of actuation cam 412 in response to manipulation of actuation handle 406 which will cause cam follower 438 to travel along cam surface 436, urging cam link 434 to pivot about pivot point 435, thereby drawing drive cable 430 in a proximal direction.

Referring to FIG. 20A, an alternative embodiment of handle assembly 400 is illustrated which comprises a ratchet mechanism 415 housed within barrel portion 402 for controlling the movement of actuation handle 406. Ratchet mechanism 415 includes a communication beam 415a extending operatively between actuation cam 412 and cam link 434, a gear rack 415b associated with cam link 434, and a spring biased pawl 415c integrated with communication beam 415a for cooperating with gear rack 145b.

In use, as actuation cam 412 rotates in a counter-clockwise direction in response to manipulation of actuation handle 406, communication beam 415 travels proximally within the bore 415d defined in cam link 434. As communication beam 415 translates, it moves relative to gear rack 415b causing pawl 415c to sequentially interengage therewith. The interengagement of pawl 415c with gear rack 415b functions to maintain the position of actuation handle 406 and consequently serves to maintain the position of the actuation mechanisms housed within the barrel portion 402 of handle assembly 400.

Turning now to FIGS. 24–33, a second embodiment of the handle assembly of the surgical apparatus of the subject invention is illustrated and is designated generally by reference numeral 500. Handle assembly 500 is similar to handle assembly 400 in that approximation of the upper and lower jaws of the fastener applying assembly associated therewith, and driving of the fastener portion of the two-part surgical fastener into the retainer portion thereof is effectuated through manipulation of a pivoting actuation handle 506 relative to a stationary handle 504. Handle assembly 500 differs from handle assembly 400 however, in that movement of the actuation cam 512 housed within stationary handle 504 is transmitted to the approximation cable 508 and driving cable 530 by a gear assembly 540 housed within the barrel portion 502 of handle assembly 500. The movement of actuation cam 512 through manipulation of actuation handle 506 is effected by the translation of a cam follower 526 along an arcuate cam path 522 defined on the proximal surface of actuation cam 512. Unlike the actuation cam 412 of handle assembly 400, actuation cam 512 of the present embodiment of the handle assembly pivots in a clockwise direction about pivot point 514 upon manipulation of actuation handle 506.

Figure 25:
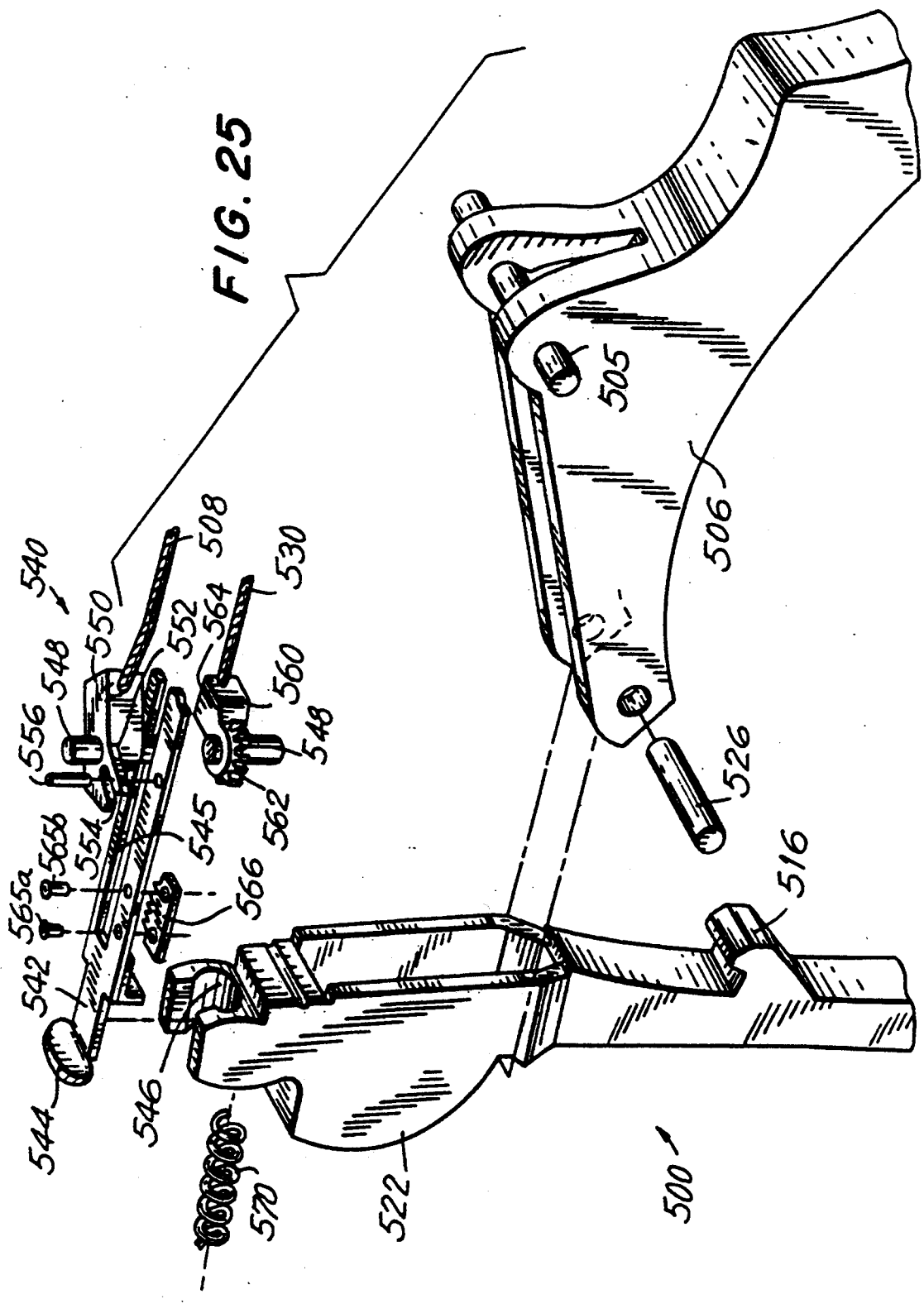
FIG. 25 is a perspective view with parts separated for convenience of illustration, of the handle assembly of FIG. 24.
Figure 26:
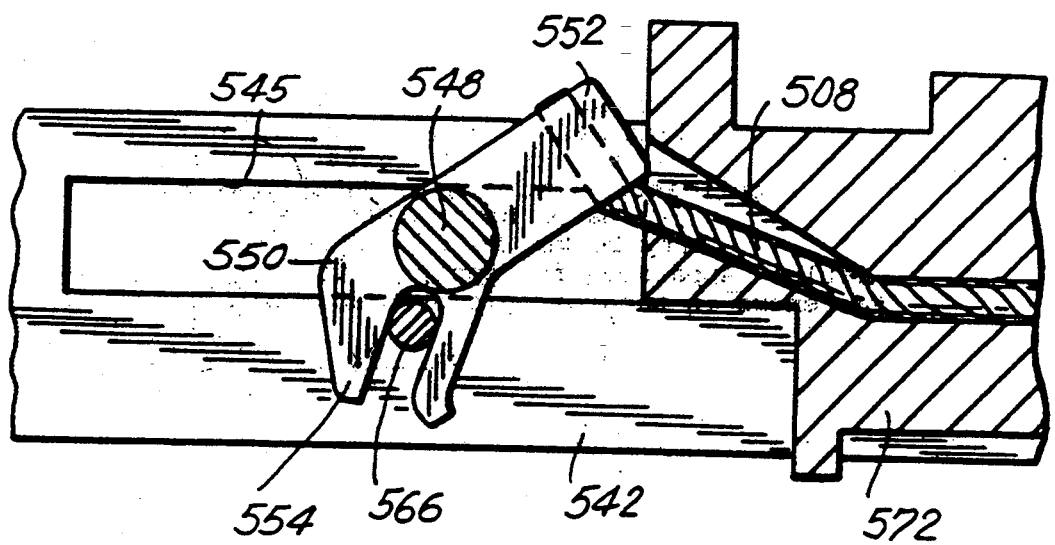
FIG. 26 is a view taken along lines 26—26 of FIG. 24 illustrating the cammed cable drawing mechanism prior to actuation of the handle assembly.

As best seen in FIG. 25, gear assembly 540 comprises a slide plate 542 having a proximal engaging flange 544 dimensioned and configured for engagement within a corresponding mounting port 546 defined in actuation cam 512. Slide plate 542 defines a longitudinal slot 545 for accommodating a transverse post 548 relative to which slide plate 542 translates upon manipulation of actuation handle 506. Gear assembly 540 further comprises a cable crank 550 mounted for pivotal movement about post 548, and having a cable engaging tail 552 for mounting the proximal end of approximation cable 408. Cable crank 550 further includes a forked reception area 554 for receiving a cam pin 556 which depends from slide plate 542. Thus, longitudinal translation of slide plate 542 in a distal direction in response to pivotal movement of actuation cam 512 will cause the depending cam pin 556 to urge cam crank 550 to rotate in a counter-clockwise direction about post 548 from the position of FIG. 26 to the position shown in FIG. 29, thereby causing approximation cable 508 to be drawn in a generally proximal direction for effectuating closure of the jaws of fastener applying assembly of the instrument.

Figure 24:
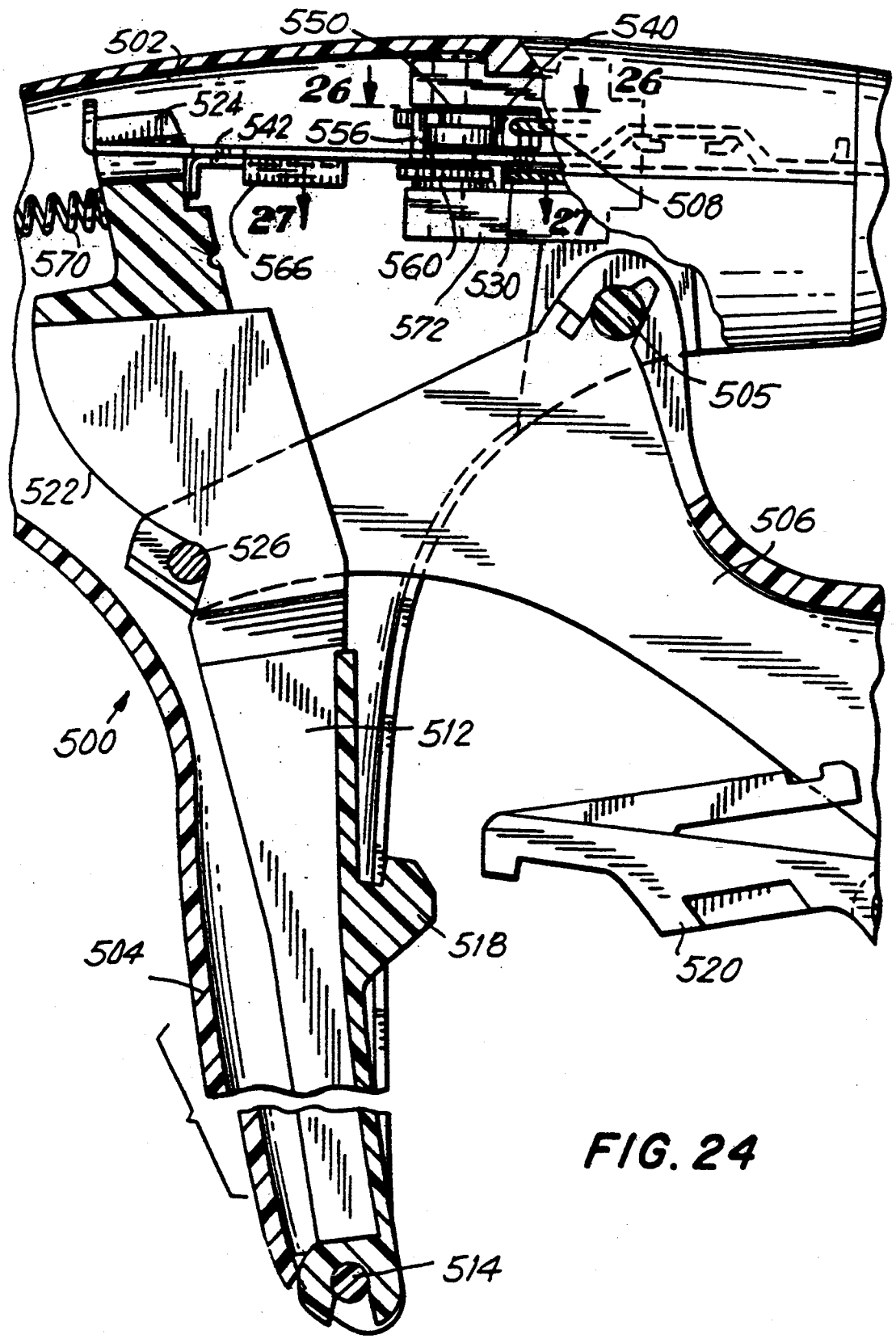
FIG. 24 is a side elevational view in cross-section of a second embodiment of a handle assembly in accordance with the subject invention.
Figure 27:
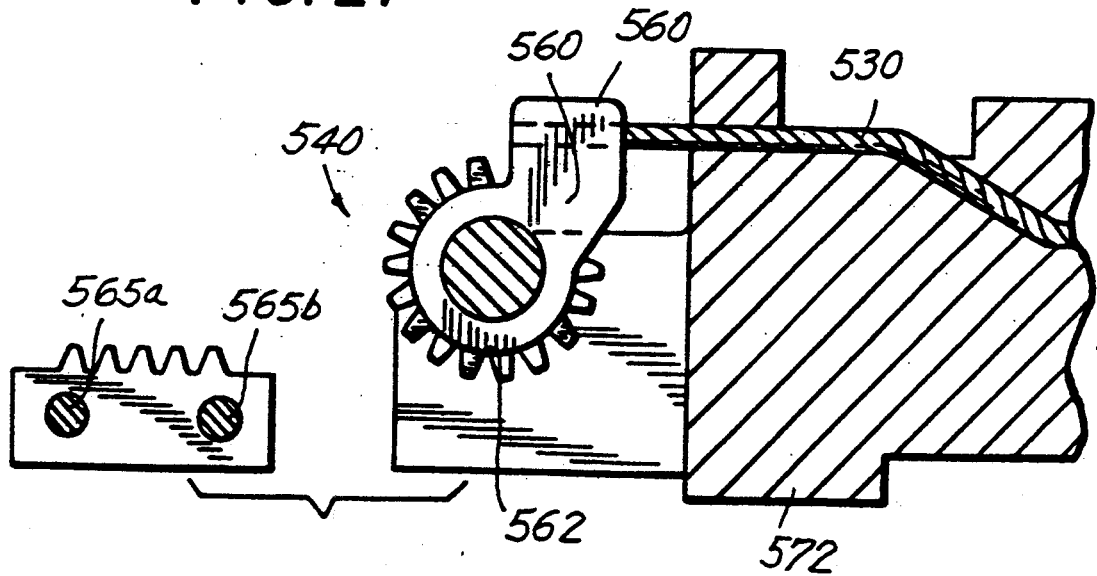
FIG. 27 is a view taken along lines 27—27 of FIG. 24 illustrating the geared cable drawing mechanism of the handle assembly.
Figure 28:
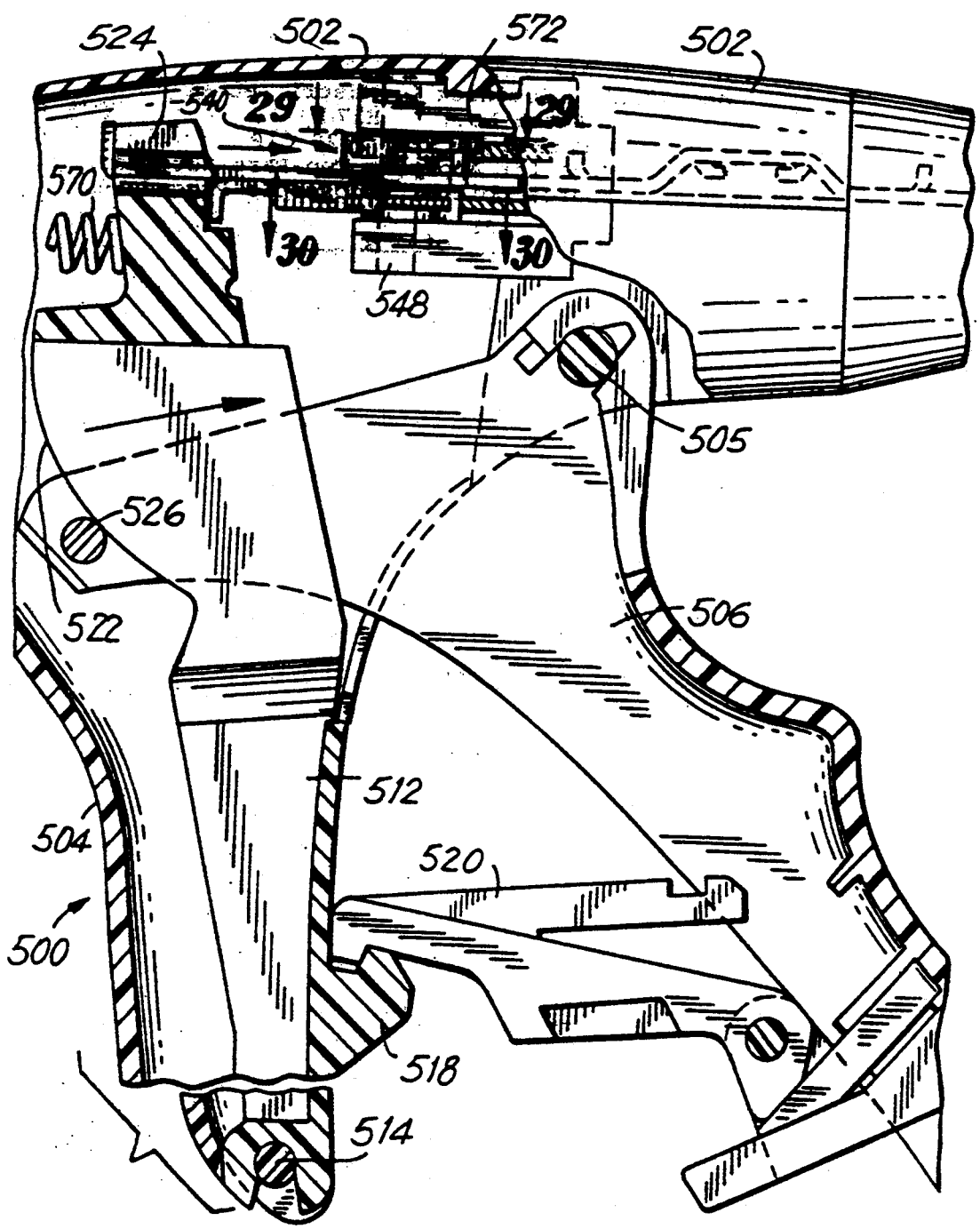
FIG. 28 is a side elevational view of the handle assembly of FIG. 24 with the pivoting handle thereof in a partially actuated position.
Figure 29:
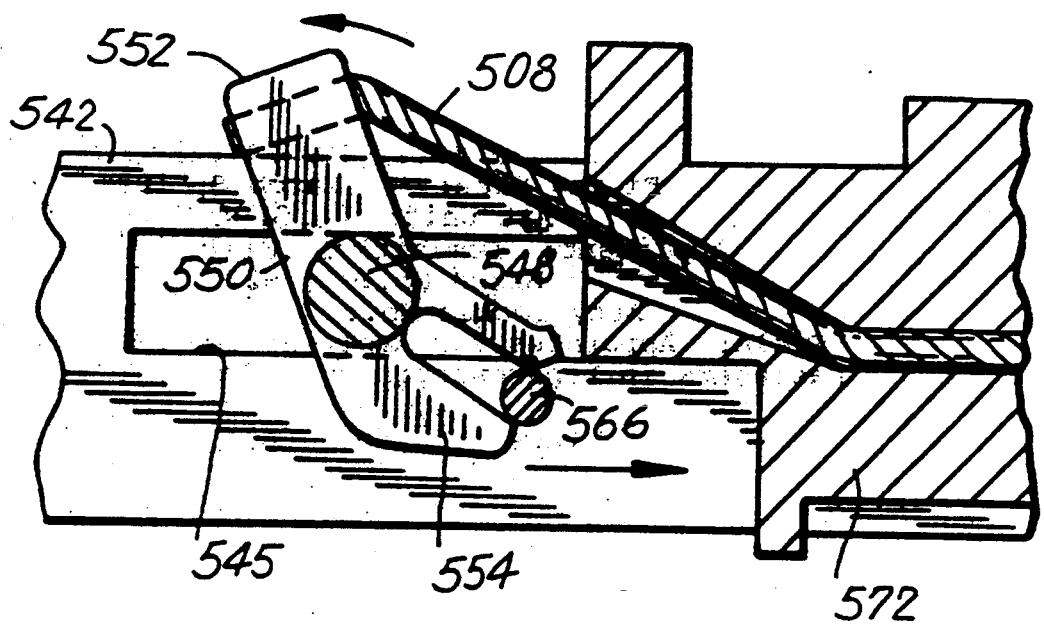
FIG. 29 is a view taken along lines 29—29 of FIG. 28 illustrating the cammed cable drawing mechanism of FIG. 26 in a first cable drawing position.
Figure 30:
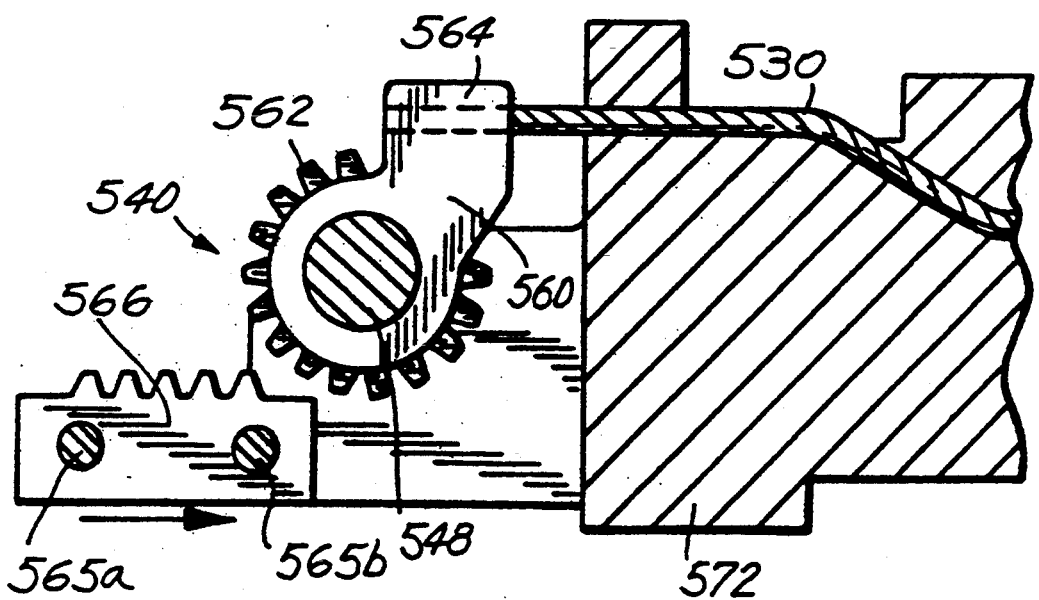
FIG. 30 is a view taken along lines 30—30 of FIG. 28 illustrating the geared cable drawing mechanism of FIG. 27 in a first cable drawing position.

Referring to FIG. 24 in conjunction with FIGS. 27 and 28, gear assembly 540 further comprises a pinion gear 560 having an annular tooth portion 562 and a tail portion 564 for mounting the proximal end of driving cable 530. Pinion gear 560 is also mounted for rotation about post 548. A gear rack 566 is mounted on slide plate 542 by pins 565a and 565b and moves therewith to interact with pinion gear 560 to effectuate the rotation thereof. Thus, distal movement of slide plate 542 in response to movement of actuation cam 512 will urge gear rack 566 to move relative to pinion gear 560 from the position of FIG. 27 through the position shown in FIG. 30, to the position of FIG. 33, causing the counter-clockwise rotation of pinion gear 560 and consequently drawing driving cable 530 in a generally proximal direction to effectuate driving of the fastener portion of two-part surgical fastener into engagement with the retainer portion thereof. A coiled spring 570 is provided for biasing actuation cam 512 relative to the rear wall of barrel portion 502 to effectuate the return thereof following an actuation sequence. A substantially cylindrical sleeve 572 is provided in barrel portion 502 for mounting the gear assembly 540 and for inhibiting entanglement of the motion transmitting cables 508 and 530 as the gear assembly 540 is actuated (see FIG. 24).

Figure 31:
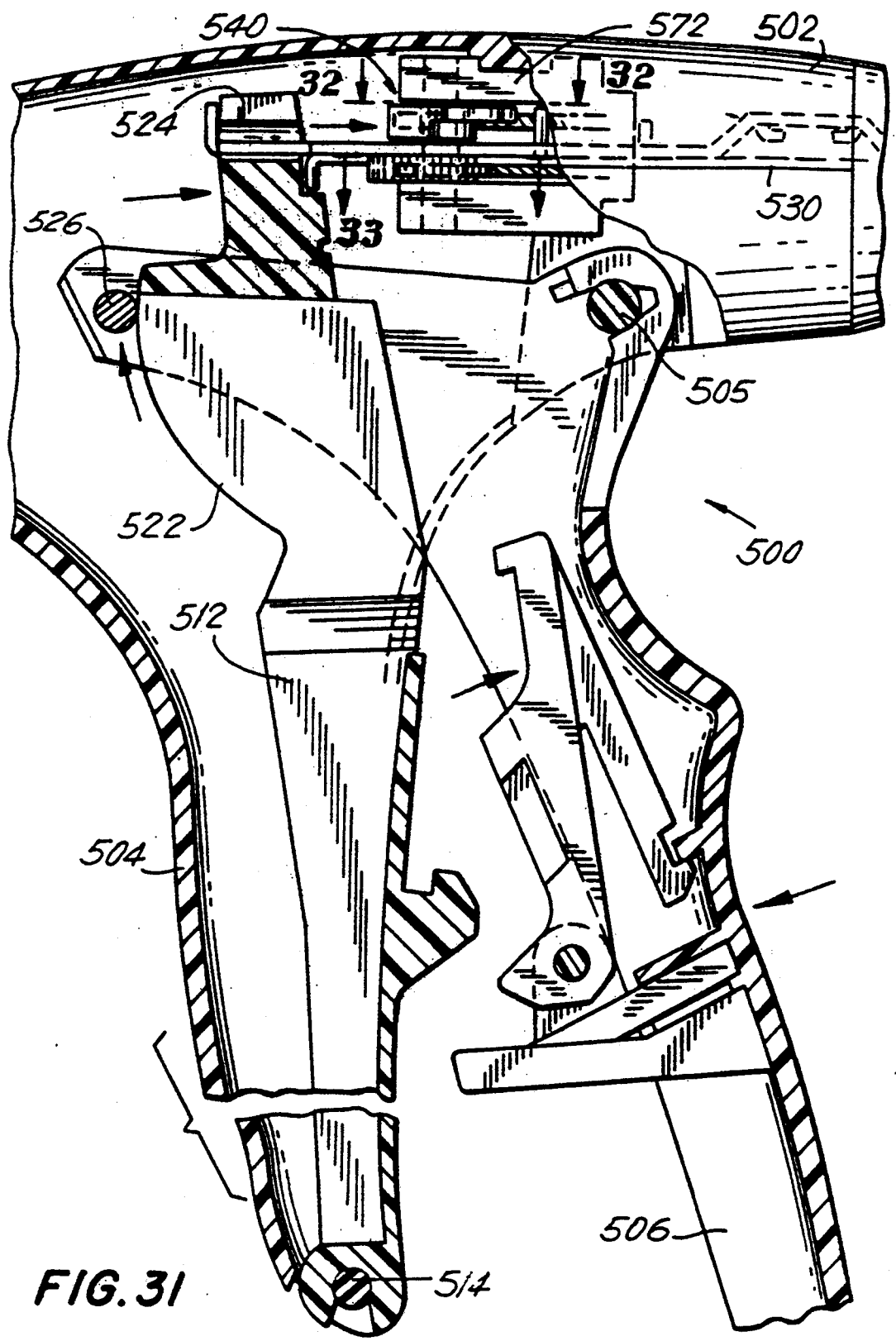
FIG. 31 is a side elevational view, partially in cross-section, of the handle assembly of FIG. 24 with the pivoting handle thereof in a fully actuated position.
Figure 32:
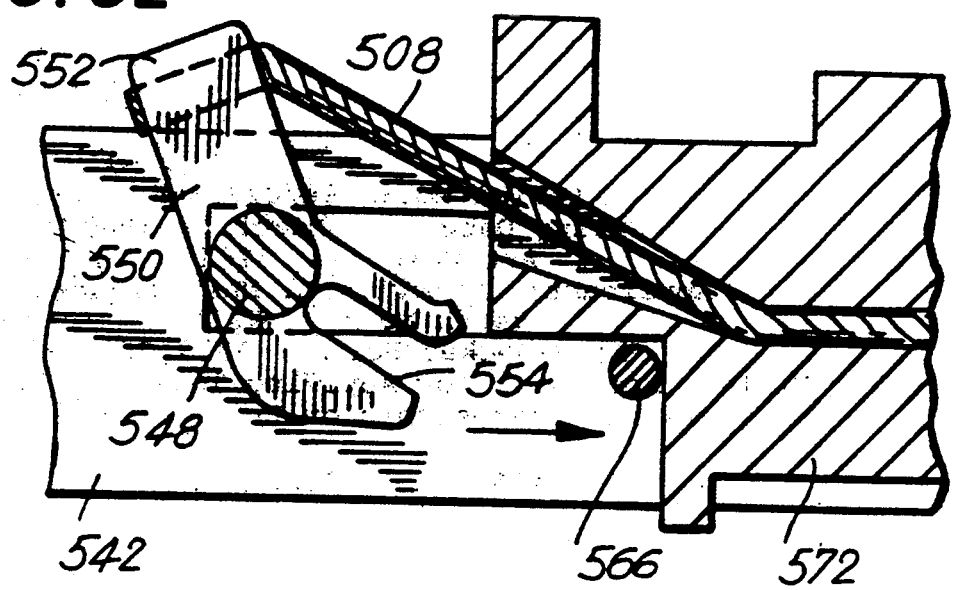
FIG. 32 is a view taken along lines 32—32 of FIG. 31 illustrating the cammed cable drawing mechanism of FIG. 26 in a second cable drawing position.
Figure 33:
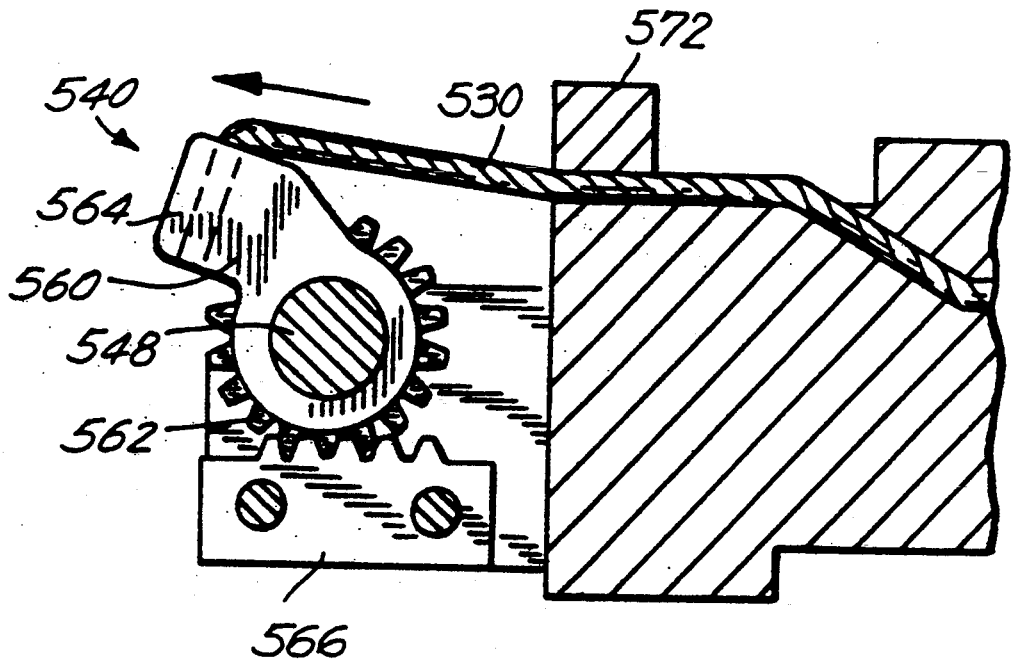
FIG. 33 is a view taken along lines 33—33 of FIG. 31 illustrating the geared cable drawing mechanism of FIG. 27 in a second cable drawing position.

In use, gradual manipulation of actuation handle 506 through a first distance from the position of FIG. 24 to that of FIG. 28 will cause distal movement of slide plate 542 through a first distance causing the rotation of cable crank 550 through approximately a 45° sector of rotation to draw approximation cable 408 proximally, while manipulation of actuation handle 506 through a second distance from the position of FIG. 28 to that of FIG. 31 will cause distal movement of slide plate 542 through a second further distance, causing continued counter-clockwise rotation of pinion gear 560 through approximately a 45° sector of rotation, as shown in FIG. 33, to draw driving cable 430 proximally.

A third embodiment of the handle assembly of the surgical apparatus 10 of the subject invention is illustrated in FIGS. 34–37 and is designated generally by reference numeral 600. Handle assembly 600 is substantially different than either of the handles discussed hereinabove (i.e. handle assembly 400 and handle assembly 500) in that handle assembly 600 has separate actuation handles for effectuating the movement of each of the transmission cables. In particular, handle assembly 600 comprises barrel portion 602, stationary handle 604 depending from barrel portion 602, actuation handle 606 pivotably connected to barrel portion 602 at a pivot point 605 for effectuating reciprocating movement of approximation cable 608, and an articulating handle 625 pivotably connected to the barrel portion 602 of handle assembly 600 for effectuating reciprocating movement of driving cable 630.

Figure 34:
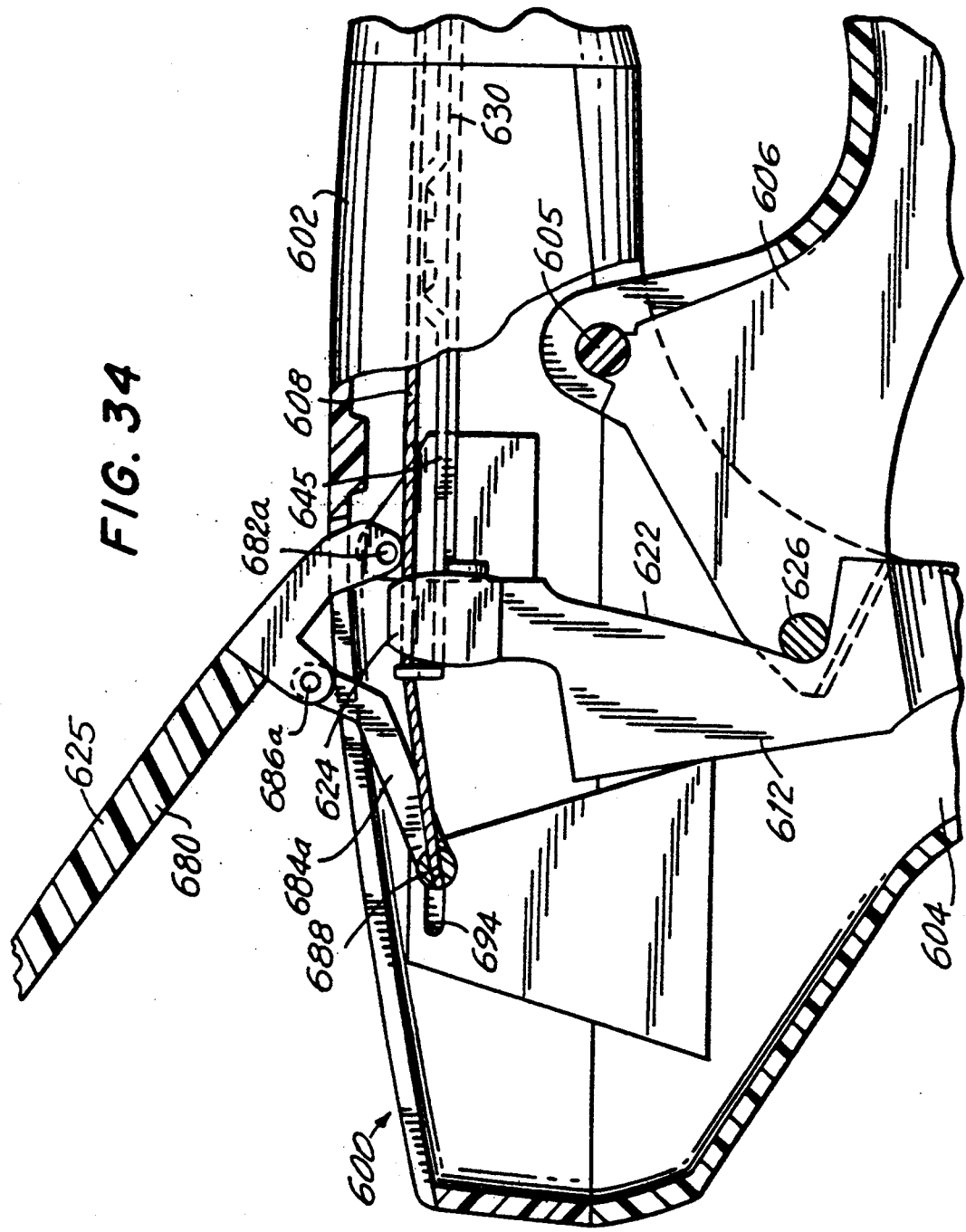
FIG. 34 is a side elevational view, partially in cross-section, of a third embodiment of a handle assembly in accordance with the subject invention.
Figure 35:
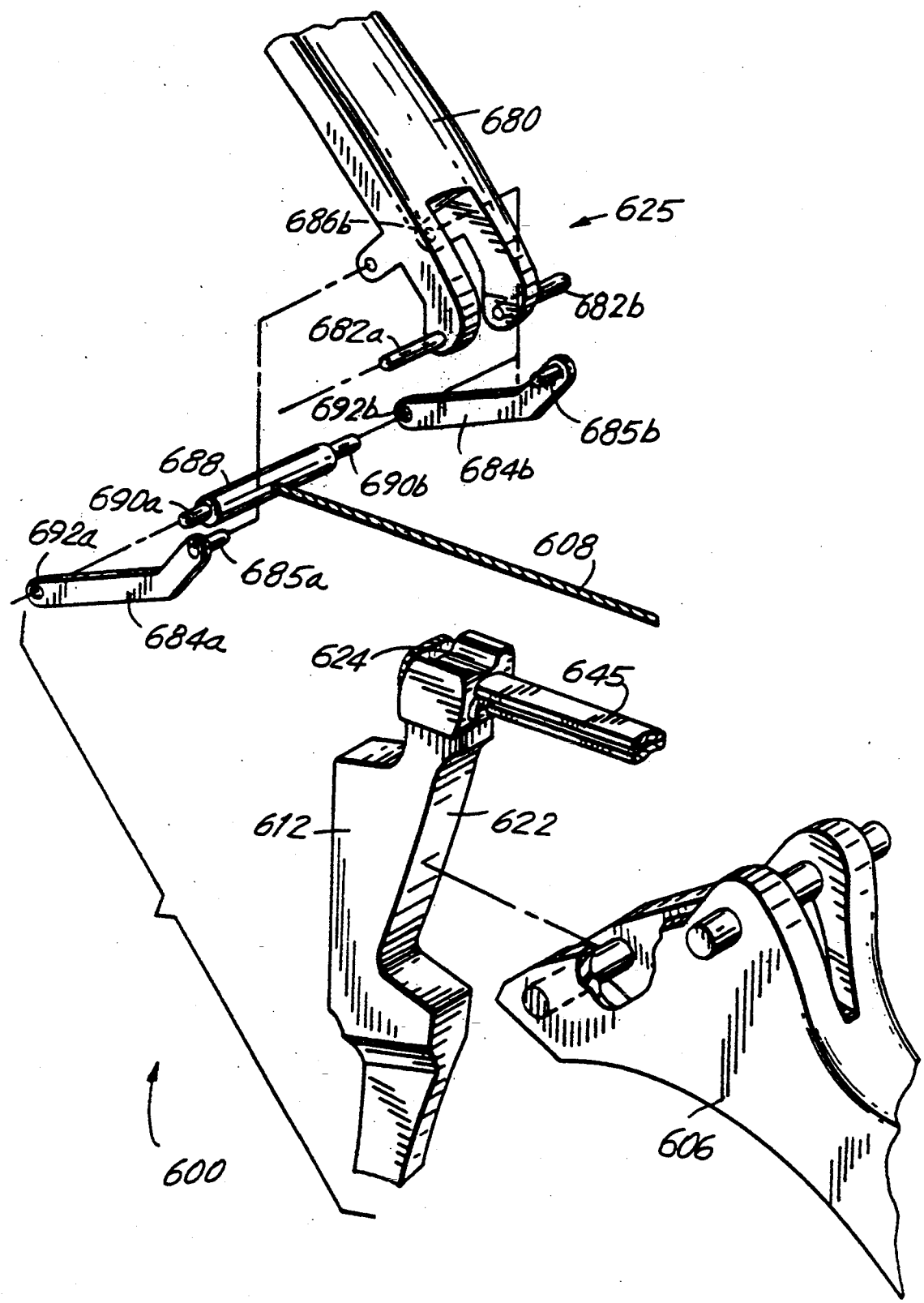
FIG. 35 is a perspective view with parts separated for convenience of illustration, of the handle assembly of FIG. 34.
Figure 36:
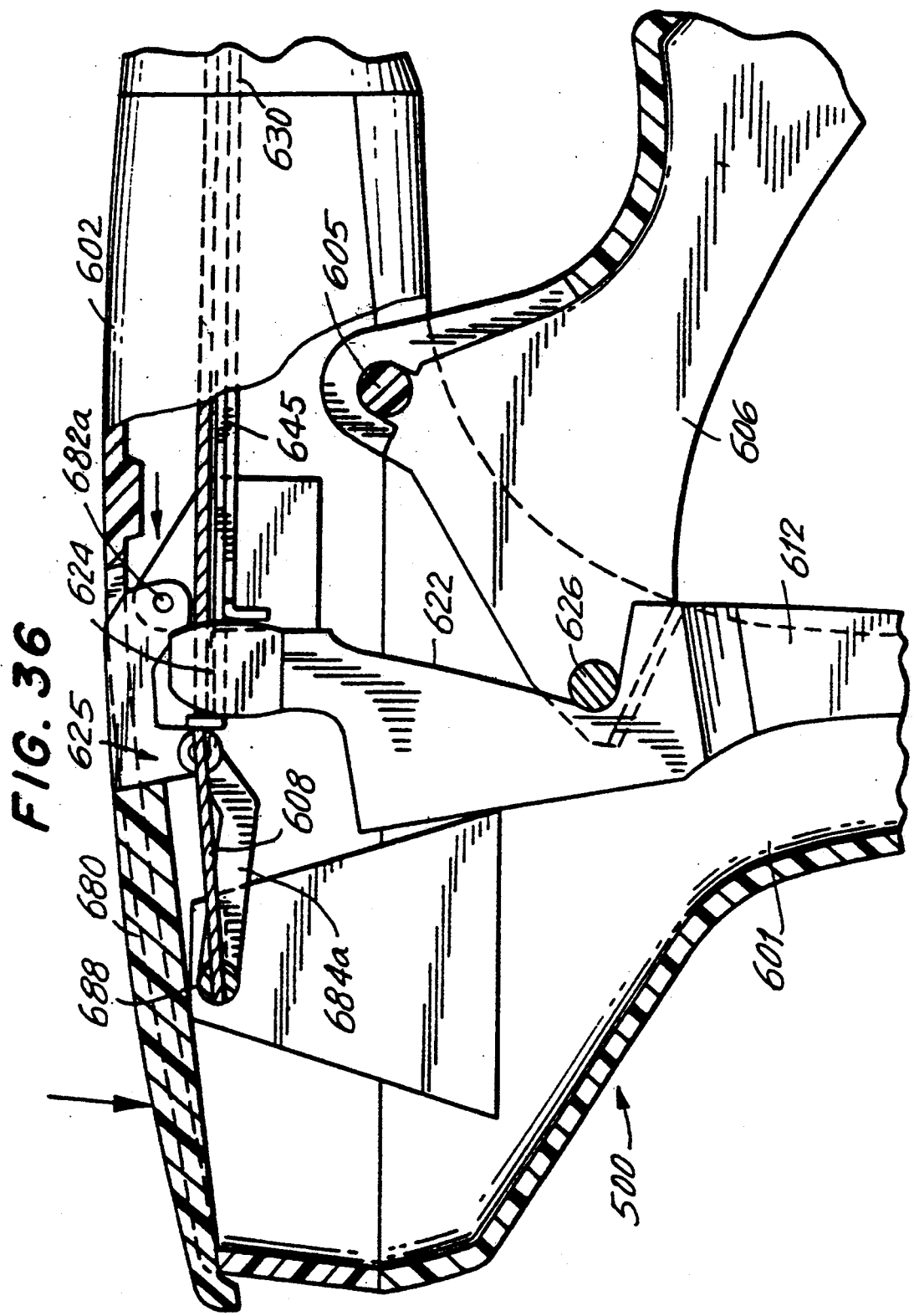
FIG. 36 is a side elevational view, partially in cross-section, of the handle assembly of FIG. 34 with the first actuation handle in a closed position.
Figure 37:
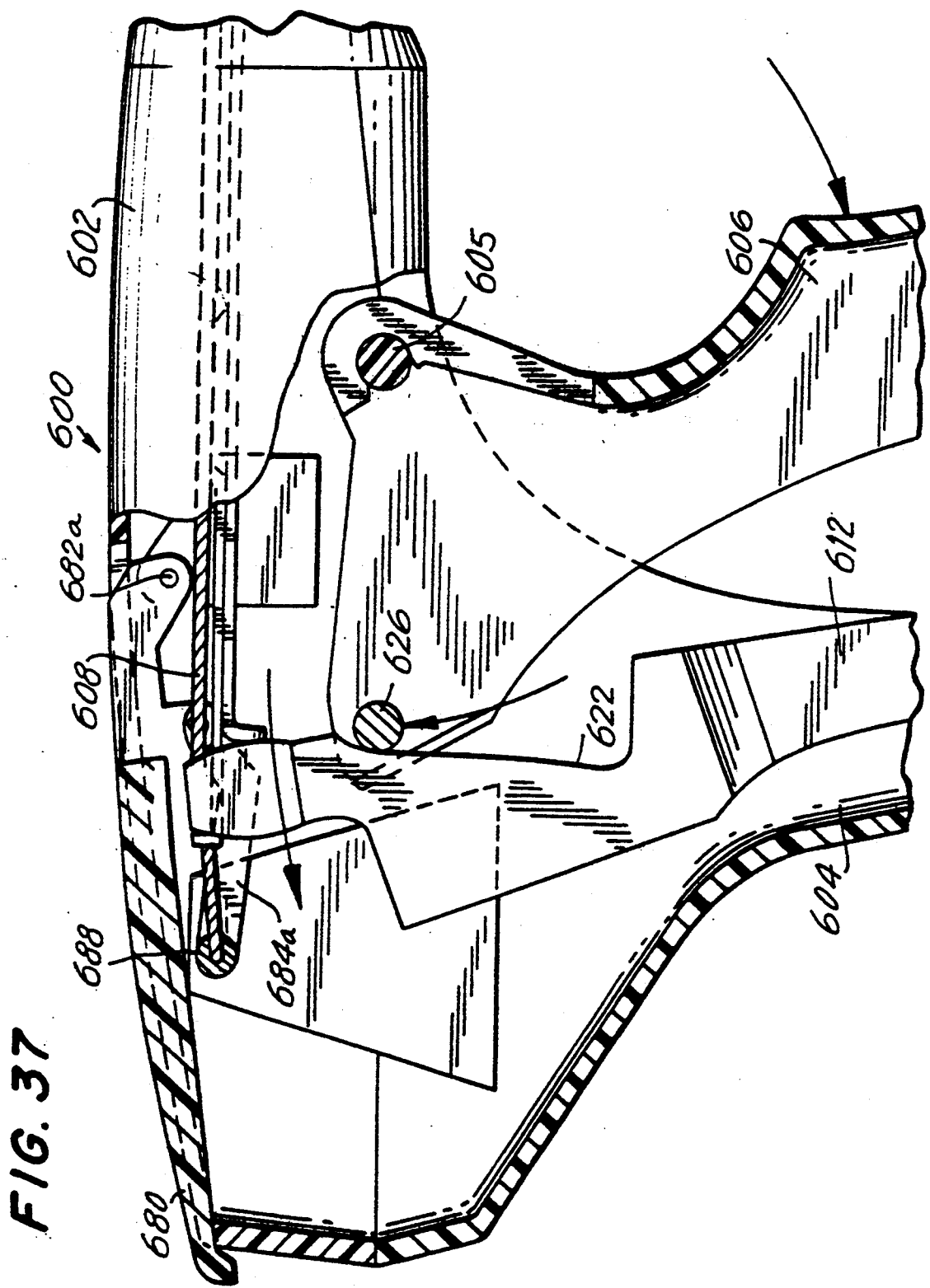
FIG. 37 is a side elevational view, partially in cross-section, of the handle assembly of FIG. 34 with the second actuation handle in a fully actuated position.

Referring to FIG. 34, the articulating handle 625 of handle assembly 600 includes a main handle member 680 connected pivotally to barrel portion 602 by pivot pins 682a and 682b. A pair of handle links 684a and 684b are pivotably connected to main handle 680 by respective pivot pins 685a and 685b extending through corresponding ports 686a and 686b. Transverse cable connector pin 688 is pivotably connected to handle links 684a and 684b through opposed pins 690a and 690b which extend through corresponding ports 692a and 692b. Cable connector pin 688 is adapted to mountingly receive the proximal end of approximation cable 608 to effect the drawing thereof. Transverse cable connector pin 688 is mounted for movement within opposed linear tracks 694 defined in the side walls of barrel portion 602 of handle assembly 600. Manipulation of main handle 680 toward barrel portion 602, as illustrated in FIG. 36, will cause handle links 684a and 684b to urge cable connector pin 688 proximally, drawing therewith approximation cable 608 to cause the opposed jaws of the fastener applying assembly to close upon one another.

Similar to handle assembly 400, handle assembly 600 shown in FIG. 34 includes an actuation cam 612 housed substantially within stationary handle 604 and pivotably movable in a counter-clockwise direction in response to translation of a cam follower 626 along an angled cam path 622 defined on the forward surface of actuation cam 612. The proximal end of driving cable 630 is mounted to a cable fastener plate 645, the proximal end of which is configured for engagement in the mounting portion 624 of actuation cam 612. Thus, manipulation of actuation handle 606 from the position of FIG. 36 to that of FIG. 37 will cause counter-clockwise movement of actuation cam 612, drawing driving cable 630 in a proximal direction as fastener plate 645 is pulled rearwardly to drive the fastener portion of the two-part fastener into engagement with the retainer portion thereof.

Referring now to FIG. 38, an alternative embodiment of a surgical apparatus constructed in accordance with the subject invention is illustrated and is designated generally by reference numeral 700. Surgical apparatus 700 is similar in most respects to the apparatus of the previous embodiments, but incorporates additional features which function to increase the operational range of the instrument. More specifically, surgical apparatus 700 incorporates a fastener applying assembly adapted for articulated or pivoted movement through an angular sector of rotation relative to a longitudinal axis defined by the endoscopic portion of the instrument. Additionally, a detent mechanism is also provided for positively establishing the articulated positions of the fastener applying assembly with respect to the longitudinal axis defined by the endoscopic portion of the instrument. A frame of reference is provided in FIG. 38 which defines the longitudinal axis of endoscopic portion 704 as the x-axis and the axis about which the fastener applying assembly 706 rotates as the z-axis.

The combination of the above-listed features provides extremely precise positioning of a two-part surgical fastener at numerous angular orientations to facilitate application thereof at a precise location. These features, combined with the features described in connection with the previous embodiments of the subject invention, individually or in combination, provide a surgical apparatus which represents a significant improvement over the highly effective embodiments described previously.

Surgical apparatus 700 is illustrated in FIG. 38 and comprises a handle portion 702 and an endoscopic section 704 having at the distal end portion thereof a fastener applying assembly 706 which includes a fastener support arm 708 on which is mounted a retainer support arm 710. Generally, the handle portion 702 supports the actuating components described hereinabove in connection with the previous embodiments of the invention. Furthermore, it may be stated that the fastener support arm 708 is pivotally mounted to the distal end of the endoscopic portion 704 and such pivotal movement thereof will result in similar movement of the retainer support arm 710 since it is directly associated therewith.

The mechanism for effectuating articulated pivotal movement of the fastener applying assembly of surgical apparatus 700 between a plurality of selected angled positions with respect to the longitudinal axis of the endoscopic section 704 is illustrated in FIGS. 39–43 and is specifically controlled through manipulation of a knurled collar 725 disposed adjacent the barrel of handle portion 702. The preferred dimensions of components such as the links and the rods which form the mechanism have been selected to effect pivotal movements of the fastener applying assembly from about positive 45°, to about 0°, then to about negative 45°. However, the relevant dimensions and mechanical advantages of these components may be selected to provide other alternative angular orientations for the fastener applying assembly. For example, in an alternative preferred embodiment of the invention, the components may be configured to provide angular orientations of 0°, 32.5° and 65° for the fastener applying assembly as will be described in further detail hereinbelow.

Figure 39:
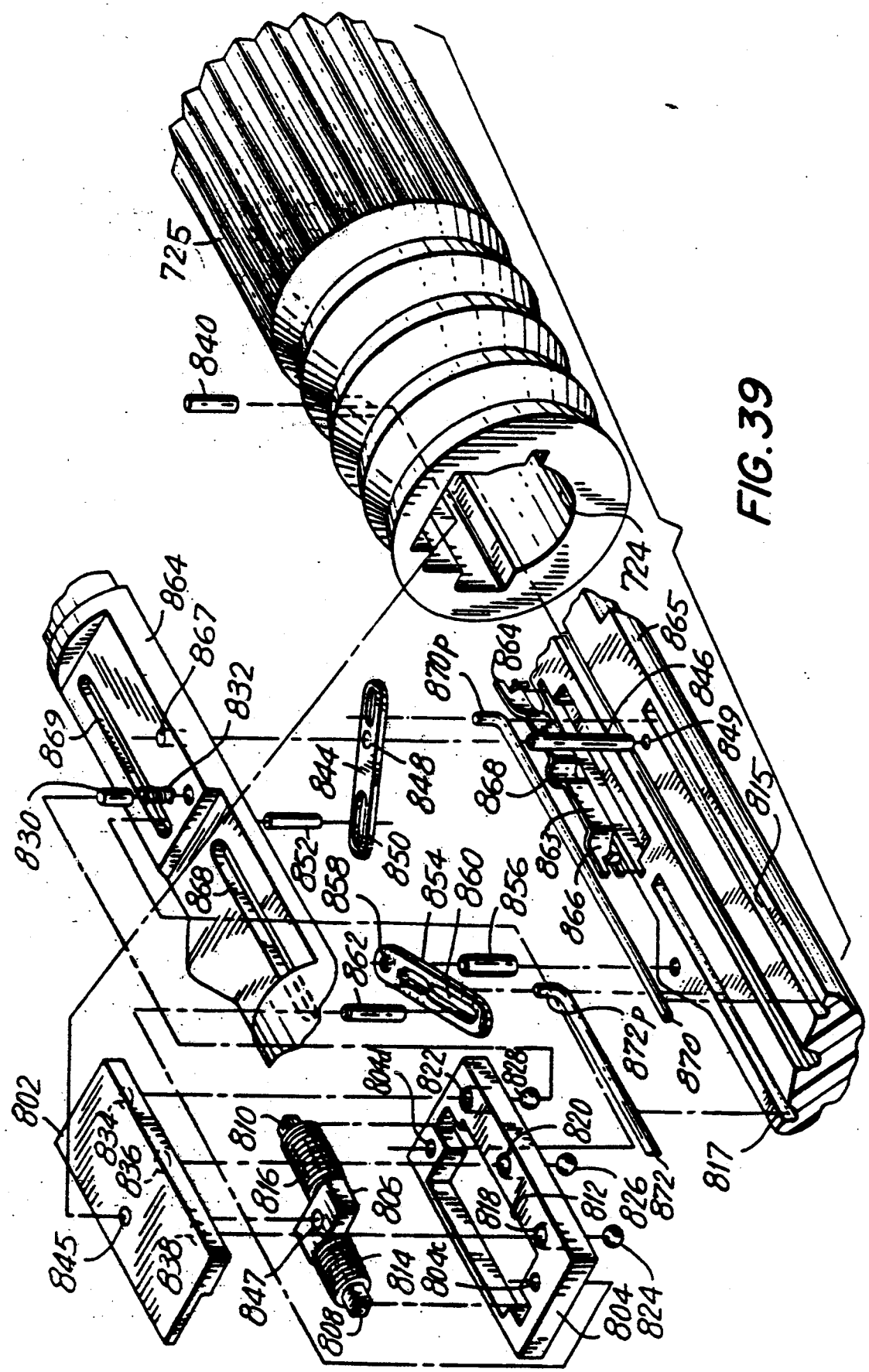
FIG. 39 is a perspective view with parts separated for convenience of illustration of a mechanism for effectuating the articulation of the fastener applying assembly of the surgical apparatus of FIG. 38.
Figure 40:
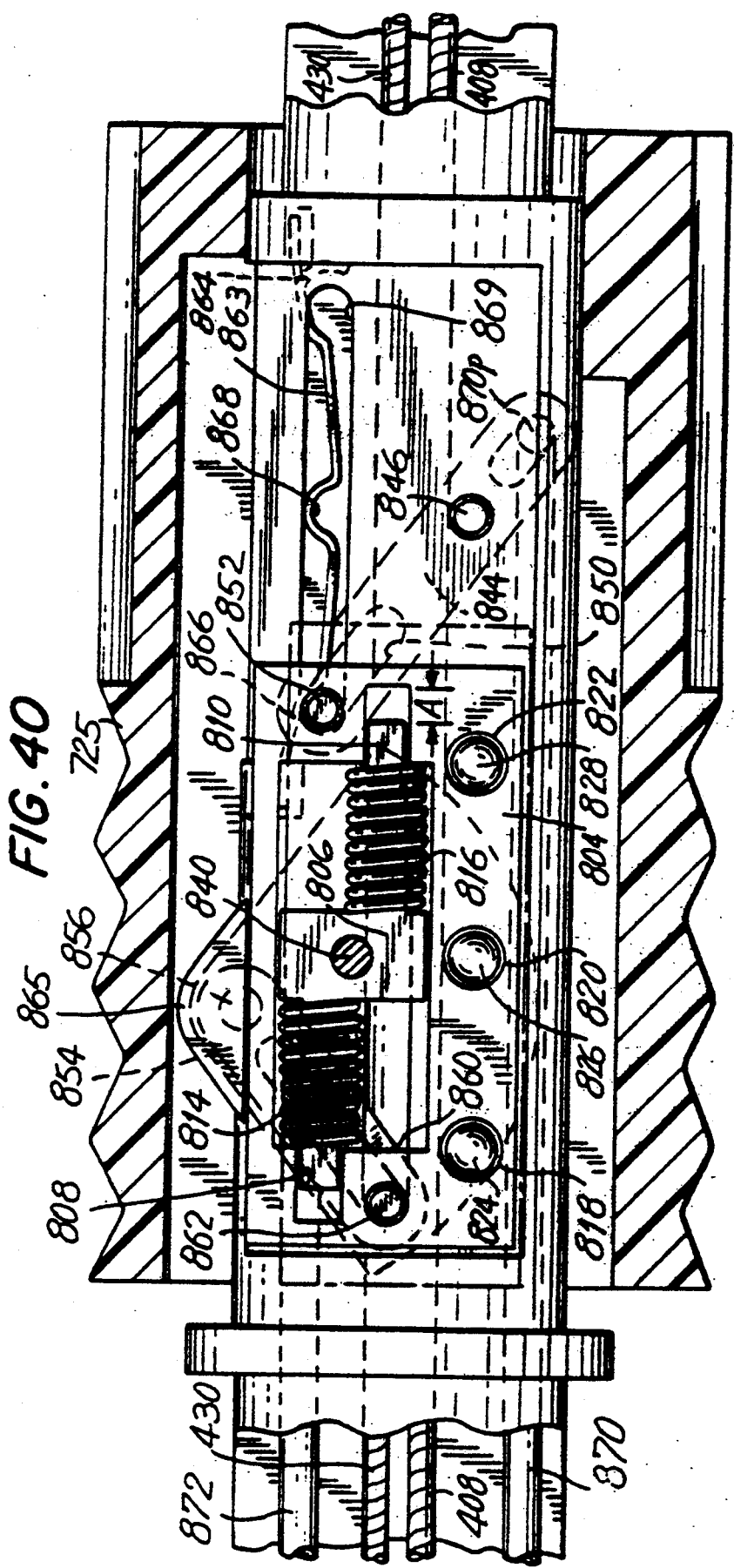
FIG. 40 is a cross-sectional view taken along lines 40—40 of FIG. 38 illustrating a first operative position of the articulation mechanism of FIG. 39.

Referring to FIG. 39, collar 725 is structured and dimensioned to contain a series of plates including an upper plate 802, a lower plate 804 and a central centering plate 806 having a distally extending leg 808 and a proximally extending leg 810. Lower plate 804 includes a cut-out 812 which is dimensioned and configured to receive centering plate 806 as shown in FIG. 40 with legs 808 and 810 respectively surrounded by coil springs 814 and 816. When the plates are assembled and positioned within axial opening 724 in collar 725 centering springs 814 and 816 serve to maintain the centered position of centering plate 806 within the cut-out 812 of lower plate 804. The assembled plates are then positioned within a mechanism housing defined by upper housing member 864 and lower housing member 865 adapted to interconnect with endoscopic portion 704.

Lower plate 804 contains cylindrical apertures 818, 820, and 822 in which are positioned corresponding locator balls 824, 826, and 828. Depending upon the position of lower plate 804 with respect to lower housing 865, pin 830 is biased upwardly by spring 832 to position the balls within the respective conical aperture 834, 836, and 838 to locate and fix the position of upper plate 802.

Pin 840 extends through aperture 842 in collar 725 and through aperture 845 in upper plate 802 as well as through aperture 847 in central plate 806 to key these components together for common distal and proximal movement. Proximal link 844 is pivotal about pin 846 which extends through aperture 848 in link 844, aperture 867 in upper housing 864, and aperture 849 in lower housing 865. Link 844 contains slot 850 for slidable reception of pin 852. Pin 852 is longitudinally slidable between a distal position and a proximal position within slot 866 in upper housing 864, and also extends through aperture 804d in central plate 804. Similarly, distal link 854 is pivotal about pin 856 which extends through aperture 858 and contains slot 860 for slidable reception of pin 862. Pin 862 is longitudinally slidable between a proximal position and a distal position in slot 869 in upper housing 864, and also extends through aperture 804c in central plate 804.

A detent spring 863 which contains three arcuate relief sections including distal arcuate detent relief 866, proximal detent relief 864, and medial U-shaped detent relief 868 for respective engaged resilient reception of proximal slidable pin 852. Links 844 and 854 respectively receive the upturned ends 870p and 872p of drive rods 870 and 872 respectively, each of which are respectively arranged at their distal ends 870d and 872d to engage wall portions 821 and 823 defined in the fastener support arm of the fastener applying assembly to effect articulated movement thereof as parallel rods 870 and 872 are moved reciprocatingly in response to manipulation of collar 725 (see FIGS. 43-45).

In operation, the initial translation of collar 725 will cause it to advance from the distalmost position thereof, corresponding to the fastener applying assembly disposed at 0° relative to the longitudinal axis of the endoscopic section, i.e. in line with the section 704 as shown in FIG. 43. In this position, pin 852 is engagably nestled within distal spring detent 866 as shown in FIG. 40 while proximal link 844 and distal link 854 are positioned as shown. The engaged position of rod 852 in spring detent 866 provides a first detent to retain push rods 870 and 872 from movement, thereby securing the 0° position of the fastener applying assembly 706. In addition, as shown in FIG. 40, locator ball 828 is positioned within conically shaped indentation 834 in upper plate 802 to provide a second detent mechanism to restrain the movement of push rods 870 and 872 by outer plate 802 against proximal and distal movements. Thus, the 0° position of assembly 706 is established and fixed by a dual detent system.

Referring now to FIGS. 40-45, the mechanical movements required to produce articulated movement of the fastener applying assembly 706 are effectuated by manipulating collar 725 so as to cause proximal advancement thereof such that outer plate 802 and centering plate 806 move proximally through common connector pin 840. This proximal movement causes coil spring 816 to engage walls 812a and 812b of lower plate 804 until the spring is sufficiently compressed and proximal leg 810 moves through a distance "A" shown in FIG. 40. At this point, leg 810 engages wall 804a of lower plate 804 such that continued proximal advancement of the collar 725 causes corresponding movement of lower plate 804. Prior to such engagement, limited movement of upper plate 802 has taken place to begin camming ball 828 out of conical indentation 834 as shown in FIG. 53.

Figure 41:
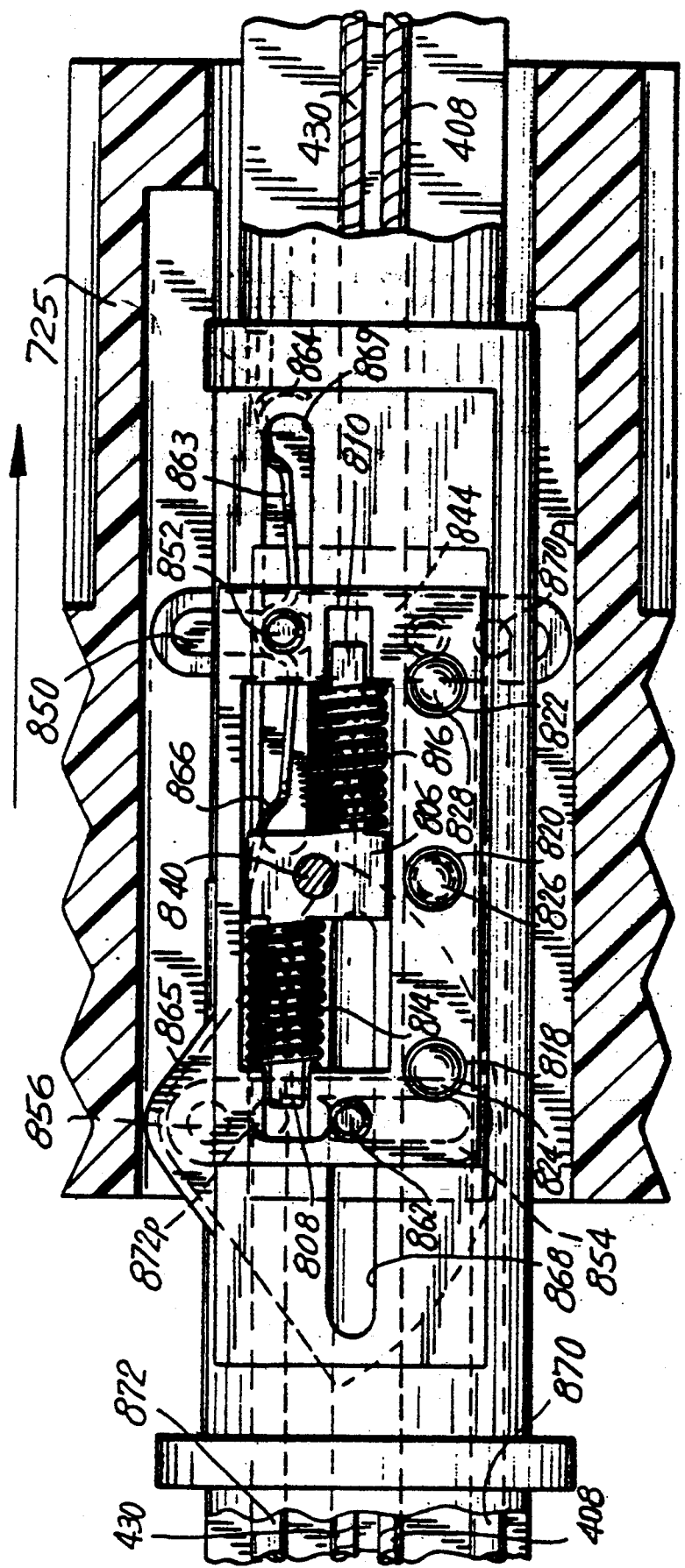
FIG. 41 is a cross-sectional view taken along lines 40—40 of FIG. 38 illustrating a second operative position of the articulation mechanism of FIG. 39.

The effect of moving ball 828 is to depress the ball and pin 830 against spring 832 causing upper plate 802, intermediate plate 806, and lower plate 804 to move proximally together until pin 830 engages central ball 836. This movement results in proximal movement of pin 852 to the central detent 868 of spring 863 as shown in FIG. 41. In this Fig., the distal link 854 has moved counter-clockwise and the proximal link 848 has moved clockwise. The rotational movement of proximal link 848 is due to the constraint on pin 852 to slide in slot 866 in upper housing 864 whereas pin 862 associated with proximal link 854 is constrained to move longitudinally within slot 868 in upper housing 864. Thus, the respective rotational movement of links 848 and 854 as described, in turn, result in proximal movement of the bent proximal end 872p of push rod 872 which is slidably positioned in the upper portion 861 of slot 860 in link 854 and the distal movement of bent proximal end 870p of push rod 870 which is slidably positioned in lower slot 845 of proximal link 844. The result of the pivotal rotation of the links 848 and 854 thus causes the distal ends 870d and 872d of push rods 870 and 872 to move proximally and distally, respectively, causing the assembly 706 to pivot to the 32.5° position shown in FIG. 44.

As the components translate to effect articulated pivotal movement of assembly 706, push rod 870 is slidably maintained within elongated slot 815 in the upper and lower housings 864 and 865 and push rod 872 is slidably maintained within elongated slot 817 in the upper and lower housings 864 and 865. The lower half portions of these slots 815 and 817 are seen clearly in FIG. 39 in the lower housing 865. The respective working end portions of push rods 870 and 872 engage suitably configured wall portions 821 and 823 of the fastener support arm as shown in FIGS. 43-45 to effect the desired movement.

After the pivotal movement of assembly 706 has been completed, and the desired position established, collar 725 may be released and this action will relieve the pressure of coil spring 816 to permit the central centering plate 806 to assume the neutral central position within aperture 812 of lower plate 804 under the natural resilient action of spring 816.

Figure 42:
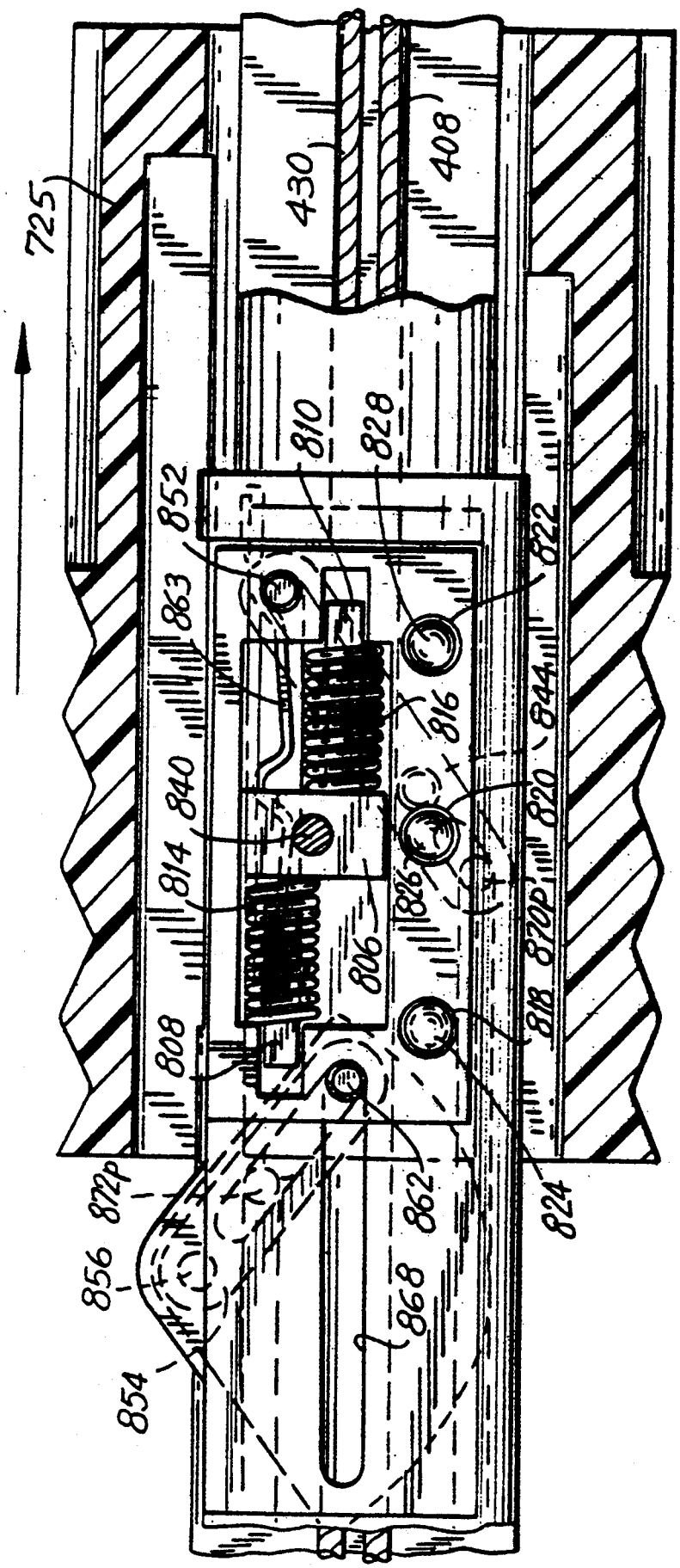
FIG. 42 is a cross-sectional view taken along lines 40—40 of FIG. 38 illustrating a third operative position of the articulation mechanism of FIG. 39.
Figure 46:
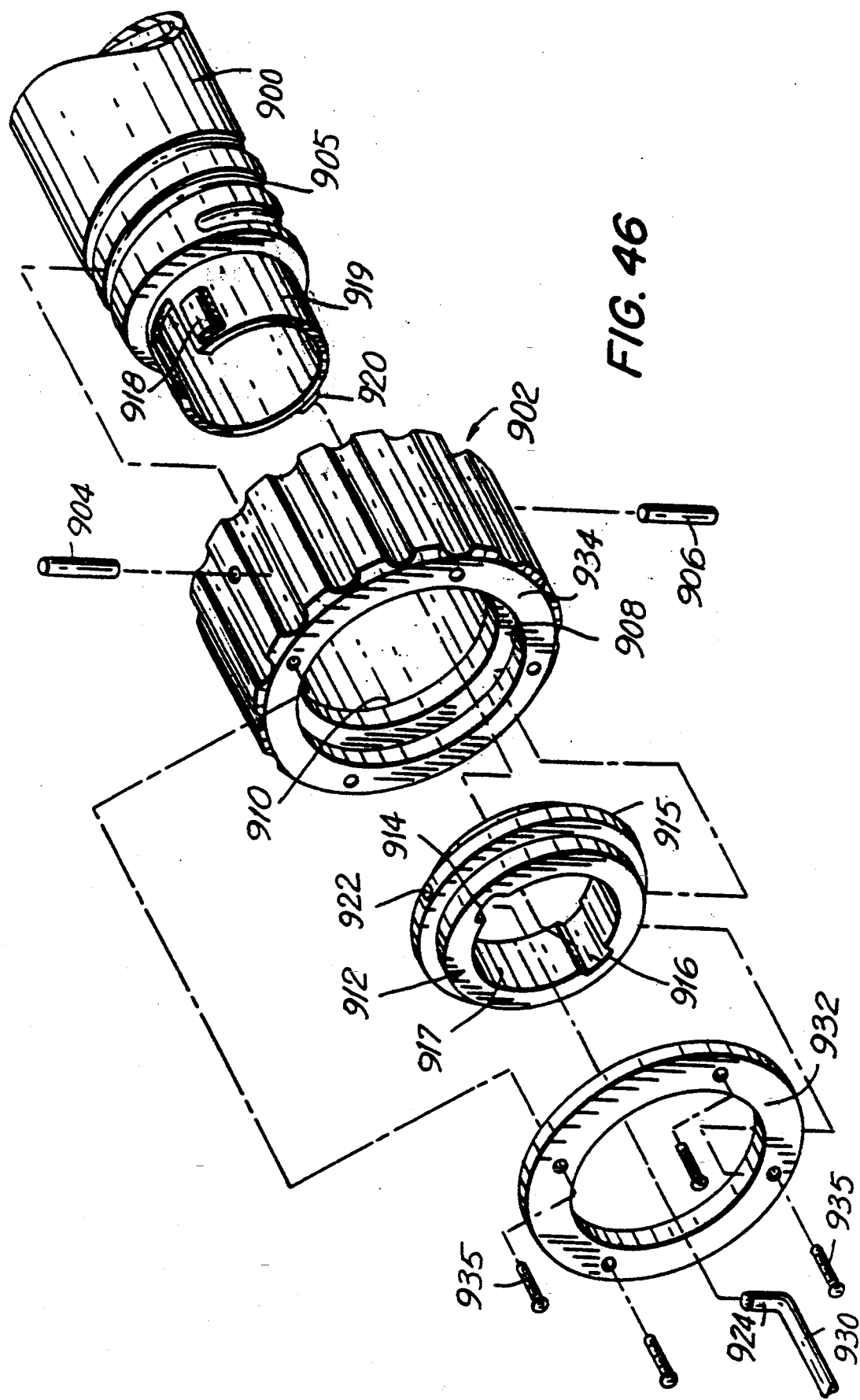
FIG. 46 is an exploded perspective view of another mechanism for effectuating the articulation of the fastener applying assembly of the surgical apparatus of FIG. 38.

Referring now to FIG. 42, the movement of the components to effect articulated pivotal movement of the fastener applying assembly 706 from the 32.5° position of FIG. 44 to the 65° position shown in FIG. 45 will now be described. This movement is produced by continued manual proximal movement of collar 725 to effect corresponding continued proximal movement of centering plate 806 and lower plate 804 in the same manner as described to effect 32.5° of movement of assembly 706.

Continued proximal movement of collar 722 will cause collar spring 816 to become compressed, as described above, until collar spring 816 again engages shoulders 812a and 812b. Once the proximal end of leg 810 of centering plate 806 engages the proximal wall portion 804a of lower plate 804 the proximal movement of collar 722 will terminate.

During the initial movement described hereinabove, the camming action between central conical aperture 836 in upper plate 802 begins depressing central ball 826 against spring 832 to begin releasing the locking engagement therebetween such that at approximately the point when the central centering plate becomes keyed to the lower plate, the ball 826 has been withdrawn from conical indentation 836, thus permitting movement of plates 802, 806, and 804. At this point pin 832 is positioned beneath distal ball 824 permitting the ball to be received into distal aperture 818 of upper plate 802. With this movement of the upper plate 802 and lower plate 804 in the proximal direction, pin 862, which is slidably received within the lower portion of slot 861 of link 854, and which extends through aperture 804c, causes continued clockwise rotation of distal link 854 about pivot pin 856 to the position shown in FIG. 42, causing continued proximal movement of push rod 872 within slot 817. Correspondingly, proximal link 844 is constrained to rotate further counter-clockwise causing continued distal movement of push rod 870 within slot 815. This movement results in further articulated movement of the fastener applying assembly 706 to the 65° position shown in FIG. 45, in a manner similar to that described previously.

In the position of the components shown in FIG. 42, assembly 706 is locked in the 65° position by the bias of spring 832 against pin 830 which locks ball 824 within distal conical aperture 818 in upper plate 804. Further locking action is obtained by the resilient force of proximal detent relief 864 of spring 863 against pin 852 slidably positioned in slot 845 of proximal link 844. When the desired position of assembly 706 has been achieved release of collar 725 will permit central centering plate 806 to return to its central position within aperture 812 of lower plate 804, thereby relieving the stress on coil spring 816.

Once the jaws are articulated to either of the 32.5° or 65° angular orientations, reversal of the motion to return assembly 706 toward the 0° position is simply obtained by reversal of the movements described hereinabove. In particular, collar 725 is manually returned toward its original distal position causing the movement of the components as previously described to be reversed. Ultimately, when collar 725 is moved to the distalmost position, all internal components return to the relative positions shown in FIG. 41 and fastener applying assembly 706 returns to the 0° angular position.

As illustrated in FIG. 38, collar 725 is also adapted and configured to effectuate rotation of endoscopic portion 704 about the longitudinal axis thereof relative to the handle assembly 702 of surgical instrument 700. Axial rotation of endoscopic portion 704 will further increase the operational range of the fastener applying assembly 706 during a surgical procedure.

As noted hereinabove, in a preferred embodiment of the subject invention, the articulation mechanism illustrated in FIGS. 39-43 is configured to articulate the fastener applying assembly 706 within a 90° sector of rotation. More particularly, the structural elements of the articulation mechanism described hereinabove may be configured to effectuate articulation of the fastener applying assembly 706 to about 45° and about −45° with respect to the longitudinal axis defined by endoscopic portion 704 (see FIG. 38). In operation, manipulation of collar 725 from the position illustrated in FIG. 41 to that which is shown in FIG. 42 will effect articulation of fastener applying assembly 706 from a 0° orientation to about a 45° orientation with respect to the longitudinal axis of endoscopic portion 704 (see FIG. 44A).

Conversely, moving collar 725 from the position illustrated in FIG. 41 to that which is shown in FIG. 40 will effect articulation of fastener applying assembly 706 from the 0° orientation, in axial alignment with the longitudinal axis of endoscopic portion 704, to about a −45° orientation with respect to the longitudinal axis defined by endoscopic portion 704 (see FIG. 44B).

An alternative mechanism for effectuating gradual pivoted articulation of the fastener applying assembly 706 of surgical apparatus 700 within an angular sector of rotation is illustrated in FIGS. 46–50. The mechanism is configured for remote manipulation by the user and comprises a threaded nose piece 900 which is preferably associated with the barrel of handle assembly 702 and which defines a helical thread 905 configured for facilitating axial advancement of actuation collar 902 through provision of a pair of diametrically opposed thread following pins 904 and 906 which are dimensioned for travel within thread 905. An annular race 908 is defined within the axial bore 910 of actuation collar 902 for accommodating annular mounting ring 912. Mounting ring 912 has a peripheral flange 915 dimensioned for seated engagement in race 908. A pair of diametrically opposed slots 914 and 916 are provided on the inner circumferential surface 917 of mounting ring 912 and are dimensioned for engaging corresponding ridges 918 and 920 formed on the outer circumferential surface 919 of the distal end of nose piece 900 to fix the angular orientation of ring 912 with respect to nose piece 900, while permitting rotation of collar 902 about a longitudinal axis defined by endoscopic portion 704 of the apparatus. A mounting aperture 922 is formed in mounting ring 912 extending radially through the peripheral flange area 915 thereof for reception of an upturned engaging end portion 924 of an elongated actuation rod 930. Actuation rod 930 extends at least partially through the endoscopic portion of surgical apparatus 700 to operatively associate with an articulation cable assembly which will be discussed in detail hereinbelow. Finally, an annular cover plate 932 is adapted to be fastened to the distal surface 934 of actuation collar 902 by a plurality of fasteners 935 to maintain the mounting ring 912 within the annular race 908.

Turning now to FIG. 47, a distal end portion 936 of actuation rod 930 is terminated in a cable coupling member 938 which is fastened to a looped articulation cable 940. Articulation cable 940 defines a leading portion 942 and a trailing portion 944. The leading portion 942 is operatively mounted to a distal crank member 946 through reception of an integral lock ball 948 within an engagement port 950. Similarly, the trailing portion 944 of articulation cable 940 is operatively mounted to a proximal crank member 952 through reception of an integral lock ball 954 within a corresponding engagement port 956. Proximal crank member 952 is rotatably mounted upon a transverse post 958 which is secured intermediate the endoscopic portion of surgical apparatus 700. Distal crank member 946 is also rotatably mounted upon a transverse post 960 which is maintained in the distal end 962 of the endoscopic portion 704 of surgical apparatus 700, as best seen in FIG. 48.

Referring to FIGS. 48–50, distal crank member 946 is triple-tiered in configuration and includes upper tier 962 for accommodating the leading portion 942 of articulation cable 940, medial tier 964 defining a passageway for accommodating driving cable 430, and lower tier 966 defining a passageway for accommodating approximation cable 408. Parallel mounting pins 968 and 970 extend through the three-tiered structure of distal crank 946 and permit relative rotation of the upper tier 962 relative to the remaining tiers thereof in response to reciprocated movement of articulation cable 940. A transverse interconnection pin 972 extends upwardly from the upper tier 962 of distal crank 946, through an intermediate plate 974 which defines an arcuate guide track 975 for pin 972 (see FIG. 51), and into an aperture 976 formed in the proximal tail 978 of the fastener applying assembly 706 of surgical apparatus 700 (see FIG. 53). The arcuate path defined by guide track 975 defines the angular sector of rotation through which fastener applying assembly 706 travels during articulation.

During a surgical procedure, rotational manipulation of actuation collar 902 by the user will result in gradual longitudinal translation of actuation rod 930 with respect to endoscopic portion 704, as illustrated in FIGS. 47 and 48. As actuation rod 930 advances in a distal direction, the leading portion 942 of articulation cable 940 is gradually urged in a counter-clockwise direction. Conversely, proximal retreat of actuation rod 930 will result in clockwise rotation of articulation cable 940.

Figure 51:
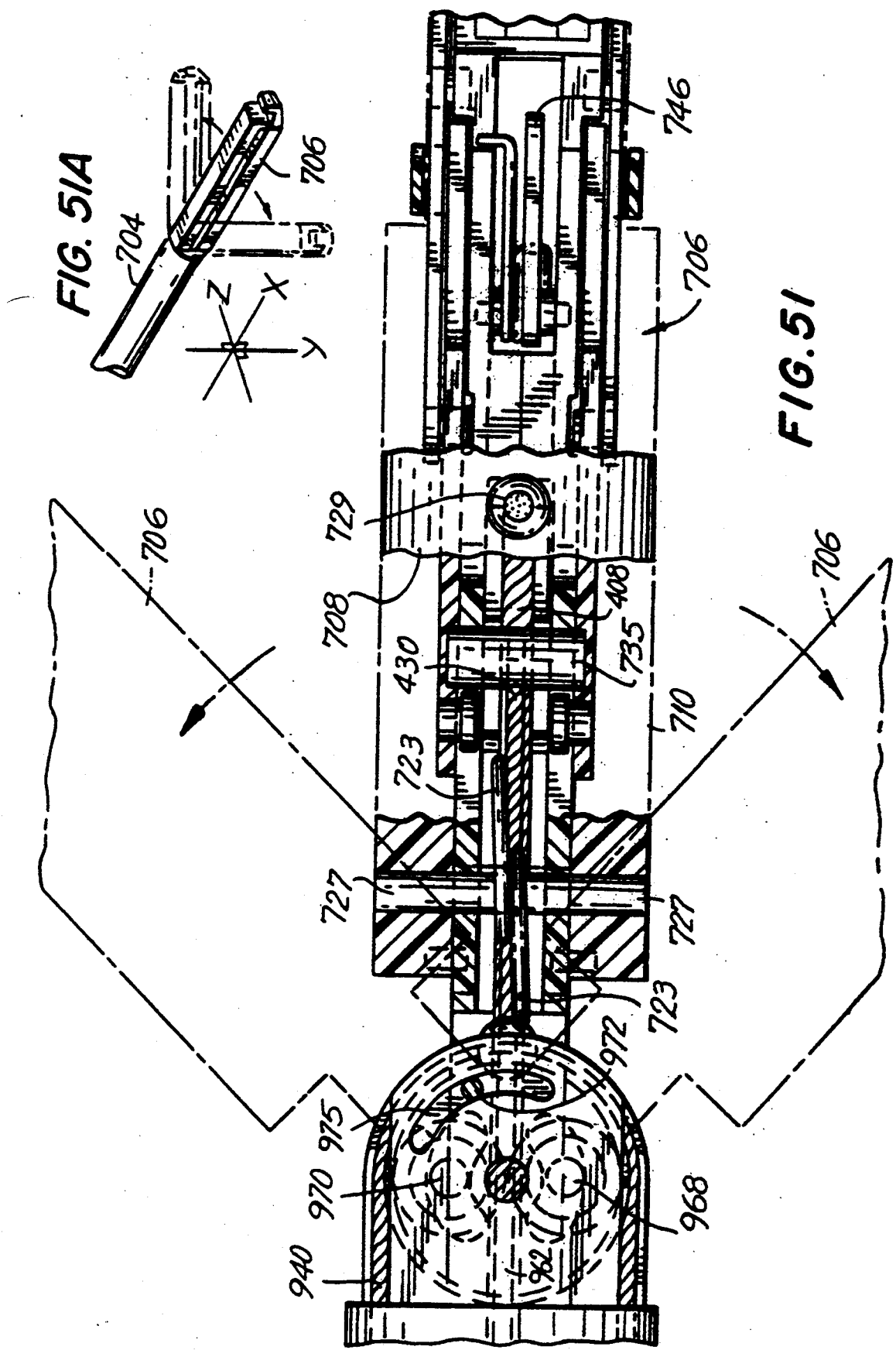
FIG. 51 is a top plan view in partial cross-section of the fastener applying assembly of the apparatus of FIG. 38 swept through an angular sector of rotation.

Referring to FIGS. 51 and 51A in conjunction with FIG. 49, a frame of reference is provided similar to that of FIG. 38, to define the longitudinal axis of endoscopic portion 704 as the x-axis. Thus, rotation of the upper tier 962 of distal crank 946 in response to movement of articulation cable 940 will cause interconnection pin 972 to progressively steer the fastener applying assembly 706 of surgical apparatus 700 through an angular sector of rotation about the y-axis.

Figure 52:
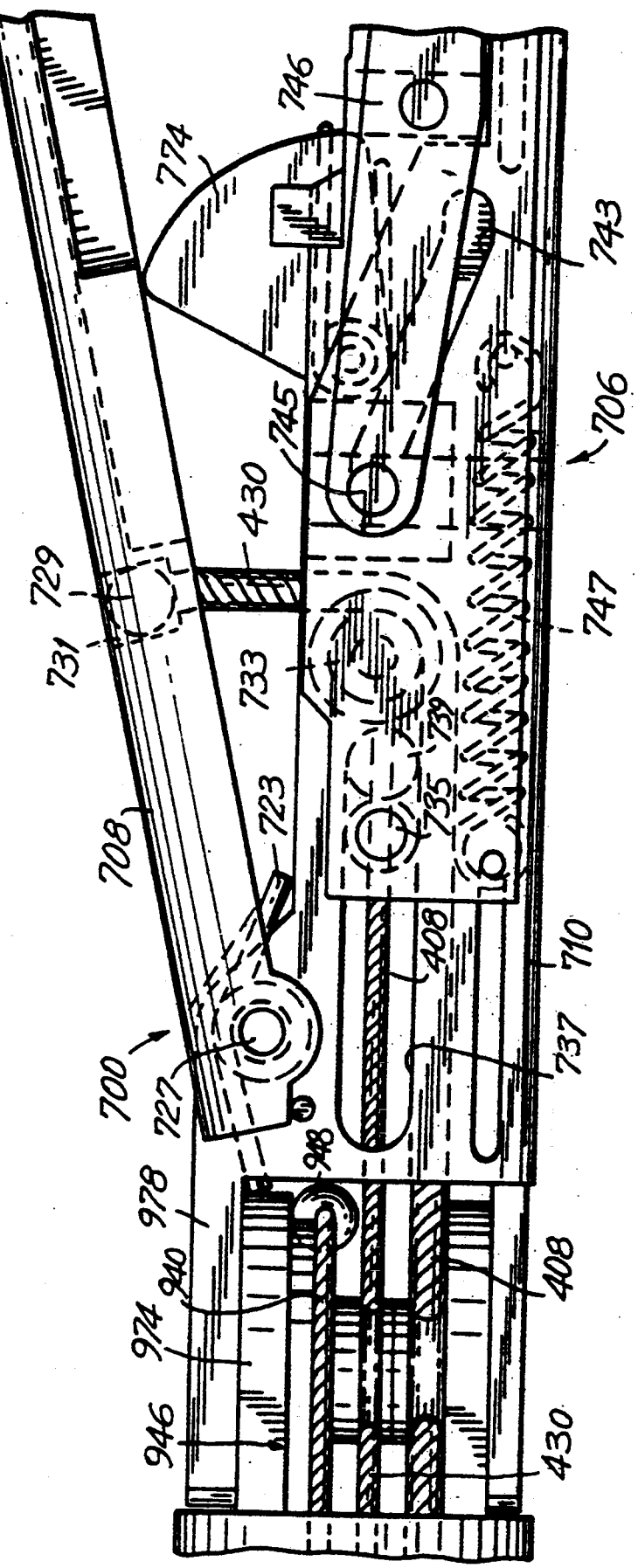
FIG. 52 is a side elevational view of the apparatus of FIG. 38 with the retainer supporting portion thereof in the open position.

Turning now to FIGS. 52–54, there is illustrated the operational sequence of the fastener applying assembly 706 of surgical apparatus 700. Prior to introducing the apparatus into the surgical site through a trocar or cannula device, the upper jaw 708 of fastener applying assembly 706 is approximated from the open position of FIG. 52 to the closed position shown in FIG. 53. As seen in FIG. 52, the upper jaw 708 of fastener applying assembly 706 is normally biased into the open position by a looped torsion spring 723 positioned about jaw pivot pin 727. The distal end of approximation cable 408 is provided with an integral lock ball 729 engaged within a corresponding reception port 731 formed in upper jaw 708.

As shown in FIG. 50, to effect approximation of the jaws, the line of action of cable 408 is transferred from a longitudinal direction to a direction perpendicular to the axis of the endoscopic portion 704 by a cylindrical pulley 733 mounted within the lower jaw 710 of fastener applying assembly 706. Approximation of the jaws can be achieved, for example, by drawing cable 408 proximally through manipulation of actuation handle 406 from the fully open position of FIG. 20 to the partially closed position shown in FIG. 22. Subsequently, actuation handle may be locked in the partially closed position by latch member 420.

After the jaws have been approximated and the instrument has been introduced to the operative site, the surgeon may release and lock out of place the spring-biased over-centered latch 420 of locking mechanism 416 to permit the jaws of fastener applying assembly 706 to move to their normally open position of FIG. 52. At such a time, actuation handle 406 is once again in the position shown in FIG. 20. With the jaws in their open position, the surgeon may position them relative to the tissue to be fastened. As the target tissue is oriented between the jaws of the fastener applying assembly 706, tissue stop 774 serves to inhibit the tissue from becoming entrapped, thus limiting the possibility of trauma.

Once the target tissue has been properly oriented between the jaws of fastener applying assembly 706, the surgeon may manipulate actuation handle 406 to approximate the jaws. At such time, the surgeon may operate one of the articulation mechanism discussed hereinabove to position the fastener applying assembly 706 in any angular orientation within the sector of rotation illustrated in FIG. 51 so as to increase the operational range of the instrument. Thereafter, further compression of actuation handle 406 to the fully actuated position shown in FIG. 23 will draw drive cable 430 proximally to effectuate engagement of the fastener portion of the two-part surgical fastener with the retainer portion thereof.

Turning to FIG. 54, the proximal end of drive cable 430 is terminated in a transverse link drawing pin 735 configured for translation within lateral guide slots (i.e. guide slot 737) which are defined in the lower jaw 710 of fastener applying assembly 706. Draw pin 735 is engaged to the right and left camming arms (i.e. arm 739) of the driving mechanism of fastener applying assembly 706. Thus, proximal translation of drive cable 430 will cause draw pin 735 to pull the camming arms proximally. As discussed previously with respect to other embodiments of the subject invention, the camming arms define angled cam slots at the distal ends such as cam slot 743 in camming arm 739 for effectuating translation of a cam follower 745 within a transverse track 747 defined in lower jaw 710. Downward translation of cam follower 745 in response to proximal movement of draw pin 735 from the distal-most position shown in FIG. 53 to the proximal-most position shown in FIG. 54 will effectuate counter-clockwise rotation of pivoting rocker arms (i.e. rocker arm 746) to urge the fastener portion of the two-part surgical fastener into engagement with the retainer portion thereof. Once the instrument has been fired, and actuation handle 406 has been released, a coiled biasing spring 747 which is associated with the lower jaw 710 of fastener applying assembly 706 serves to return the camming arms of the fastener driving mechanism to their distalmost positions, carrying therewith draw pin 735 and drive cable 430. At this point, the surgical apparatus of the subject invention is prepared for a subsequent fastener applying procedure.

To the extent not already indicated, it also will be understood by those of ordinary skill in the art to which the subject invention appertains that any one of the various specific embodiments herein described and illustrated may be further modified to incorporate features shown in other of the specific embodiments.

Although the endoscopic surgical instrument of the subject invention has been described and shown with respect to a preferred embodiment, it would be apparent to one of ordinary skill in the art that changes and modifications may be made thereto without departing from the spirit or scope of the invention as defined by the appended claims.

What is claimed is:

1. Apparatus for endoscopic application of two-part surgical fasteners each having a fastener portion and a retainer portion, which comprises:
    a) a handle assembly;
    b) an endoscopic portion extending from said handle assembly and defining a longitudinal axis;
    c) means for supporting the fastener portions of a plurality of two-part surgical fasteners in a longitudinal orientation, said means pivotally associated with a distal end portion of said endoscopic portion;
    d) means for supporting the retainer portions of a plurality of two-part surgical fastener in a position relative to said fastener portions; and
    e) means for resiliently biasing the plurality of fastener portions and the plurality of retainer portions in a longitudinal direction;
    f) first cable driven means for approximating said retainer portion supporting means and said fastener portion supporting means;
    g) second cable driven means for effectuating individual application of said plurality of two-part surgical fasteners by driving a fastener portion and a retainer portion into engagement with one another;
    h) means for pivoting said fastener applying assembly relative to said longitudinal axis of said endoscopic portion within an angular sector of rotation; and
    i) means for rotating said endoscopic portion about said longitudinal axis relative to said handle assembly.

2. Apparatus as recited in claim 1, wherein said pivoting means is operable remote from said fastener applying assembly.

3. Apparatus as recited in claim 2, wherein said means for remotely effectuating pivotal movement of said fastener applying assembly comprises third cable means including a looped articulation cable having a leading portion and a trailing portion, said leading portion associated with said fastener applying assembly and said trailing portion associated with means for reciprocatingly moving said looped articulation cable.

4. Apparatus as recited in claim 3, wherein said means for reciprocatingly moving said looped articulation cable comprises an axial drive screw assembly configured for effectuating progressive pivotal movement of said fastener applying assembly.

5. Apparatus as recited in claim 1, wherein said handle assembly includes a first pivoting actuation handle for effectuating movement of said first cable means and a second pivoting actuation handle for effectuating movement of said second cable means.

6. Apparatus for endoscopic application of a plurality of two-part surgical fasteners, each of said plurality of two-part surgical fasteners having a fastener portion and a retainer portion, which comprises:
    a) a handle assembly;
    b) an endoscopic portion extending from said handle assembly and defining a longitudinal axis;
    c) means for effectuating individual advancement of said plurality of two-part surgical fasteners toward a distal end of said endoscopic portion;
    d) tool means associated with a distal end portion of said endoscopic portion for effectuating individual application of said plurality of two-part surgical fasteners; and
    e) means associated with said handle assembly for effectuating movement of said tool means relative to said longitudinal axis of said endoscopic portion within an angular sector of rotation.

7. Apparatus as recited in claim 6, wherein said plurality of two-part surgical fasteners are formed of a bioabsorbable material.

8. Apparatus as recited in claim 6, wherein said tool means comprises means for supporting a plurality of fastener portions of said two-part surgical fasteners and means for supporting a plurality of retainer portions of said two-part surgical fasteners in a position relative to said plurality of retainer portions.

9. Apparatus as recited in claim 6, wherein said means for effectuating movement of said tool means comprises a looped articulation cable defining a leading portion and a trailing portion, said leading portion associated with said tool means and said trailing portion associated with a means for moving said articulation cable.

10. Apparatus as recited in claim 9, wherein said means for remotely moving said articulation cable comprises an axial drive screw assembly configured for effectuating progressive pivotal movement of said tool means.

11. Apparatus for endoscopic application of a plurality of two-part surgical fasteners each having a fastener portion and a retainer portion, which comprises:
   a) a handle assembly including a barrel portion, a first actuation handle, and a second actuation handle;
   b) an endoscopic portion extending from said barrel portion and defining a longitudinal axis;
   c) a fastener supporting assembly operatively associated with a distal end portion of said endoscopic portion and including:
      i) means for supporting a plurality of fastener portions; and
      ii) means for supporting a plurality of retainer portions in positions relative to said fastener portions; and
   d) means extending from said handle assembly to said fastener supporting assembly for actuating said fastener supporting assembly such that movement of said first actuation handle effectuates approximation of said fastener portion supporting means and said retainer portion supporting means, and movement of said second actuation handle effectuates individual application of said plurality of two-part surgical fasteners by driving of one of said plurality of fastener portions and one of said plurality of retainer portions into engagement with one another in a direction transverse to said longitudinal axis of said endoscopic portion.

12. Apparatus as recited in claim 11, wherein said means associated with said handle assembly and said fastener applying assembly comprises an approximation cable extending from said first actuation handle, through said endoscopic portion, to said fastener applying assembly.

13. Apparatus as recited in claim 12, wherein said means associated with said handle assembly and said fastener applying assembly comprises a driving cable extending from said second actuation handle through said endoscopic portion, to said fastener applying assembly.

14. Apparatus as recited in claim 11, further comprising means for moving said fastener applying assembly relative to said endoscopic portion within an angular sector of rotation.

* * * * *